United States Patent [19]
Kimura et al.

[11] Patent Number: 5,502,598
[45] Date of Patent: Mar. 26, 1996

[54] LENS FRAME SUPPORTING MECHANISM

[75] Inventors: Akiteru Kimura; Miki Matsuzaki, both of Hachioji; Atsuhiko Tanaka, Hino; Masatoshi Inoue, Hachioji, all of Japan

[73] Assignee: Olympus Optical Co., Ltd., Tokyo, Japan

[21] Appl. No.: 151,557

[22] Filed: Nov. 12, 1993

[30] Foreign Application Priority Data

| Nov. 12, 1992 | [JP] | Japan | 4-302667 |
| Aug. 2, 1993 | [JP] | Japan | 5-191352 |
| Sep. 6, 1993 | [JP] | Japan | 5-221263 |
| Sep. 6, 1993 | [JP] | Japan | 5-221264 |

[51] Int. Cl.[6] ............................................. G02B 7/02
[52] U.S. Cl. ................. 359/814; 359/822; 359/830
[58] Field of Search .......................... 359/811, 813, 359/814, 818, 819, 822, 829, 830, 844, 876, 874; 901/18

[56] References Cited

U.S. PATENT DOCUMENTS

| 4,628,765 | 12/1986 | Dien et al. | 901/18 |
| 4,639,081 | 1/1987 | O'Brien | 359/876 |
| 4,678,289 | 7/1987 | Mattelin et al. | 359/876 |
| 4,925,288 | 5/1990 | Harris | 359/876 |
| 5,367,407 | 11/1994 | Hügenell | 359/876 |

FOREIGN PATENT DOCUMENTS

| 4-104666 | 7/1992 | Japan . | |
| 0270110 | 7/1970 | U.S.S.R. | 901/18 |

*Primary Examiner*—Georgia Y. Epps
*Assistant Examiner*—Thomas Robbins
*Attorney, Agent, or Firm*—Louis Weinstein

[57] ABSTRACT

A lens frame supporting mechanism includes a spherical surface that is a specified region of the outer surface of a lens frame for holding an optical system and that acts as a driven and supported member. The spherical surface is supported by spherical rotators serving as supporting driving members. The lens frame is driven to rotate by means of the spherical rotators that are in contact with the lens frame, thus shifting the orientation of the optical axis of the optical system. The lens frame is rotated while being restrained from rotating about the optical axis by means of a guide ditch and a guide pin formed in the spherical surface of the lens frame. This lens frame supporting mechanism has materialized a simple supporting mechanism and a compact lens frame, and realizes a reduced load to a rotation actuator.

27 Claims, 55 Drawing Sheets

FIG.9A  FIG.9B  FIG.9C
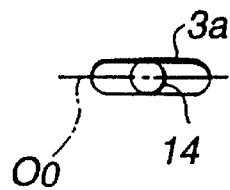
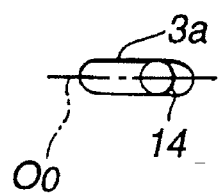
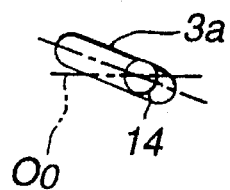
FIG.9D
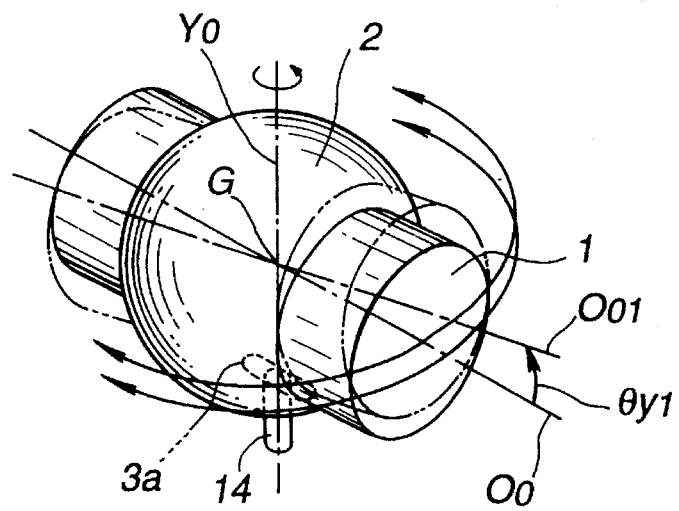
FIG.9E
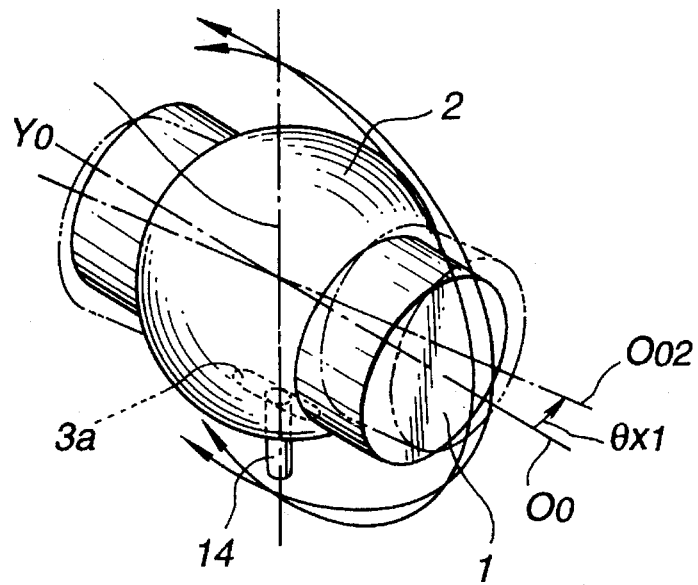

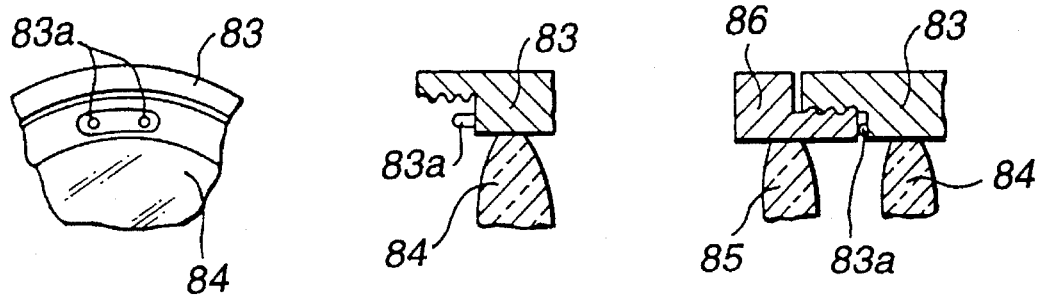
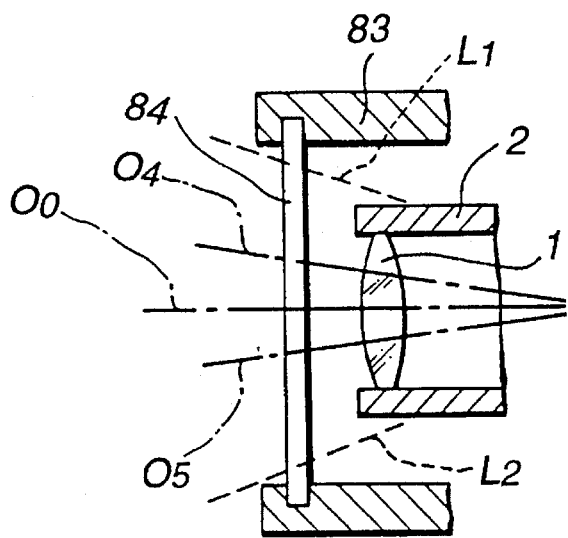
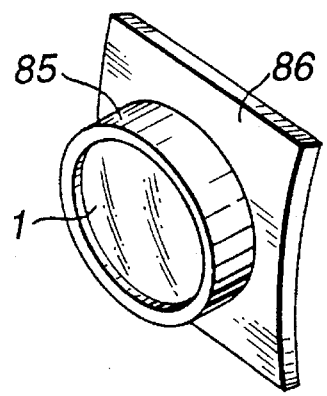

LENS FRAME SUPPORTING MECHANISM

BACKGROUND OF THE INVENTION

1. Field of the Invention

The present invention relates to a lens frame supporting mechanism, and more particularly, a lens frame supporting mechanism capable of driving a lens frame, which holds an optical system, in the direction of the optical axis of the optical system.

2. Description of the Related Art

In the past, a lens frame supporting mechanism having a so-called gimbal structure has been employed as a lens frame supporting mechanism that is usable for hand tremor compensation or lock-on control in a camera or the like, and capable of rotating a lens frame in the direction of the optical axis.

FIG. 105 is an oblique view showing a conventional lens frame supporting mechanism using the gimbal structure. A lens barrel 501 that is a lens frame is supported by a first support 502 via a support pin 501a so that the lens barrel 501 can rotate freely. The first support 502 is supported by a second support 503 via a support pin 502a so that the first support 502 can rotate freely. The second support 503 is fixed to and supported by a camera body that is not shown. The lens barrel 501 in the supporting mechanism having the above structure is held in a state in which the lens barrel 501 is disabled from rotating about an optical axis O; that is, restrained from rolling, but enabled to rotate in a vertical direction θy and a horizontal direction θx.

As for rotational drive exerted by the conventional lens frame supporting mechanism having the foregoing structure, in general, when driven by an actuator, which is not shown, mounted on the first support 502, the lens frame supporting mechanism rotates in the vertical direction θy or about the horizontal axis. When driven by an actuator, which is not shown, mounted on the second support 503 or a camera body, the lens frame supporting mechanism rotates in the horizontal direction θx, i.e. about the vertical axis.

In the aforesaid lens frame supporting mechanism, the dual structure consisting of the first and second supports 502 and 503 must be adopted as a supporting mechanism. This makes it inevitable to design a lens barrel which is large in size. Moreover, the actuator responsible for the rotational drive in the vertical rotation θy must be mounted on the first support 502. The first support 502 is supported by the second support 503. The actuator for driving the second support 503 must therefore bear a large load, leading to an increase in power consumption and in size of a lens barrel structure.

A lens frame supporting mechanism adopted for an image blur compensation mechanism, which has been disclosed in Japanese Patent Laid-Open No. 4-104666, uses the gimbal structure shown in FIG. 105. The supporting mechanism is driven bi-directionally by two moving coil actuators that are formed with two energizing coils. The moving coil actuators are installed in a camera body and associated with two magnets fixed to a back end surface 504 of a lens frame that is spherical.

The supporting mechanism shown in FIG. 105 has sway sensors 505a and 505b for detecting a sway in the vertical direction θy and a sway in the horizontal direction θx, respectively. The sway sensors 505a and 505b are supported by the lens barrel 501. When the lens frame supporting mechanism executes image blur compensation, the two moving coil actuators drive the lens barrel 501 so that the sway sensors 505a and 505b will output 0s. Thus, image blur compensation is achieved.

In the lens frame supporting mechanism adopted for the image blur compensation mechanism disclosed in the Japanese Patent Laid-Open No. 4-104666, supposing the actuators were mounted outside the supports, one of the aforesaid problems lying in the prior art; that is, a problem that load to the actuator works as a load to the lens barrel would be solved. Nevertheless, because of the supporting structure of the dual structure including the first and second supports 502 and 503, the lens barrel cannot help being designed to be large in size.

OBJECTS AND SUMMARY OF THE INVENTION

An object of the present invention is to provide a lens frame supporting mechanism that can drive and rotate the optical axis of a lens barrel, and that materializes a simple supporting mechanism and a small lens barrel, and realizes a reduced load to a rotation actuator.

A lens frame supporting mechanism according to the present invention comprises: a spherical surface that is a specified region in the outer surface of a lens frame and that covers spherical areas including at least movable zones of the lens frame; supporting driving members that are substantially in point contact with the spherical areas of the spherical surface and supporting the opposed spherical areas, and at least one of which drives the opposed spherical area, which is in contact with the supporting driving member, to rotate and displace the opposed spherical area; and a movement restrainer that restrains the lens frame from rotating about the optical axis but permits the movements in all directions except the rotation direction, and that is formed between the lens frame and another member.

In the above lens frame supporting mechanism, the supporting driving members drive the spherical surface in the specified region of the outer surface of the lens frame and thus drive and rotate the lens frame.

Other features and advantages of the present invention will be fully apparent from the description below.

BRIEF DESCRIPTION OF THE DRAWINGS

FIG. 9A shows a state of operation of the movement restrainer in the lens frame supporting mechanism of FIG. 1; that is, a reference state in which the lens frame is located at the neutral position;

FIG. 9B shows a state of operation of the movement restrainer in the lens frame supporting mechanism of FIG. 1; that is, a state in which the lens frame is rotated vertically;

FIG. 9C shows a state of operation of the movement restrainer in the lens frame supporting mechanism of FIG. 1; that is, a state in which the lens frame is rotated vertically and horizontally;

FIG. 9D is an oblique view showing a state of rotation of the lens frame in the lens frame supporting mechanism of FIG. 1;

FIG. 9E is an oblique view showing a state of rotation of the lens frame in the lens frame supporting mechanism of FIG. 1;

FIG. 27A is a front view showing an attachment lens mount for the lens barrel in the lens frame supporting mechanism of the first embodiment shown in FIG. 1;

FIG. 27B is a longitudinal sectional view showing the attachment lens mount for the lens barrel in the lens frame supporting mechanism of the first embodiment shown in FIG. 1;

FIG. 27C is a longitudinal sectional view showing a state in which the attachment lens mount is mounted on the lens frame in the lens frame supporting mechanism of the first embodiment shown in FIG. 1;

FIG. 28 shows optical paths to indicate a range of angles of view for hand tremor compensation of the lens frame in the lens frame supporting mechanism of the first embodiment shown in FIG. 1;

FIG. 29 is an oblique view showing a major portion of a lens frame with a dustproof facility for the lens frame supporting mechanism of the first embodiment shown in FIG. 1;

FIG. 95B shows the lens frame supporting mechanism of FIG. 90 in a state of operation in which the lens frame has been rotated by the first supporting driving member and changed from the state shown in FIG. 95A;

FIG. 96 is a view of FIG. 95B looking in the direction of arrow 96;

FIG. 97 is a longitudinal sectional view showing a major portion of a lens frame supporting mechanism representing a variant of the sixth embodiment shown in FIG. 90;

FIG. 98 is a longitudinal sectional view showing a major portion of a lens frame supporting mechanism representing a seventh embodiment of the present invention shown in FIG. 99 and looking in the direction of arrows 98—98';

FIG. 99 is a side view showing the major portion of the lens frame supporting mechanism in FIG. 98;

FIG. 100A is a bottom view showing the major portion of the lens frame supporting mechanism in FIG. 98 in a state of operation in which the lens frame is in a neutral state;

FIG. 100B is a bottom view showing the major portion of the lens frame supporting mechanism in FIG. 98 in a state of operation in which the lens frame is driven by a second supporting driving member;

FIG. 100C is a bottom view showing the major portion of the lens frame supporting mechanism in FIG. 98 in a state of operation in which the lens frame has been driven by a first supporting driving member and changed from the state shown in FIG. 100B;

FIG. 101 is a front view showing a major portion of a lens frame supporting mechanism representing an eighth embodiment of the present invention;

FIG. 102 is a longitudinal sectional view showing the major portion of the lens frame supporting mechanism in FIG. 101;

FIG. 103A is a plan view showing the major portion of the lens frame supporting mechanism in FIG. 101 in a state of operation in which the lens frame is in a neutral state;

FIG. 103B is a plan view showing the major portion of the lens frame supporting mechanism in FIG. 101 in a state of operation in which the lens frame is driven by a second supporting driving member;

Figure 101:
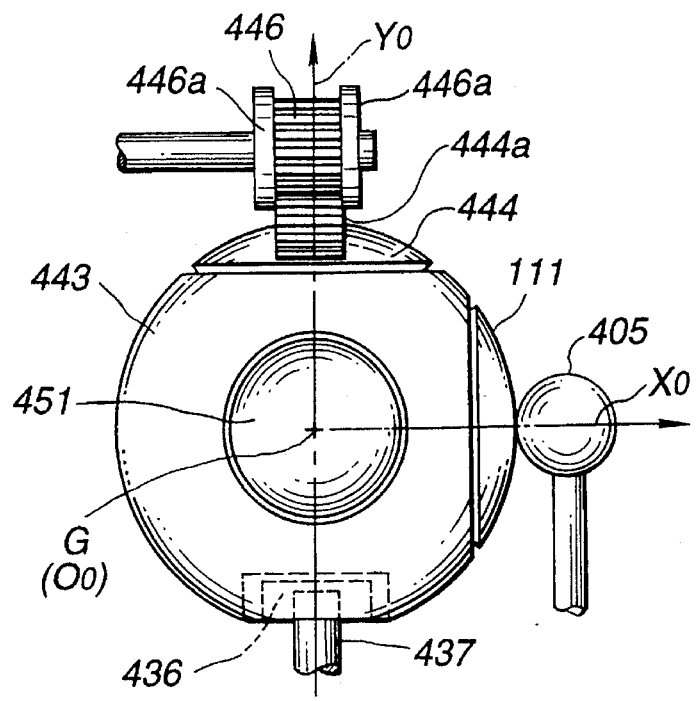
Figure 103A:
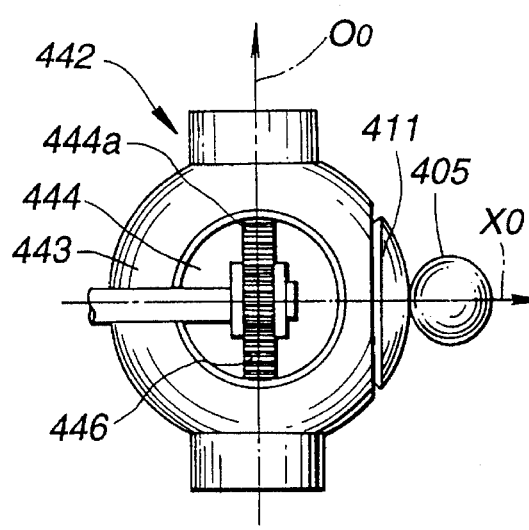
Figure 103B:
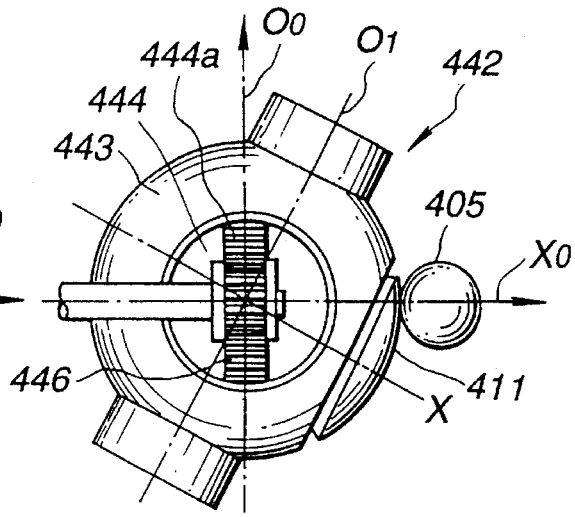
Figure 103C:
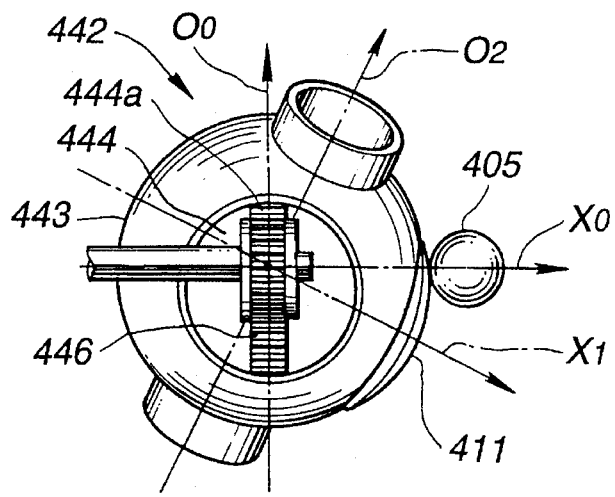
Figure 104:
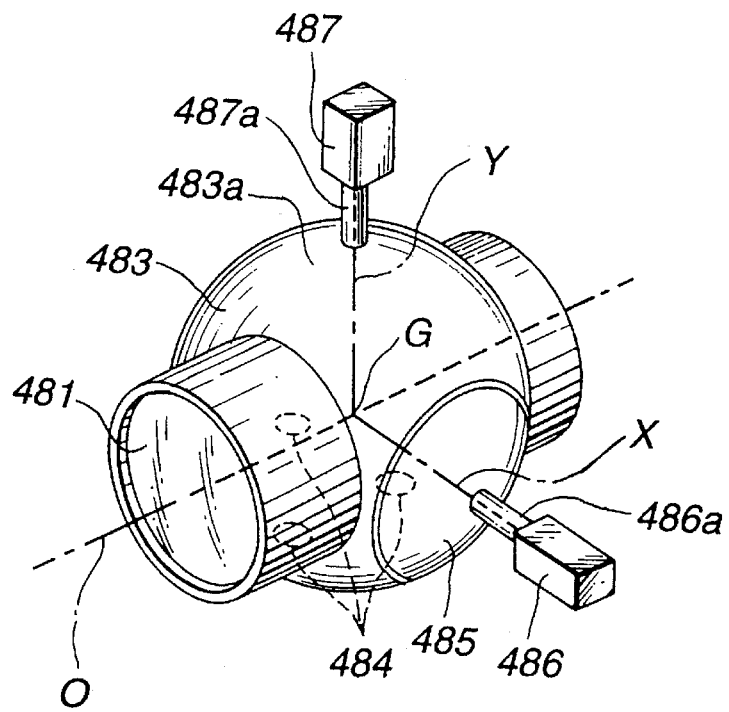
Figure 105:
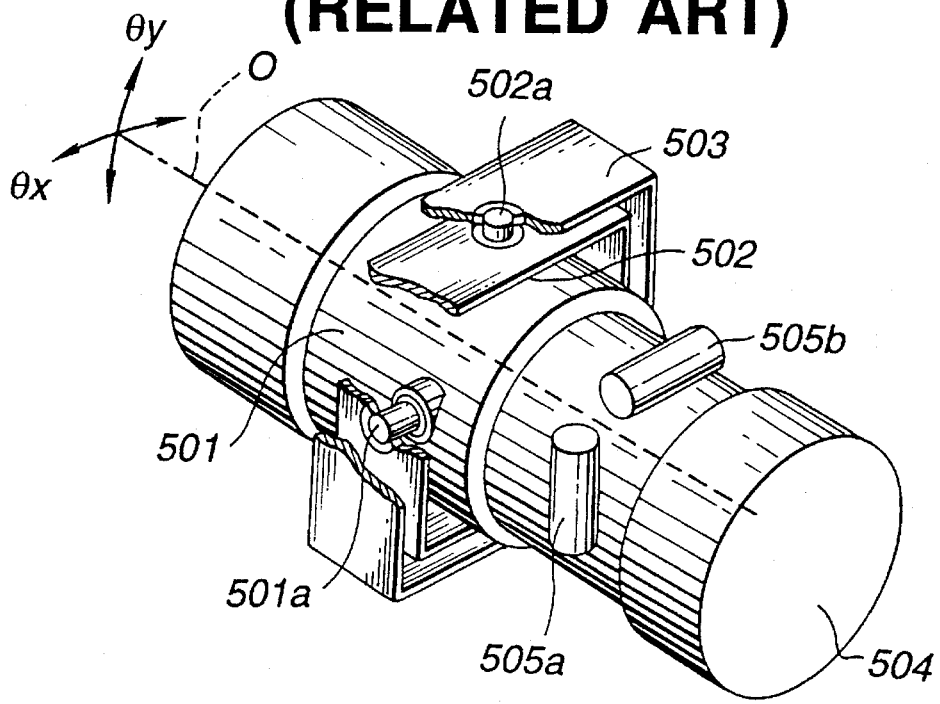

FIG. 103C is a plan view showing the major portion of the lens frame supporting mechanism in FIG. 101 in a state of operation in which the lens frame has been driven by a first supporting driving member and changed from the state shown in FIG. 103B;

FIG. 104 is an oblique view showing a major portion of a lens frame supporting mechanism representing a ninth embodiment of the present invention; and FIG. 105 is an oblique view showing a conventional lens frame supporting mechanism having a gimbal structure.

DETAILED DESCRIPTION OF THE PREFERRED EMBODIMENT

Embodiments of the present invention will be described in conjunction with the drawings.

Figure 1:
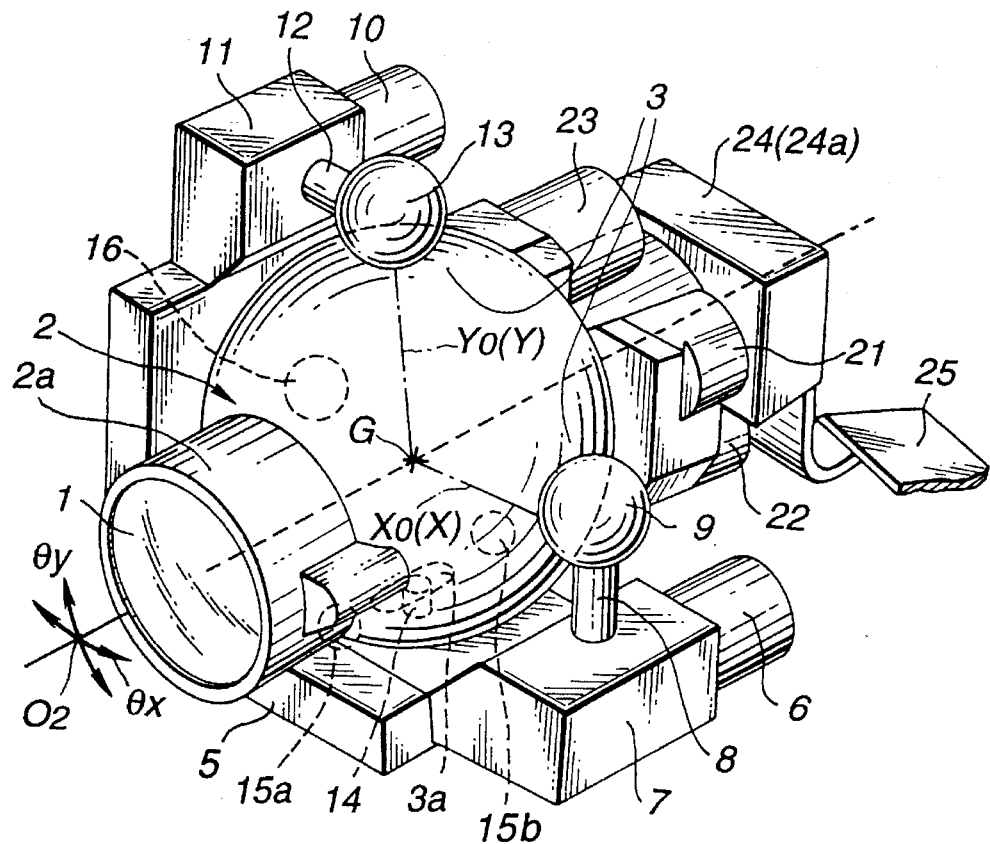
FIG. 1 is an oblique view of a lens frame supporting mechanism representing a first embodiment of the present invention.

FIG. 1 is an oblique view showing a lens frame supporting mechanism representing the first embodiment of the present invention. The lens frame supporting mechanism is applied as an optical system for a camera-inclusive VTR with a hand tremor prevention facility.

The mechanism consists mainly of a lens frame 2 that rotates about a center G, through which an optical axis O of a lens array therein passes, as a rotation center and that has a spherical surface 3, which serves as a driven and supported member, on the outer surface thereof, a base 5, which is only partially shown, to be fixed to the lens frame or a camera body, two supporting driving members that are supported by the base 5, that are substantially in point contact with the spherical surface 3, and that rotate in specified directions to displace the spherical surface 3, a movement restrainer for restraining the lens frame 2 from rotating about the optical O (the restraint is referred to as a rolling restraint), two spherical bearing members 15a and 15b that bear on the bottom of the spherical surface 3 and restrain the movement thereof along the optical axis, and a ball bearing member 16 that bears on the side surface of the spherical surface 3.

Aside from the spherical surface 3, the lens frame 2 includes a lens array 1, a lens barrel 2a for holding the lens array 1, a zoom drive unit 21, an auto-focus drive unit 22, an iris drive unit 23, a CCD unit 24 for holding an imaging device such as a CCD 24a, and a flexible printed circuit board 25 for transferring signals to or from the CCD 24a. The lens frame 2 can be driven about the rotation center G of the spherical surface 3, through which the optical O passes, while being restrained from rotating about the optical O; that is, rolling, by means of a guide pin 14 included in the movement restrainer which will be described later.

The position of the rotation center G is the position of a center of gravity of the lens frame 2 in which the above component elements are incorporated, or in the vicinity of the position of the center of gravity. A preferable rotation load is a lens frame in which the position of the center of gravity hardly changes despite zooming or the like and the moment of inertia around the center G is limited. The flexible printed circuit board 25 must be installed in a twisted manner because the CCD unit 24 rolls on the base 5 together with the lens frame 2.

One of the supporting driving members drives and rotates the spherical surface 3 of the lens frame 2 in the horizontal direction θx, and regulates the position of the spherical surface 3 along a horizontal reference axis XO. One of the supporting driving members is composed of a rotation drive motor 6, a reduction gear unit 7, a drive shaft 8, and a spherical rotator 9 that is in contact with the spherical surface 3 and whose surface is formed with a frictional member.

The other supporting driving member drives and rotates the spherical surface 3 in the vertical direction y and, regulates the position of the spherical surface 3 along a vertical reference axis YO. The other member is composed of a rotation drive motor 10, a reduction gear unit 11, a drive shaft 12, and a spherical rotator 13 that is in contact with the spherical surface 3 and whose surface is formed with a frictional member.

The movement restrainer is composed of a guide ditch 3a that is located on the bottom of the spherical surface 3 and extends in parallel with the optical O of the lens frame 2 (See FIGS. 9A, 9B, and 9C), and a cylindrical guide pin 14 that is fixed to the base 5 and fitted in the guide ditch 3a so as to slide freely therein.

When hand tremor compensation is executed, the lens frame is rotated. When the lens frame is located at a neutral position, the optical O is oriented in the direction of a reference optical axis OO. Normally, the reference optical OO is horizontal. The horizontal reference axis XO and vertical reference axis YO are therefore perpendicular to the reference optical OO.

Hand tremor compensation to be performed by the supporting mechanism having the aforesaid structure will be described briefly. A pre-sensor, which will be described later, determines whether a hand tremor occurs in the horizontal or vertical direction of the camera, and detects the magnitude of the hand tremor. The supporting driving members then rotate the lens frame 2 via the spherical surface 3 in a direction of compensating for the hand tremor. Thus, imaging is carried out in a state free from a hand tremor.

Next, the lens frame supporting mechanism of this embodiment will be described in more detail.

Figure 2:
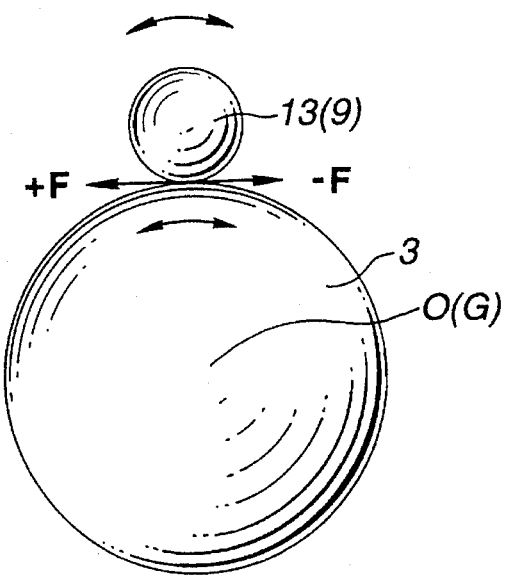
FIG. 2 is an explanatory diagram showing a state in which a spherical surface of a lens frame is driven in the lens frame supporting mechanism of FIG. 1.

FIG. 2 is an explanatory diagram for explaining a state in which the spherical rotators 9 and 13 rotate the spherical surface 3 of the lens frame 2. When the spherical rotators 9 and 13 rotate in contact with the spherical surface 3, the spherical surface 3 receives a frictional force +F or −F. This causes the lens frame 2 to rotate. When one of the spherical rotators or the spherical rotator 9 is functioning as a driving member, the other spherical rotator 13 acts as a supporting member, or vice versa.

Figure 3:
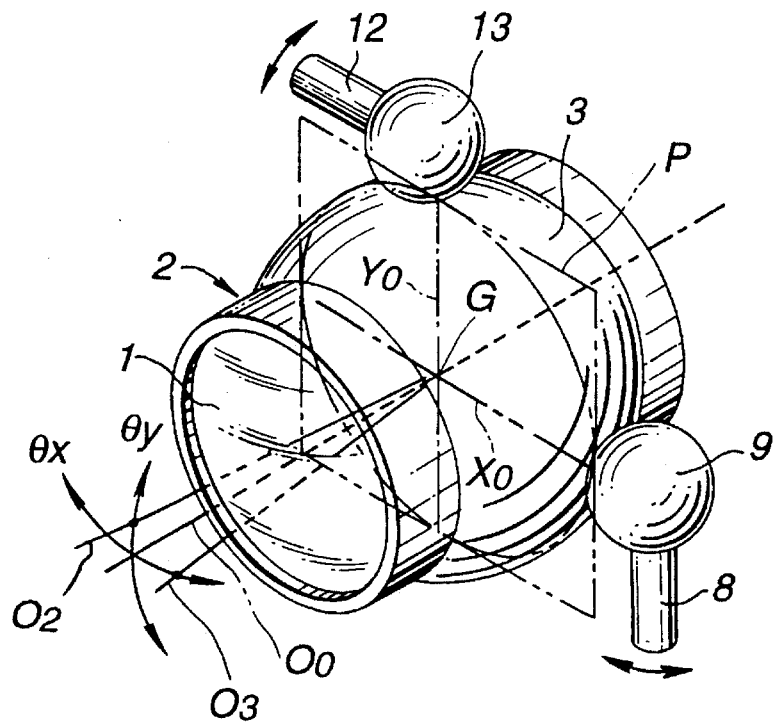
FIG. 3 is an oblique view showing a state in which the lens frame is driven with spherical rotators in the lens frame supporting mechanism of FIG. 1.
Figure 4:
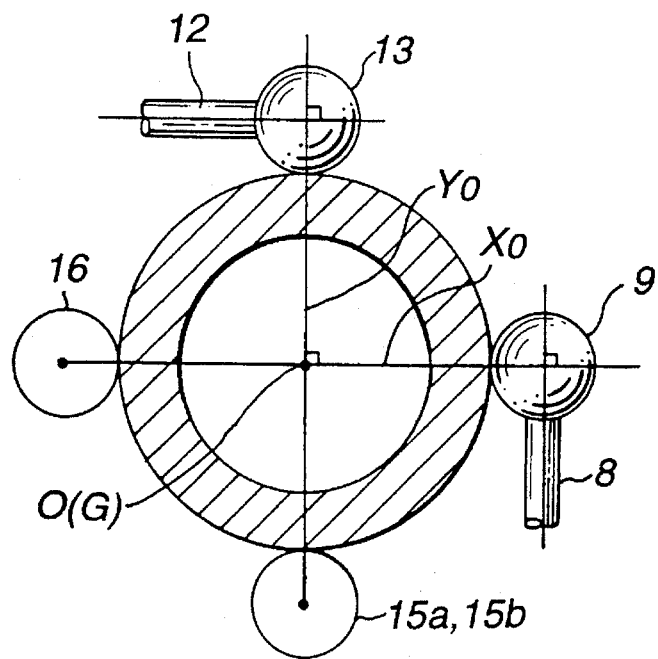
FIG. 4 is a sectional view showing a state in which the lens barrel is driven with the spherical rotator in the lens frame supporting mechanism of FIG. 1.

FIGS. 3 and 4 are oblique and sectional views respectively showing a layout of the spherical rotators 9 and 13, the drive shafts 8 and 12, and the ball bearing members 15a, 15b, and 16 relative to the spherical surface 3. Herein, P denotes a plane perpendicular to the reference optical OO for rotation. The horizontal and vertical reference axes XO and YO lie on the plane P.

As described previously, the longitudinal direction of the guide ditch 3a provided for rolling restraint is elongated in a direction parallel with the optical O. When restrained from rolling, the lens frame 2 is driven so that the optical axis O will shift by an angle of horizontal rotation θx and an angle of vertical rotation By, which are values within specified ranges, from the direction of the reference optical OO or a neutral direction to the directions of optical O3 and O2.

The contact point of the spherical rotator 9 or 13 relative to the spherical surface 3 must be present on the plane P perpendicular to the optical axis OO in order to reduce the possibility that the lens frame 2 slips at the contact portion and to improve the transmission efficiency of the driving force. However, the spherical rotator 9 or 13 should preferably be in point contact with the spherical surface 3 for better transmission of their driving force.

For simpler computation of an after-rotation position, which is required for improving the transmission efficiency of driving force and achieving hand tremor compensation, the locations of the contact points of the spherical rotators 9 and 13 relative to the spherical surface 3 and the orientations of the drive shafts 8 and 12 of the spherical rotators should preferably be specified as described below.

That is to say, the contact points of the spherical rotators 9 and 13 are located on the reference axes XO and YO. The drive shafts 8 and 12 are oriented in directions perpendicular to the reference axes XO and YO.

When the spherical rotators 9 and 13, and drive shafts 8 and 12 are arranged as mentioned above, even if the lens frame 2 is driven to rotate so that the optical O thereof will change the orientation from the direction of the reference optical OO to the direction of the optical axis O2, O3, or a composite axis thereof, since the movable direction of the spherical surface 3 is substantially consistent with the directions +F and −F in which the spherical rotators 9 and 13 are constrained to drive at the contact points thereof, drive is achieved with the least slip or least loss.

The contact points of the spherical rotators 9 and 13 relative to the spherical surface 3 are not necessarily the aforesaid ones. Even when the contact points are located at any other positions, rotation drive for the lens frame 3 can be achieved. Nevertheless, from the viewpoints of the transmission efficiency of driving force and the electrical size of a load to a motor, it is preferred that the contact positions thereof are located at the aforesaid positions.

Figure 5:
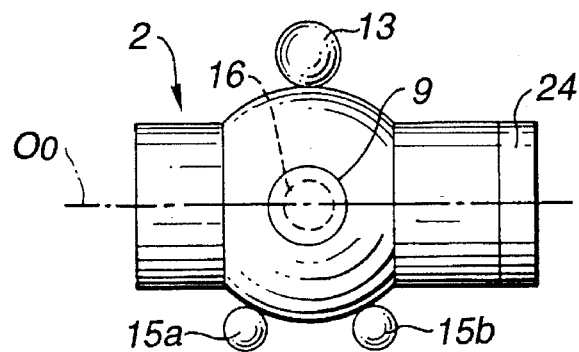
FIG. 5 is a side view showing a state in which the lens frame is supported in the lens frame supporting mechanism of FIG. 1.

As shown in FIG. 4 or 5, the spherical rotator 13 is opposed to the two ball bearing members 15a and 15b, and the spherical rotator 9 is opposed to the ball bearing member 16. The spherical rotator 13 therefore works as a supporting member for the spherical surface 3, and holds the spherical surface 3 so that the spherical surface 3 can rotate about the rotation center G with precision but less resistance. The bearing members 15a and 15b, or 16 may be located not only on the opposite side of the spherical rotator 9 or 13 but also at a position at which the lens frame can be held at a specified position.

Figure 6A:
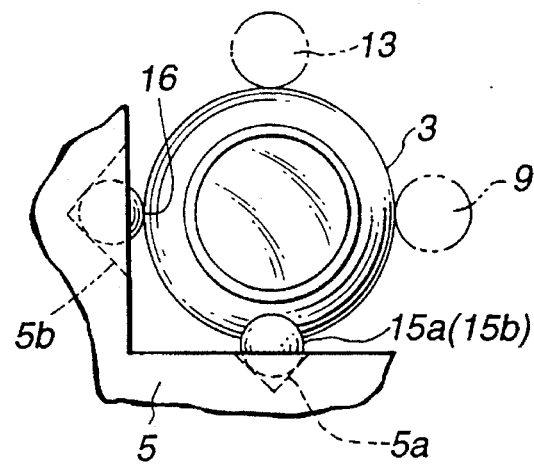
FIG. 6A is a front view showing a state in which the lens frame is supported in the lens frame supporting mechanism of FIG. 1.
Figure 6B:
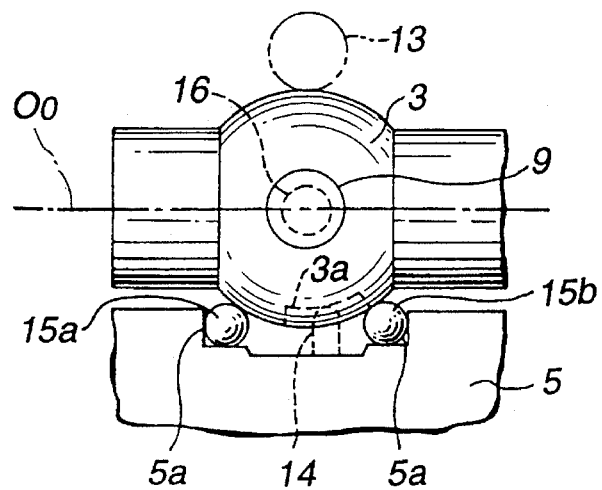
FIG. 6B is a side view showing a state in which the lens frame is supported in the lens frame supporting mechanism of FIG. 1.

In FIGS. 6A and 6B, the ball bearing members 15a, 15b, and 16 are attached to the base 5. FIG. 6A is a front view showing the members attached to the base. FIG. 6B is a longitudinal sectional view showing the members attached to the base. As illustrated, the ball bearing members 15a, 15b, and 16 are held in conical ditches 5a and 5b formed in the base 5 so that they can rotate freely.

Figure 7A:
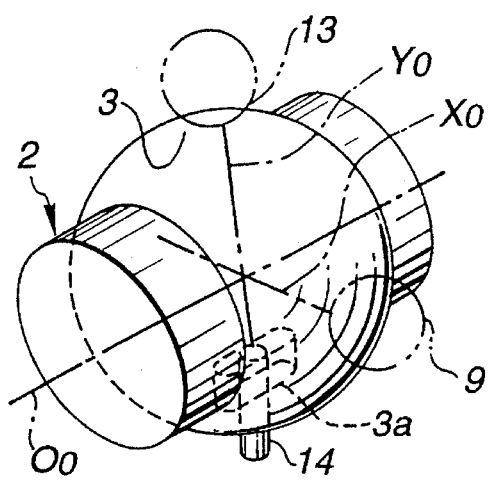
FIG. 7A is a perspective view showing a state in which the lens frame is guided by a movement restrainer in the lens frame supporting mechanism of FIG. 1.
Figure 7B:
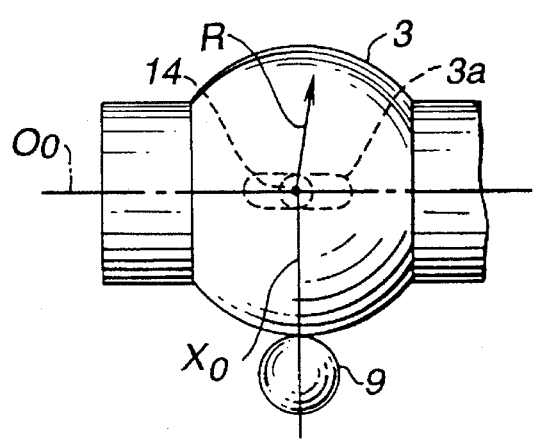
FIG. 7B is a plan view showing a state in which the lens frame is guided by the movement restrainer in the lens frame supporting mechanism of FIG. 1.

In FIGS. 7A and 7B, the lens frame 2 is supported by the guide pin 14 constituting the movement restrainer so that the lens frame 2 can be driven freely. FIG. 7A is a perspective view, while FIG. 7B is a plan view. The guide pin 14 is located on the bottom of the spherical surface 3 and fitted longitudinally in the guide ditch 3a extending in parallel with the optical O. The backlash of the fitted portion of the guide pin 14 should be as small as possible. A backlash removing mechanism may be added.

The axis of the guide pin 14 is aligned with the reference axis YO that is parallel with the vertical axis. When the spherical rotator 9 is actuated to rotate by a radius R, the lens frame is driven to rotate in the horizontal direction (θx) about the YO axis. Under the condition that the spherical rotators 9 and 13 are in point contact with the spherical surface, when the spherical rotator 9 is actuated for drive, the spherical rotator 9 neither slips at the driving contact point thereof nor causes the spherical rotator 13 to slip at the contact point. Drive is therefore achieved efficiently.

Figure 8A:
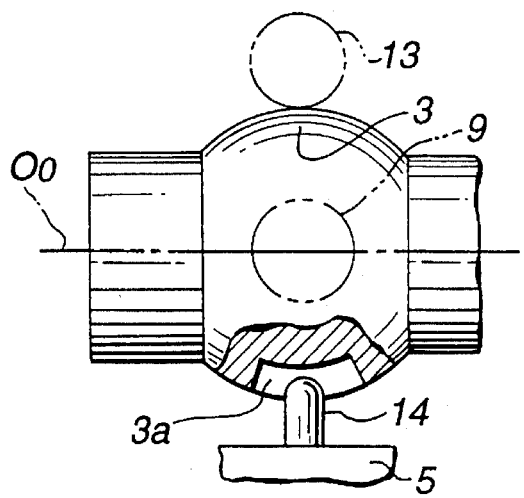
FIG. 8A is a side view showing a state in which the lens frame is guided by the movement restrainer in the lens frame supporting mechanism of FIG. 1 and located at a neutral position or a reference rotary position.
Figure 8B:
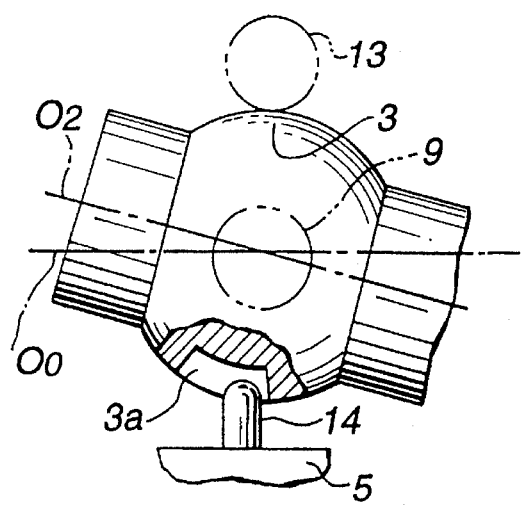
FIG. 8B is a side view showing a state in which the lens frame is guided by the movement restrainer in the lens frame supporting mechanism of FIG. 1 and rotated vertically.

FIGS. 8A and 8B are side views showing states of rotation of the lens frame 2. In FIG. 8A, the lens frame 2 is located at a reference position oriented in the direction of the optical OO. The guide pin 14 is fitted in the guide ditch 3a. In this state of drive, provided that the lens frame 2 is not rotated horizontally, when the spherical rotator 13 is actuated for drive, the spherical rotator 13 neither slips at the driving contact point thereof nor causes the spherical rotator 9 to slip at the contact point thereof. Drive is therefore achieved efficiently.

FIGS. 9A, 9B, and 9C are plan views showing the states of movement of the movement restrainer associated with the states of rotation of the lens frame 2; that is, the positional relationships between the guide ditch 3a and guide pin 14, which constitute the movement restrainer. The state in FIG. 9A corresponds to the reference state in FIG. 8A. The state in FIG. 9B corresponds to the state of vertical rotation in FIG. 8B. FIG. 9C shows a state in which the lens frame 2 has rotated in the vertical direction (θy) and horizontal direction (θx). In this state, the orientation of the guide ditch is inconsistent with the direction of the reference optical OO. When the spherical rotator 13 is actuated for drive, the spherical rotator 13 slips at the driving contact point thereof and causes the spherical rotator 9 to slip at the contact point thereof. However, since a rotation range for hand tremor compensation is limited, driving efficiency will not deteriorate.

In the aforesaid lens frame supporting mechanism of this embodiment, the movement restrainer restrains the lens frame 2 from rolling when the lens frame 2 is rotated. FIGS. 9D and 9E are oblique views showing the states of rotation of the lens frame 2 on which rolling restraint is imposed. In FIG. 9D, the lens frame 2 is rotated by an angle θy1 vertically, and then rotated horizontally. Assuming a globe is imagined, the globe is rotated in the latitudinal direction. In FIG. 9e, the lens frame 2 is rotated by an angle θx1 horizontally, and then rotated vertically. When it comes to the globe, the globe is rotated in the longitudinal direction. In the states shown in FIGS. 9D and 9E, the lens frame 2 rotates as a state controlled by the guide pin 14.

Figure 9F:
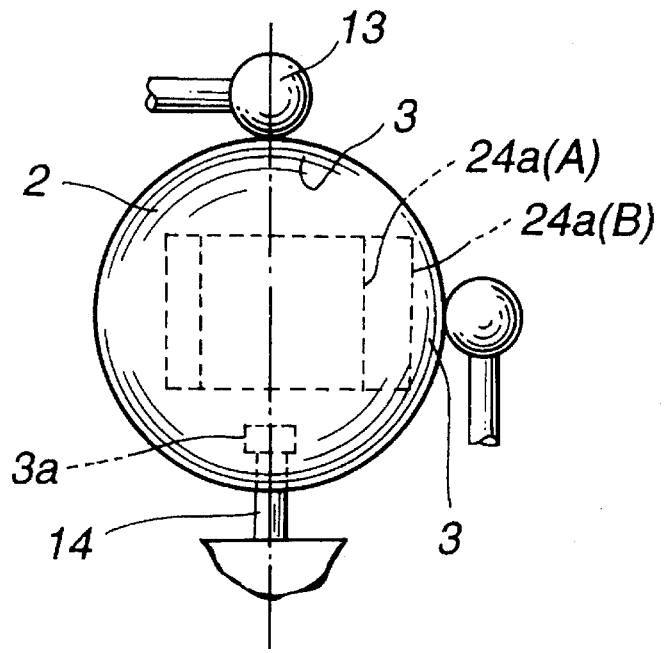
FIG. 9F shows a state of movement of a CCD resulting from the horizontal movement of the lens frame in the lens frame supporting mechanism of FIG. 1.

When the lens frame 2 rotates horizontally as shown in FIG. 9D, the CCD 24a incorporated in the CCD unit 24 held by the lens frame 2 moves from a position 24a(A) to a position 24a(B) in FIG. 9F. The movement is made in a direction perpendicular to the orientation of the guide pin 14 in the movement restrainer. The direction of movement can therefore be consistent with the direction of horizontal scan performed to fetch an image signal from the CCD 24a. Image data can therefore be acquired under a preferred condition.

Figure 9G:
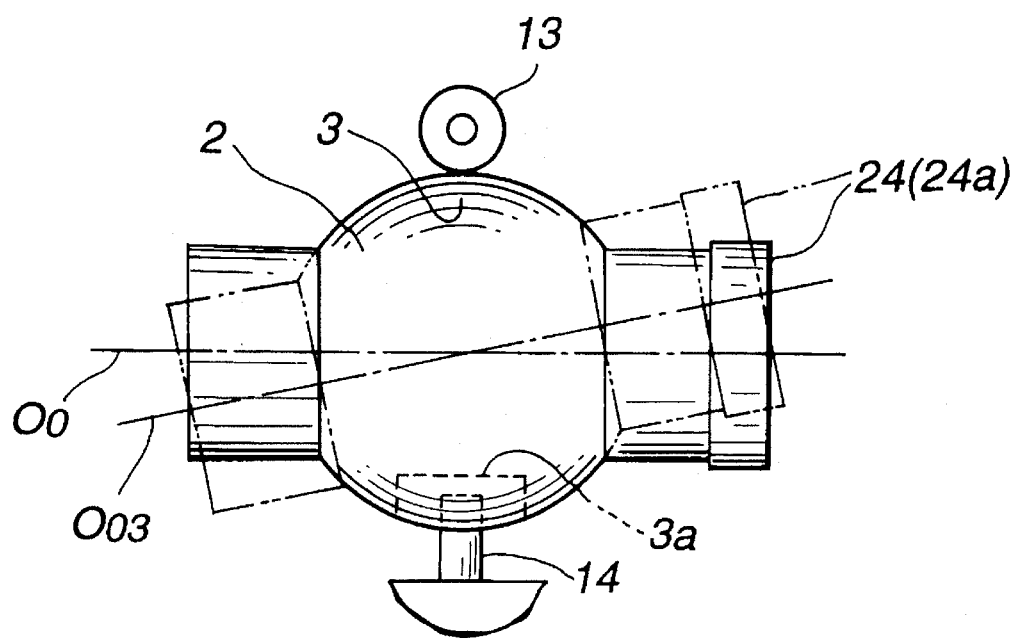
FIG. 9G shows a state of movement of the CCD resulting from the vertical movement of the lens frame in the lens frame supporting mechanism of FIG. 1.

When the lens frame 2 rotates vertically as shown in FIG. 9D, the CCD 24a moves without changing the position as shown in FIG. 9G. Image data can therefore be acquired under a preferred condition.

In this embodiment, the guide ditch 3a of the movement restrainer is formed on an extension of the YO axis or the vertical reference axis. The ditch may be formed on an extension of the XO axis or horizontal reference axis. In this case, X-axis drive results in a latitudinal rotation, and Y-axis drive results in a longitudinal rotation.

Figure 10:
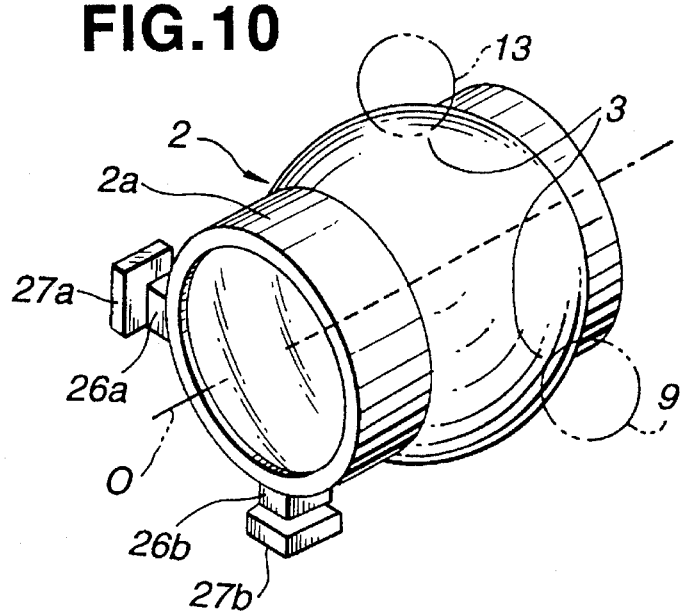
FIG. 10 is an oblique view showing a state of installation of magnetic sensors for rotation angle detection in the lens frame supporting mechanism of FIG. 1.

FIG. 10 is an oblique view showing magnetic sensors for detecting angles of rotation (θx and θy) by which the lens frame 2 is driven to rotate in order to compensate for a hand tremor. Magnets 26a and 26b are fixed to a distal part of the lens barrel 2a. A Hall element 27a for detecting an angle of rotation θx and a Hall element 27b for detecting an angle of rotation θy are supported by the base 5 (see FIG. 1), so that they will be associated with the magnets 26a and 26b. The output values of the Hall elements 27a and 27b are calculated to detect angles of rotation of the lens frame 2. This ensures precise hand tremor compensation.

Figure 11:
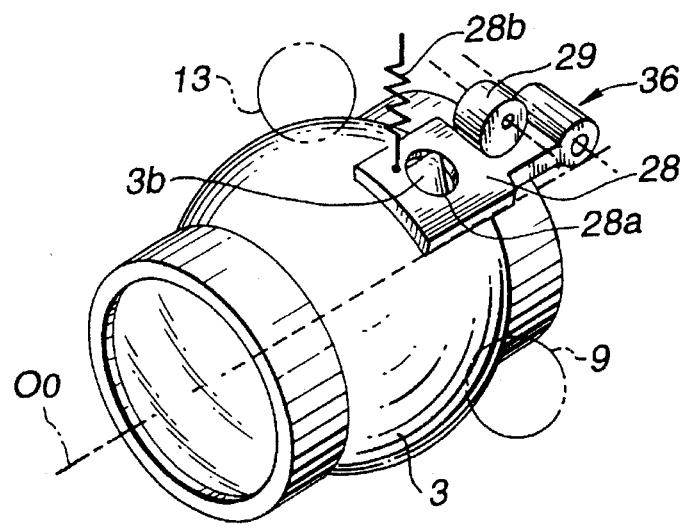
FIG. 11 is an oblique view showing a state of installation of a locking mechanism in the lens frame in the lens frame supporting mechanism of FIG. 1.

FIG. 11 is an oblique view showing a locking mechanism that, when hand tremor compensation is inactivated, is actuated to fix the direction of the optical axis of the lens frame 2 to the direction of the reference axis OO precisely. In the locking mechanism 36, a conical projection 3b is formed on the spherical surface 3 of the lens frame 2, and a lock member 28 having a hole 28a, into which the projection 3b is fitted, is placed on the spherical surface 3 with the lock member 28 supported axially by the base 5 (see FIG. 1). The lock member 28 is constrained toward separating from the projection 3b by means of a spring 28b. For locking the lens frame 2, a lock cam 29 axially supported by the base 5 (see FIG. 1) is used to turn the lock member 28 against the spring 28b so that the projection 3b will be fitted in the hole 28a of the lock member 28. The lock cam 29 is actuated by a lock motor which is not shown.

Figure 12A:
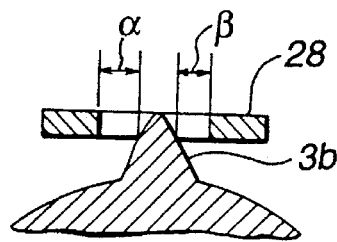
FIG. 12A shows a state of operation of the locking mechanism in FIG. 11 or a state in which the lens frame is unlocked.
Figure 12B:
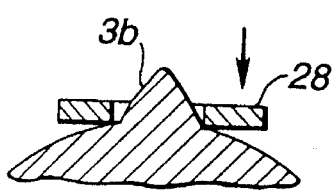
FIG. 12B shows a state of operation of the locking mechanism in FIG. 11 or a state in which the lens frame is locked.

FIG. 12A is a sectional view of the locking mechanism. The lock member 28 is separated from the projection 3b. The lens frame 2 is movable for hand tremor compensation. In FIG. 12B, the lock member 28 has been turned by the lock cam 29 and the projection 3b is fitted in the hole 28a. In this state, the lens frame 2 is immobilized and oriented in the direction of the reference rotation OO.

Figure 13:
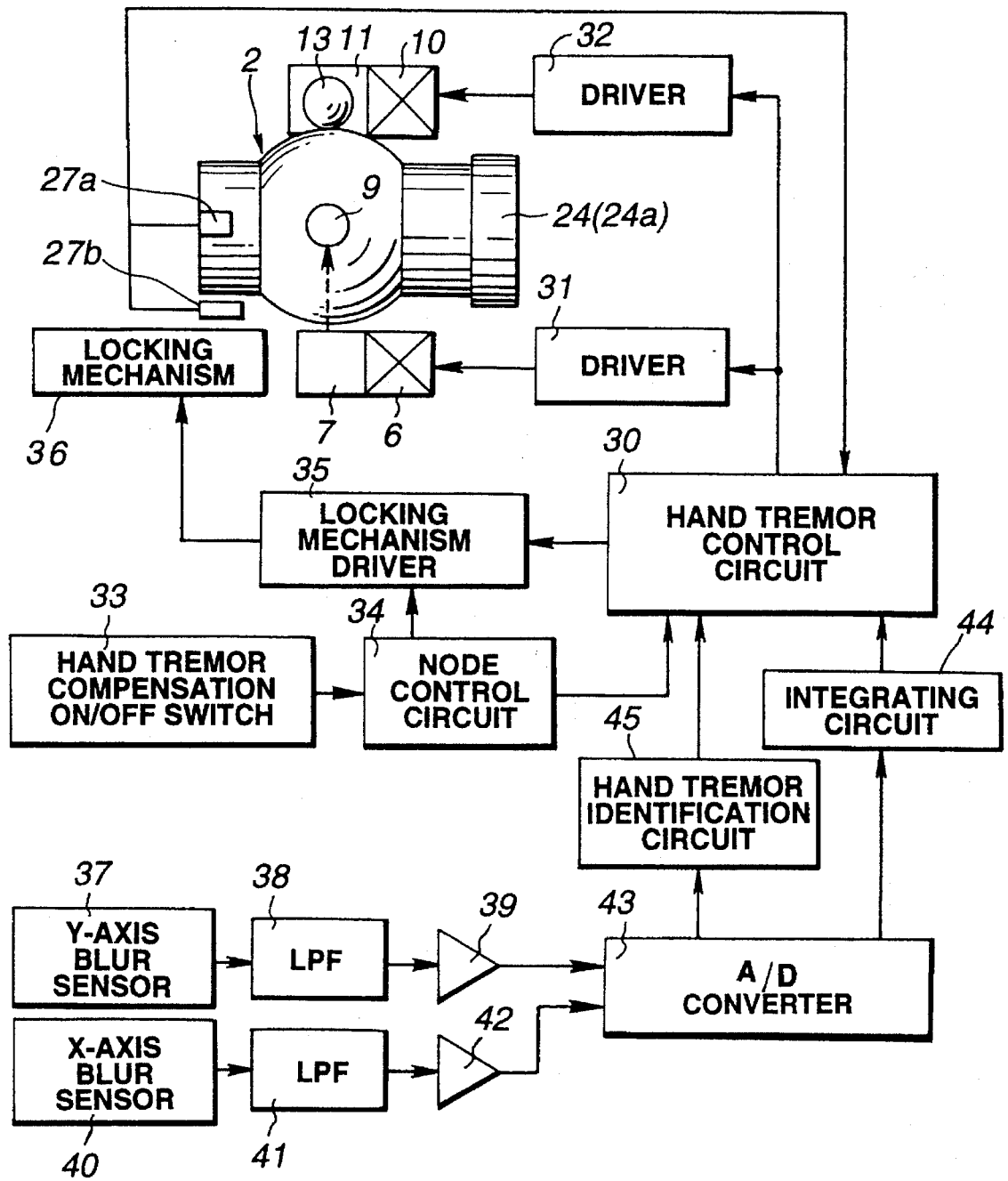
FIG. 13 is a block diagram of a hand tremor compensation control unit using the lens frame supporting mechanism of FIG. 1.

FIG. 13 is a block diagram of a hand tremor compensation control unit using the lens frame supporting mechanism of the first embodiment. This control unit comprises a hand tremor compensation control circuit 30 for controlling rotation drive for a lens frame according to a hand tremor detection signal, a hand tremor compensation designating unit, a hand tremor detector, and a lens frame.

The hand tremor compensation designating unit comprises a hand tremor compensation on/off switch 33 for use in designating execution of hand tremor compensation, a mode control circuit 34 that outputs a lock signal to a locking mechanism driver 35, which will be described later, according to the output of the switch 33, the locking mechanism driver 35 for driving the lock motor for the locking mechanism 36 according to the output of the mode control circuit 34, and the locking mechanism 36 that includes the lock motor and locks the lens frame 2.

The hand tremor detector comprises an X-axis blur sensor 37 and a Y-axis blur sensor 40 which are rotating speed sensors, low-pass filters 38 and 41 for removing high-frequency components from the output signals of the sensors, amplifiers 39 and 42, and A/D converter 43 for converting the output signals of the amplifiers into digital signals, a hand tremor identification circuit 45 that determines whether the blur detected in the output signal of the A/D converter results from a hand tremor and that outputs a signal to the hand tremor compensation control circuit 30, and an integrating circuit 44 that integrates the output signal of the A/D converter to calculate a magnitude of displacement caused by a hand tremor, and outputs the magnitude to the hand tremor compensation control circuit 30. Acceleration sensors may be employed as the blur sensors 37 and 40.

The lens frame comprises a body including a lens frame drive mechanism described in conjunction with FIG. 1 and other figures, and drivers 31 and 32 for driving rotation drive motors 6 and 10 in the lens frame driving mechanism.

The control procedure followed by the hand tremor compensation control unit having the aforesaid configuration will now be described. First, the output of the hand tremor compensation on/off switch 33 is checked to determine whether hand tremor compensation has been designated. When it is determined that the hand tremor compensation is not designated, the lock cam 29 of the locking mechanism 36 is turned. Thus, the projection 3b on the spherical surface 3 is fitted in the hole 28a of the lock member 28, whereby the lens frame 2 is locked.

When it is determined that hand tremor compensation has been designated, X- and Y- axis blur detection signals are fetched. The identification circuit 45 then determines whether the motion of the camera is derived from a hand tremor. If it is determined that a hand tremor has occurred, the integrating circuit 44 integrates the X- and Y- axis blur detection signals to calculate a magnitude of the hand tremor. A magnitude of compensation corresponding to the magnitude of the hand tremor is then computed. The hand tremor compensation control circuit 30 then drives the rotation drive motors 6 and 10 in the lens frame drive mechanism by the computed magnitude of compensation using the drivers 31 and 32. The lens frame 2 is thus rotated horizontally and/or vertically. The hand tremor control circuit 30 fetches the after-rotation position signals of the lens frame 2 via the Hall elements 27a and 27b. The lens frame 2 is thus driven to rotate by the magnitude of compensation.

As described above, the lens frame drive mechanism of this embodiment eliminates the conventional dual structure or the gimbal structure. The spherical surface 3 of the lens frame can be supported or driven directly. The structure is simple, the driving systems are concise, and the lens frame is compact. The spherical rotators 9 and 13 act not only as driving members but also as supporting members, which leads to the concise supporting and driving mechanism for the lens frame. Furthermore, the lens frame 2 is driven to rotate with the optical O thereof as a center. The extension of the guide ditch 3a, for restraining the lens frame 2 from rolling, is parallel with the optical O. The contact points of the spherical rotators 9 and 13 serving as frictional driving members are set on a plane perpendicular to the reference axis OO. This mechanical design results in a lens frame drive mechanism causing few slips at the time of driving and offering excellent driving efficiency.

Figures 14A, 14B, 14C:
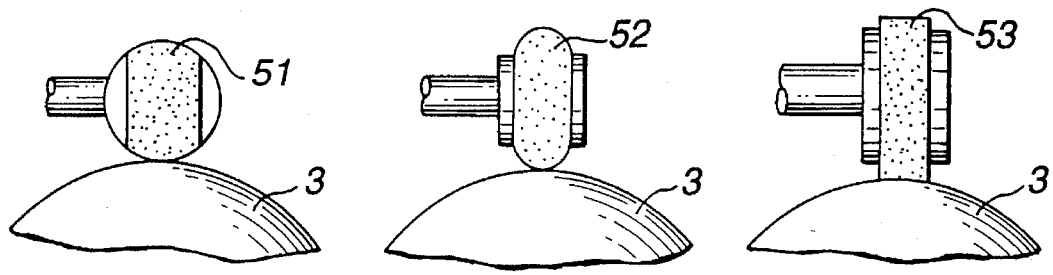
FIG. 14A shows a variant of the spherical rotator for the lens frame supporting mechanism of the first embodiment shown in FIG. 1; that is, a spherical rotator formed with an elastic member.
FIG. 14B shows another variant of the spherical rotator for the lens frame supporting mechanism of the first embodiment shown in FIG. 1 that is, a doughnut-shaped spherical rotator formed with an elastic member.
FIG. 14C shows another variant of the spherical rotator for the lens frame supporting mechanism of the first embodiment shown in FIG. 1; that is, an annular rotator formed with an elastic member.

FIGS. 14A, 14B, and 14C show states of working of variants of the spherical rotator serving as a supporting driving member for the lens frame supporting mechanism of the first embodiment.

In FIG. 14A, the supporting driving member is a spherical elastic supporting drive. A supporting drive 51 of this variant has a surface made of a raw material having a high coefficient of friction, and which can be deformed elastically.

In another variant shown in FIG. 14B, the supporting driving member is a doughnut-shaped elastic supporting drive. A supporting drive 52 of this variant has a surface showing a high coefficient of friction, and which can be deformed elastically.

In yet another variant shown in FIG. 14C, the supporting driving member is an annular elastic supporting drive. A supporting drive 53 of this variant has a surface showing a high coefficient of friction, and which can be deformed elastically.

Any of the aforesaid variants exerts stable force on the spherical surface 3 and hardly slips when driven. This results in improved driving efficiency.

Figure 15:
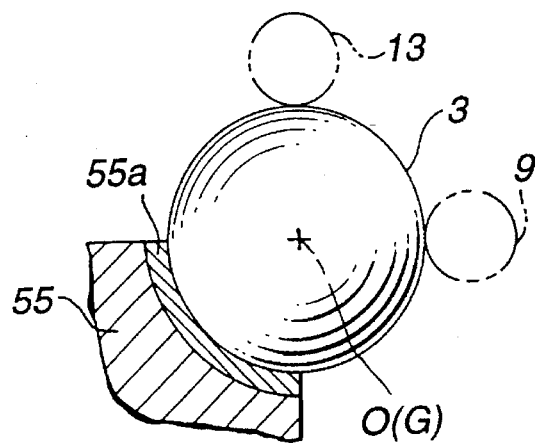
FIG. 15 is a sectional view showing a variant of a bearing member for the lens frame supporting mechanism of the first embodiment shown in FIG. 1; that is, a bearing member made of a solid lubricant material.

FIG. 15 shows the state of working of a bearing member 55a that is a variant of the bearing member of the spherical surface 3 of the lens frame in the lens frame supporting mechanism of the first embodiment. In this variant, the bearing member 55a is made of a solid lubricant whose curvature agrees with that of the spherical surface 3. The bearing member 55a is fixed to the base 5. This variant offers limited slide resistance and requires a minimized torque for rotational drive of the lens frame.

Figure 16:
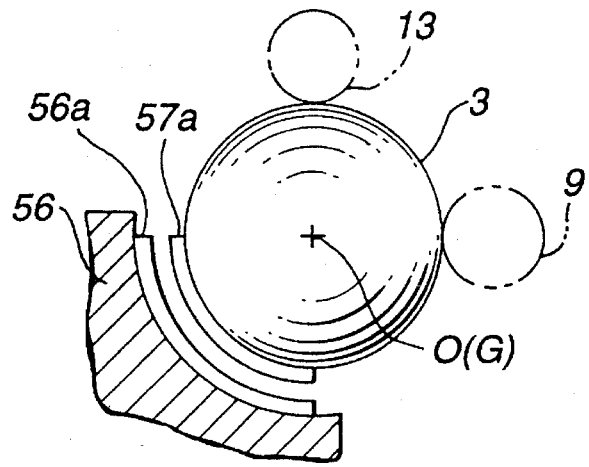
FIG. 16 is a sectional view showing another variant of the bearing member for the lens frame supporting mechanism of the first embodiment shown in FIG. 1; that is, a bearing member formed with a magnet.

FIG. 16 shows the state of working of a bearing member 56a that is a variant of the bearing member for the spherical surface 3 of the lens frame in the lens frame supporting mechanism of the first embodiment. In this variant, a magnet 57a curved to conform with the spherical surface 3 is fixed to the spherical surface 3. A magnet 56a is fixed to the base 56 in such a manner that the magnet 56a will be opposed to the magnet 57a. The mutually-opposed surfaces of the magnets 57a and 56a have the same polarity. The repulsion occurring between the magnets is used to hold the lens frame 2. According to this variant, the frictional resistance caused by the bearing member is quite small.

Figure 17:
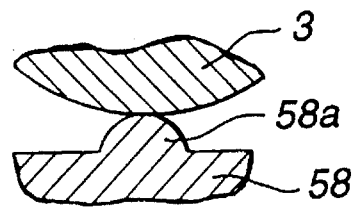
FIG. 17 is a sectional view showing another variant of the bearing member for the lens frame supporting mechanism of the first embodiment shown in FIG. 1; that is a bearing member united with a base.

FIG. 17 shows the state of working of a bearing member 58a that is yet another variant of the spherical bearing member for the spherical surface 3 of the lens frame in the lens frame supporting mechanism of the first embodiment. In this variant, the bearing 58a is formed as part of the base 58. This variant contributes to reduction in the number of parts and simplification of the structure.

Figure 18:
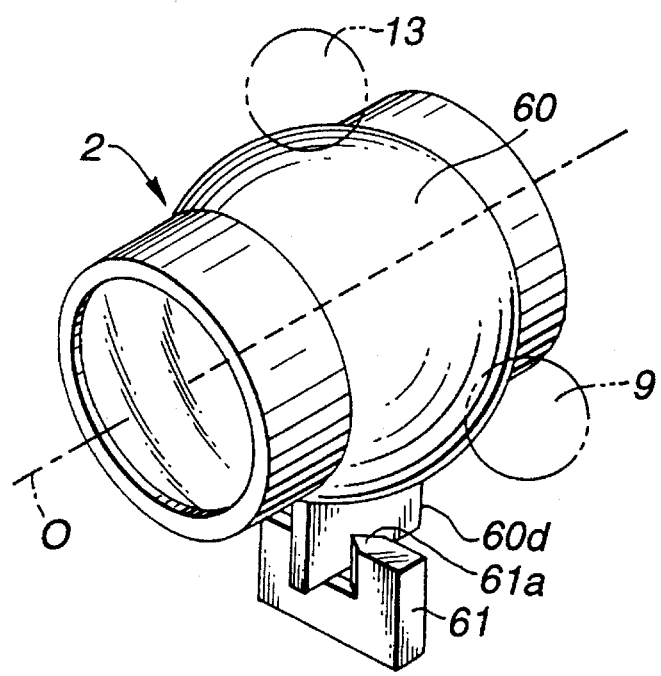
FIG. 18 is an oblique view showing a variant of the movement restrainer for the lens frame supporting mechanism of the first embodiment shown in FIG. 1; that is, a movement restrainer comprising a fin and a fin guide.

FIG. 18 is an oblique view showing a variant of the movement restrainer which is designed to restrain the lens frame from rolling or rotating about the optical axis, for the lens frame in the lens frame supporting mechanism. The movement restrainer in the first embodiment is composed of a guide pin and a guide ditch, while the restrainer in this variant is composed of a fin and a fin guide.

In this embodiment, a fin 60d is attached to the bottom of the spherical surface 3 and is aligned in parallel with the optical O of the lens frame 2. A fin guide 61, in which the fin 60d is fitted to slide freely, is fixed to the base.

Figure 19:
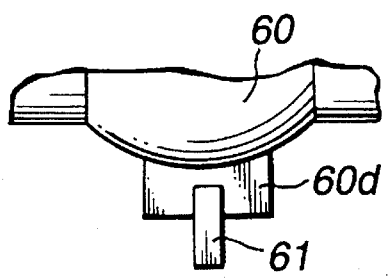
FIG. 19A is a side view showing a state of operation of the movement restrainer shown in FIG. 18; that is, a reference state in which the lens frame is located at the neutral position.
FIG. 19B is a side view showing a state of operation of the movement restrainer of FIG. 18; that is, a state in which the lens frame is rotated vertically.
Figure 19:
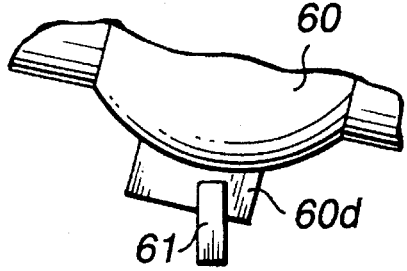

FIGS. 19A and 19B are side views showing the states of operation of the movement restrainer of the above variant. In FIG. 19A, the lens frame 2 is located at the reference position for rotation. In FIG. 19B, the lens frame 2 has been rotated vertically.

Figures 20A, 20B, 20C:
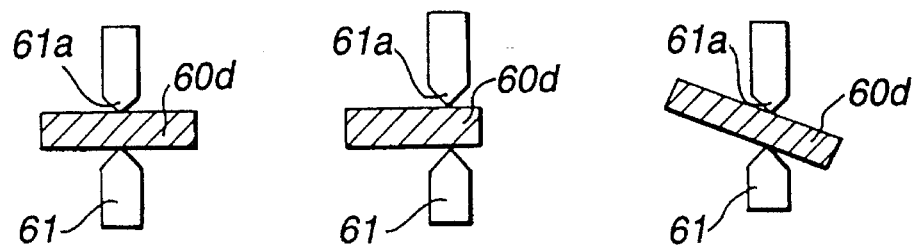
FIG. 20A is a plan view showing a state of operation of the movement restrainer of FIG. 18; that is, a reference state in which the lens frame is located at the neutral position.
FIG. 20B is a plan view showing a state of operation of the movement restrainer of FIG. 18; that is, a state in which the lens frame is rotated vertically.
FIG. 20C is a plan view showing a state of operation of the movement restrainer of FIG. 18; that is, a state in which the lens frame is rotated horizontally.

FIGS. 20A, 20B, and 20C are horizontal sectional views showing the states of operation of the movement restrainer of the above variant. In FIG. 20A, the lens frame 2 is located at the reference position in readiness for rotation. In FIG. 20B, the lens frame 2 has been rotated vertically to cause the fin 60d to slide to the extreme end thereof. In FIG. 20C, the lens frame 2 has been rotated horizontally to cause the fin 60d to tilt.

Figure 21A:
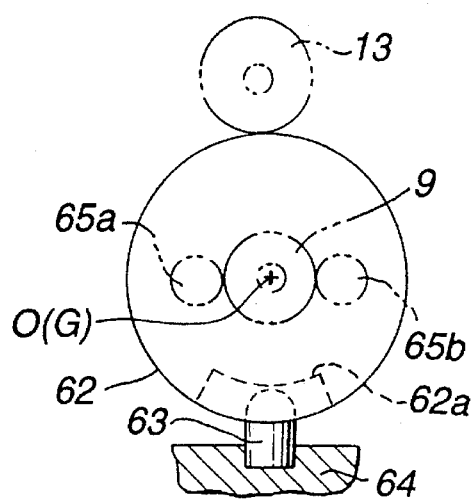
FIG. 21A is a side view showing another variant of the movement restrainer for the lens frame supporting mechanism of the first embodiment shown in FIG. 1.
Figure 21B:
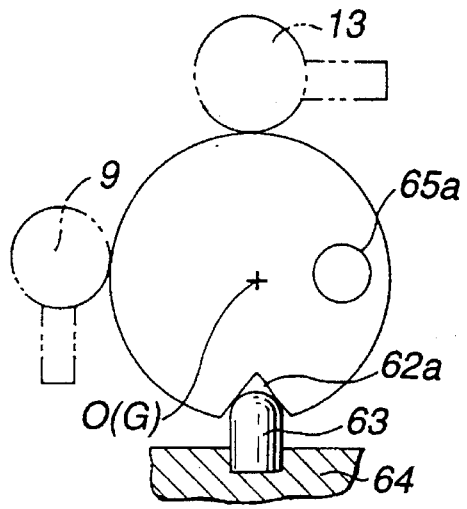
FIG. 21B is a front view showing a variant of the movement restrainer in FIG. 21A.

FIGS. 21A and 21B show a restraining unit composed of a V-shaped ditch and a guide pin having a spherical tip; that is, another variant of the movement restrainer for the lens frame in the lens frame supporting mechanism of the first embodiment. FIG. 21A is a side view, while FIG. 21B is a front view. In this variant, a V-shaped ditch 62a is formed in the bottom of a spherical surface 62 of a lens frame in parallel with the optical O of the lens frame. A guide pin 63 having a spherical tip is fixed to a base 64. The guide pin 63 is fitted into the V-shaped ditch 62a, thus restraining the spherical surface 62 from rolling. In this embodiment, the guide pin 63 is fitted into the V-shaped ditch 62a. No backlash therefore occurs in the movement restrainer. In this variant, two spherical bearing members 65a and 65b must be attached to the lateral part of the spherical surface 62 in order to regulate the position of the lens frame in the direction of the optical axis.

When the guide pin 14 or 63 of the movement restrainer for the lens frame in the embodiment or variant is rotated about the optical axis, a variant of a mechanism for enabling hand tremor compensation including compensation for a rotation about the optical axis of a lens frame, or lock-on control can be proposed.

Figure 22:
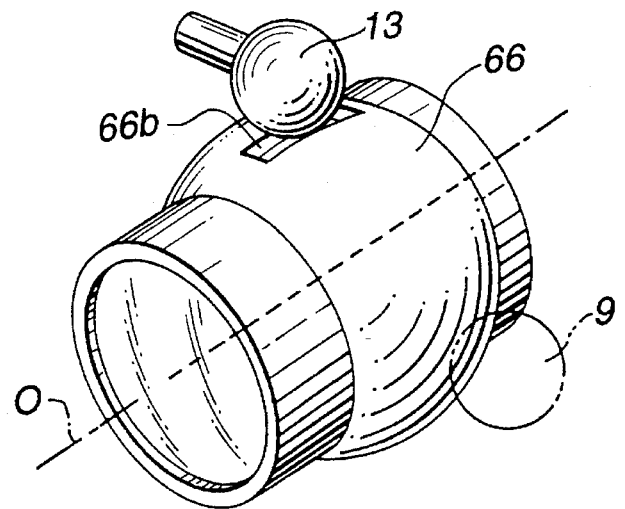
FIG. 22 is an oblique view showing yet another variant of the movement restrainer for the lens frame supporting mechanism of the first embodiment shown in FIG. 1.
Figure 23:
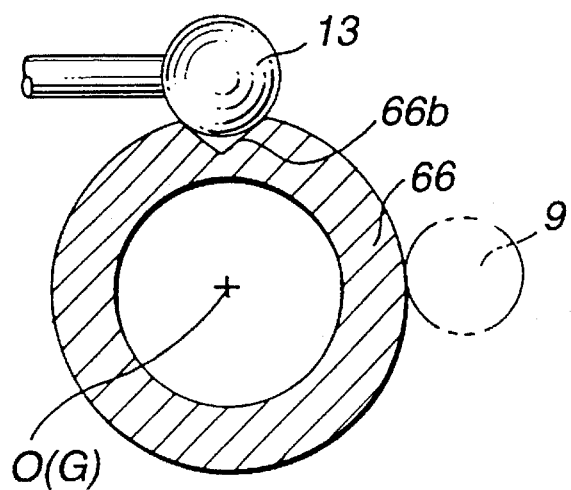
FIG. 23 is a longitudinal sectional view of the movement restrainer of FIG. 22.

FIG. 22 is an oblique view showing yet another variant of the movement restrainer for the lens frame in the lens frame supporting mechanism of the first embodiment. In this variant, a supporting driving member has a capability of the movement restrainer. FIG. 23 is a longitudinal sectional view of a spherical surface of a lens frame in this variant. In this variant, a V-shaped ditch 66b is formed in the part of a spherical surface 66 of a lens frame lying in contact with the spherical rotator 13 that serves as the supporting driving member for vertical rotation. The V-shaped ditch 66b extends in parallel with the optical O. The spherical rotator 9 serving as the supporting driving member for horizontal rotation may have the same structure as that shown in the first embodiment.

The V-shaped ditch 66b works as a movement restrainer for restraining the lens frame from rotating about the optical axis. although a dedicated movement restrainer is not provided, this variant exerts the same effect as the variant shown in FIG. 21. Furthermore, a compact lens barrel can be realized.

Figure 24:
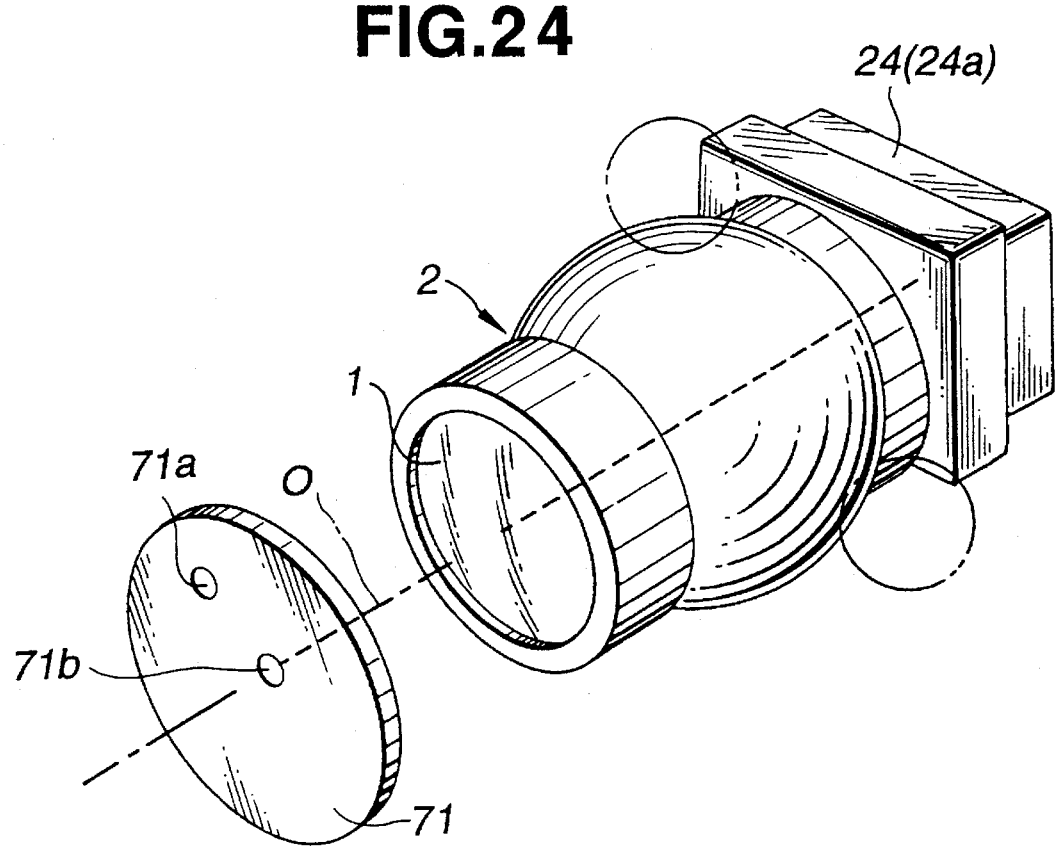
FIG. 24 is an oblique view showing a variant of an after-rotation position detector for the lens frame supporting mechanism of the first embodiment shown in FIG. 1.

FIG. 24 is an oblique view showing a lens frame in which a variant of the after-rotation position detector for the lens frame in the lens frame supporting mechanism of the first embodiment is implemented. When the lens frame is driven to rotate for hand tremor compensation, the position detector detects an after-rotation position of the lens frame. When hand tremor compensation is invalidated, the position detector detects a reference position of the lens frame. In this variant, an indicator 71a or 71b is formed at a specified position on a protective glass 71 located in front of the lens array 1. The protective glass 71 is supposed to be fixed to a lens barrel or a camera body. The indicator 71a is located at a position on the protective glass 71 corresponding to the margin of an image frame or the outside of an imaging zone. The indicator 71b is drawn in black and located in the center of the protective glass. Either of the indicators is needed as a position detector.

When the indicator 71a is used to detect an after-rotation position, an image formation signal, which is produced by the CCD 24a and emitted from a region of the CCD 24a corresponding to the indicator 71a, is fetched. The position at which the signal is detected is computed to find the current after-rotation position of the lens frame.

When the indicator 71b is used to detect an after rotation position, an image formation signal, which is produced by the CCD 24a and represents a black level corresponding to that of the indictor 71b located in the center, is fetched. The position at which the signal scans is computed to detect the current after-rotation position of the lens frame. The imaging information for the indicator 71b is computed by interpolating image formation signals representing areas surrounding the indicator 71b. Only when an after-rotation position is to be detected, the lens array may be focused on the protective glass 71 which is normally unused, and then the position information of the indicator 71b may be acquired.

Figure 25:
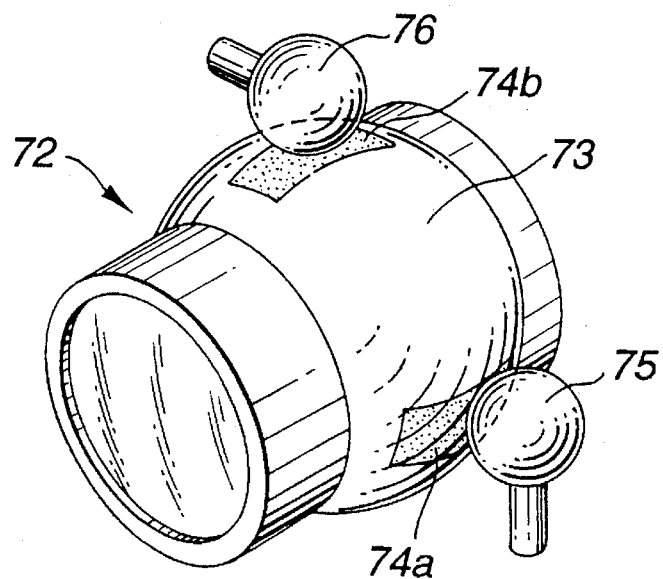
FIG. 25 is an oblique view showing another variant of the after-rotation detector for the lens frame supporting mechanism of the first embodiment shown in FIG. 1.

FIG. 25 is an oblique view showing a lens frame in which another variant of the after-rotation position detector for the lens frame in the lens frame supporting mechanism of the first embodiment is implemented. In the after-rotation position detector of this variant, spherical rotators 75 and 76 serving as supporting driving members are formed with conducting members. Slide resistors 74a and 74b extending along the optical O are placed on the areas of a spherical surface 73 of a lens frame 72 in contact with the spherical rotators 75 and 76. When the lens frame 72 rotates, the spherical rotator 75 or 76 rotates. When the spherical surface 73 rotates, the contact points of the spherical surface 73 relative to the slide resistors 74a and 74b change to vary the resistances. The resistances are analyzed to detect the after-rotation position of the lens frame 72.

According to the foregoing variant, since the contact areas between the supporting driving members and the spherical surface provide the capability of the after-rotation position detector, this structure helps materialize a compact lens frame, and enables precise position detection.

Figure 26:
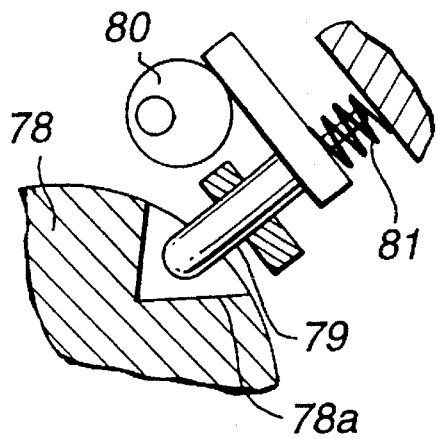
FIG. 26A is a sectional view showing a variant of the locking mechanism for the lens frame in the lens frame supporting mechanism of the first embodiment shown in FIG. 1, wherein the lens frame is unlocked.
FIG. 26B is a sectional view showing a variant of the locking mechanism for the lens barrel in the lens frame supporting mechanism of the first embodiment shown in FIG. 1, wherein the lens frame is locked.
Figure 26:
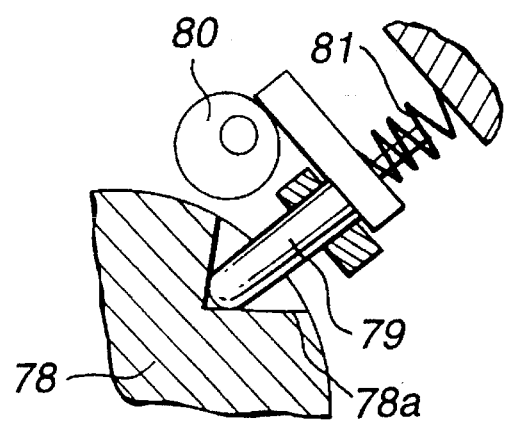

FIGS. 26A and 26B are sectional views showing a variant of the locking mechanism, which, when hand tremor compensation is invalidated, locks a lens frame, in the lens frame supporting mechanism of the first embodiment. FIG. 26A is a sectional view of a locking mechanism, wherein the lens frame is unlocked. FIG. 27B is a sectional view of the locking mechanism, wherein the lens frame is locked. In the locking mechanism of this variant, a conical recess 78a is formed in a spherical surface 78. A lock pin 79 capable of being fitted into the recess 78a is constrained to come out of the recess by means of a spring 81. The lock pin 79 is sunk against the spring 81 with the rotation of a lock cam 80. For unlocking the lens frame, the lock cam 80 is operated to project the lock pin 79. The tip of the lock pin 79 is then fitted in the recess 78a in the spherical surface. Thus, the lens frame is locked (see FIG. 26B).

FIGS. 27A, 27B, and 27C show an attachment lens for a lens frame designed to bear an attachment lens and use the lens frame supporting mechanism of the first embodiment. FIG. 27A is a front view of a protective glass rim attached to the front of a lens barrel. FIG. 27B is a sectional view of the side surface of the protective glass rim. FIG. 27C is a longitudinal sectional view of the protective glass rim with an attachment lens mounted using a filter mounting screw.

In a lens frame permitting hand tremor compensation, as shown in the longitudinal sectional view of the protective glass rim for a lens frame in FIG. 28, the effective imaging range of a protective glass 84 on a protective glass rim 83 is determined to cover a zone defined by L1 and L2, so that even when the lens frame rotates by a specified angle to change the orientation thereof from the direction of the optical OO to the direction of an optical axis O4 or O5; that is, a direction defined when the lens frame rotates by a maximum angle, the margin of an image frame will not be removed to cause vignetting.

However, when an attachment lens is mounted on the protective glass rim 83 of a lens frame permitting hand tremor compensation, the effective imaging range is narrowed because of the attachment lens. This makes it necessary to restrict a hand tremor compensation range. In a lens frame designed to bear an attachment lens, as shown in FIGS. 27A and 27B, a lens attachment detecting switch 83a is installed on the protective glass rim 83. When a lens rim 86 of an attachment lens is mounted on the protective glass rim 83 as shown in FIG. 27C, the detecting switch 83a is turned on. A permissible angle of rotation defining a hand tremor compensation range is set to a value that does not allow an attachment lens 85 to cause vignetting. Alternatively, when the attachment lens 85 is mounted, hand tremor compensation may be inhibited.

In the lens frame permitting hand tremor compensation, even when an attachment lens is mounted, a problem that part of an image frame is removed to cause vignetting because of the rotation of a lens frame for hand tremor compensation will not occur.

FIG. 29 is an oblique view of the front of a lens frame using the lens frame supporting mechanism of the first embodiment and having a dustproof facility. In the lens frame, a dustproof screen 86, formed of a sheet-type elastic member that is freely stretchable, is attached to the front part of lens barrel 85. In this structure, even when the lens frame is rotated for hand tremor compensation, the dustproof screen 86 prevents dust from entering the lens frame or camera.

Figure 30:
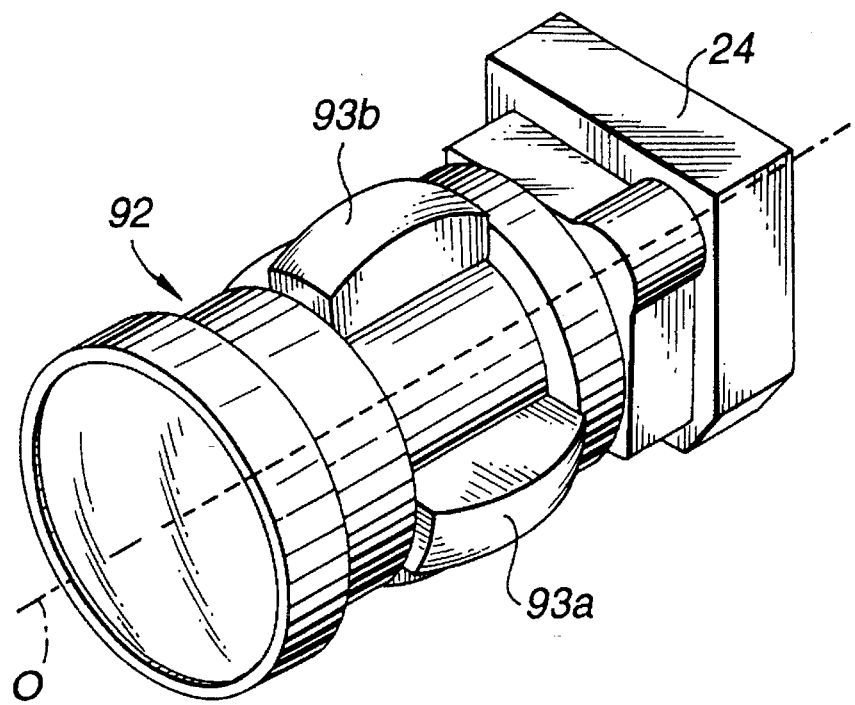
FIG. 30 is an oblique view of the lens frame in which a lens frame supporting mechanism representing a second embodiment of the present invention is implemented.
Figure 31A:
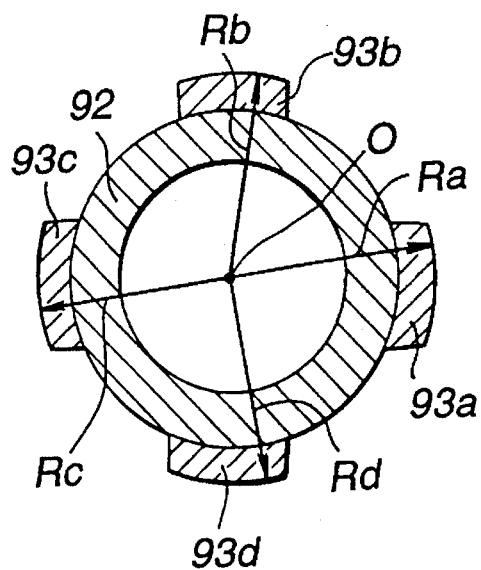
FIG. 31A shows a longitudinal section, which is perpendicular to the optical axis, of a spherical surface of the lens frame of FIG. 30.
Figure 31B:
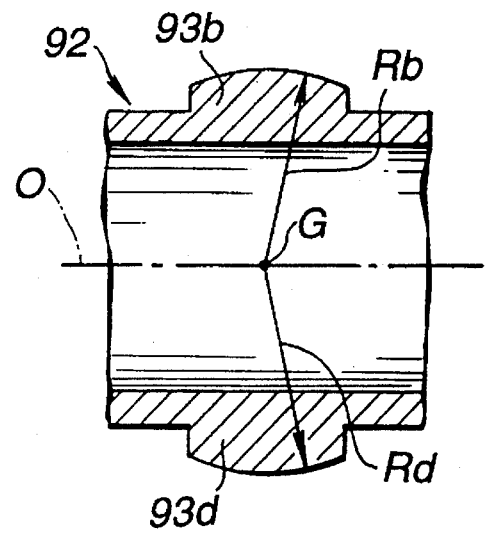
FIGS. 31B shows a longitudinal section, which is parallel to the optical axis, of the spherical surface of the lens frame of FIG. 30.

FIG. 30 is an oblique view showing a lens frame in which a lens frame supporting mechanism of the second embodiment of the present invention is implemented. A lens frame 92 is characterized by the outline of a spherical surface 93 that is a driven and supported member. FIG. 31A shows a longitudinal section of the spherical surface 93 that is perpendicular to the optical axis. FIG. 31B shows a cross section of the spherical surface 93 that is in parallel with the optical axis. The other components and operations are identical to those of the first embodiment.

In the lens frame supporting mechanism of this embodiment, as shown in FIGS. 30, 31A, and 31B, the spherical surface 93 has bumps 93a, 93b, 93c, and 93d in areas with which supporting driving members or spherical rotators may come into contact. The curvatures of the bumps are centered on a rotation center G through which the optical axis of a lens frame 92 passes. Assuming that the radii from the center G to the surfaces of the bumps are Ra, Rb, Rc, and Rd, the values Ra, Rb, Rc, and Rd need not be the same but may vary if necessary.

In the lens frame supporting mechanism of this embodiment having the aforesaid structure, a minimum area of the lens frame 92 is specified as the spherical surface 93. The moment of inertia arising during the rotation of the lens frame is therefore limited, which results in the small driving load and the short response time. The space occupied by the lens frame is therefore limited to realize a more compact lens frame.

Figure 32:
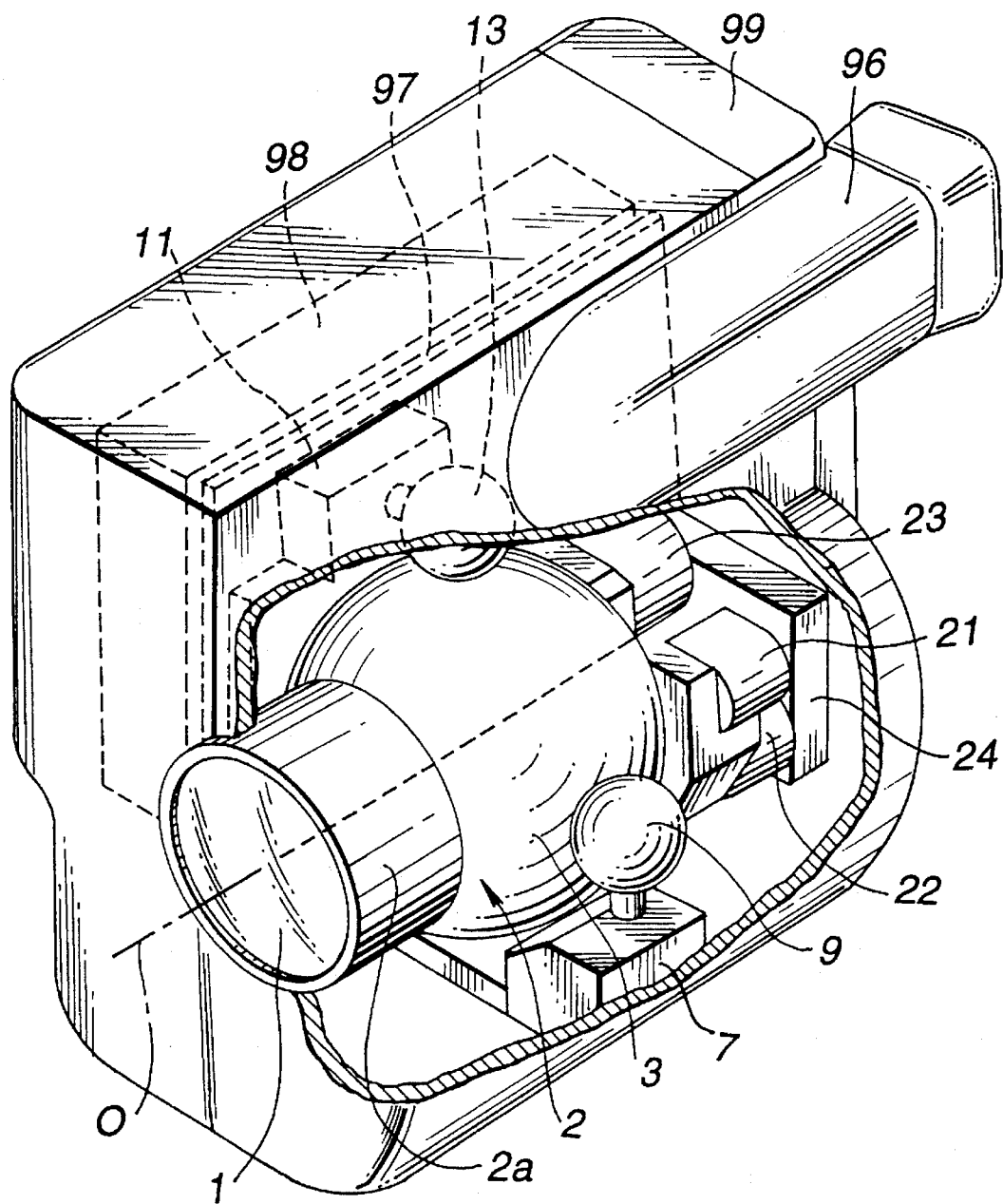
FIGS. 32 is an oblique view showing the lens frame supporting mechanism of the first or second embodiment that is incorporated in a camera-inclusive VTR with a hand tremor compensation facility.

FIG. 32 is an oblique view showing the lens frame supporting mechanism of the first or second embodiment which is incorporated in a camera-inclusive VTR with a hand tremor compensation facility. As shown in FIG. 32, the lens frame 2 (see FIG. 1) of lens frame 92 (see FIG. 30) supported by the lens frame supporting mechanism is located in the right-hand area in a camera body viewed from the front side of the camera. A printed wiring board 97 in charge of control is arranged to the left of the lens frame. A cassette tape case 98 can be loaded to the left of the printed wiring board 97. A viewfinder 96 and a detachable battery 99 are mounted on the back of the camera.

As mentioned above, in the lens frame supporting mechanism of the first or second embodiment, a lens frame has a spherical surface, which works as a driven and supported member, as a specific region of an outer surface thereof. Rotators serving as supporting driving members are used to support the spherical surface. When the supporting driving members rotate in contact with the spherical surface, the spherical surface is driven to rotate. This structure results in the simple supporting mechanism, the compact lens frame, and the reduced load to a rotation actuator.

Figure 37:
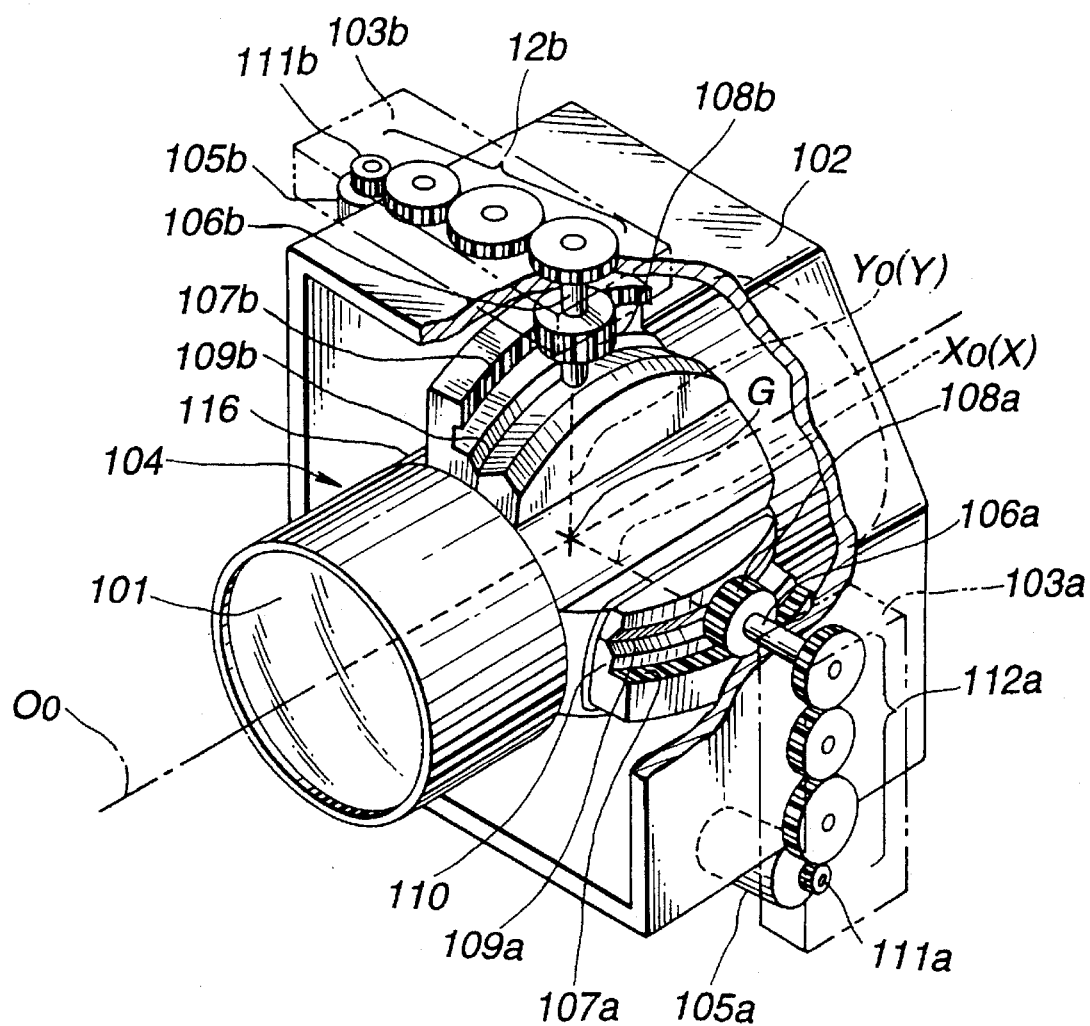
FIG. 37 is an oblique view showing a major portion of a lens frame supporting mechanism representing a third embodiment of the present invention.

FIG. 37 is an oblique view showing how a major portion of a lens barrel unit 104 in a lens frame supporting mechanism of the third embodiment of the present invention is implemented. Unlike the conventional lens frame supporting mechanism having the gimbal structure described in conjunction with FIG. 105, the lens frame supporting mechanism for the lens barrel unit 104 has a lens frame 116 that is supported so as to rotate with respect to a rotation center G on an optical OO. The lens frame 116 is driven to rotate about an X or Y axis, which passes through the center G, using two actuators.

In the lens frame supporting mechanism of the first embodiment shown in FIG. 1, which has been proposed as a solution of the drawbacks lying in the conventional lens frame supporting mechanism having the gimbal structure shown in FIG. 105, the whole of the outer circumference of a lens frame is specified as a driven spherical surface. Friction gearing is adopted as a driving method. A structure based on the friction gearing method may exert frictional slide resistance though slightly on a surface to be driven with frictional force in a direction opposite to the driving direction.

Figure 33A:
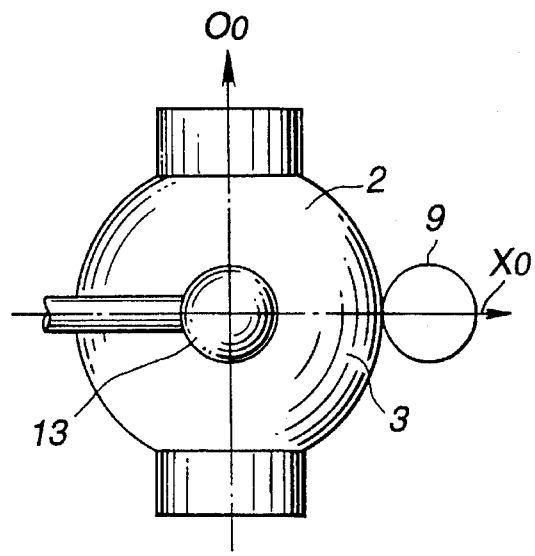
FIG. 33A is a plan view showing a major portion of the lens frame supporting mechanism of the first embodiment shown in FIG. 1 in a state of operation in which the lens frame stays in a neutral state.
Figure 33B:
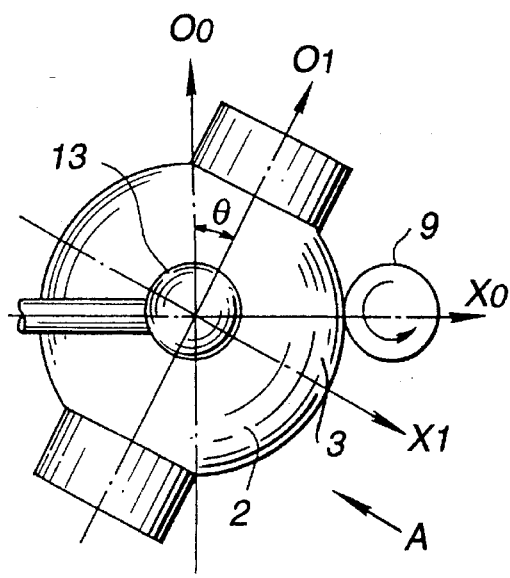
FIG. 33B is a plan view showing the major portion of the lens frame supporting mechanism of the first embodiment shown in FIG. 1 in a state of operation in which the lens frame is driven by the second supporting driving member.
Figure 34A:
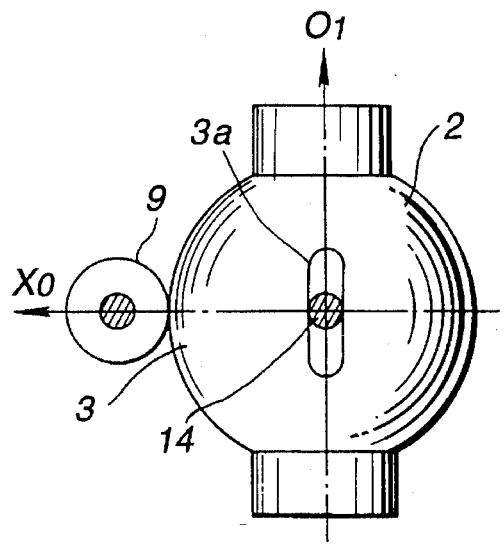
FIG. 34A is a bottom view showing the major portion of the lens frame supporting mechanism of the first embodiment shown in FIG. 1 in the same state of operation as the one in FIG. 33A.
Figure 34B:
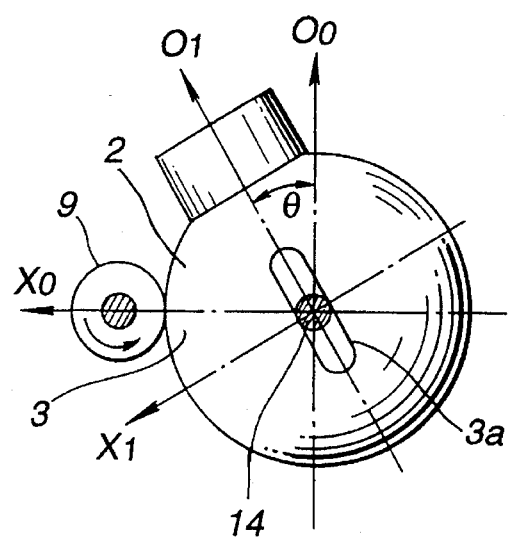
FIG. 34B is a bottom view showing the major portion of the lens frame supporting mechanism of the first embodiment shown in FIG. 1 in the same state of operation as the one in FIG. 33B.
Figure 35A:
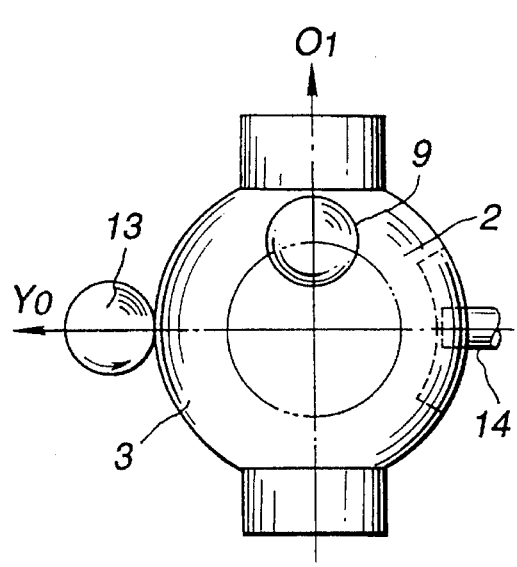
FIG. 35A is a view showing a state of operation of the lens frame supporting mechanism of the first embodiment in FIG. 1 looking in the direction of arrow 35 in FIG. 33B.
Figure 35B:
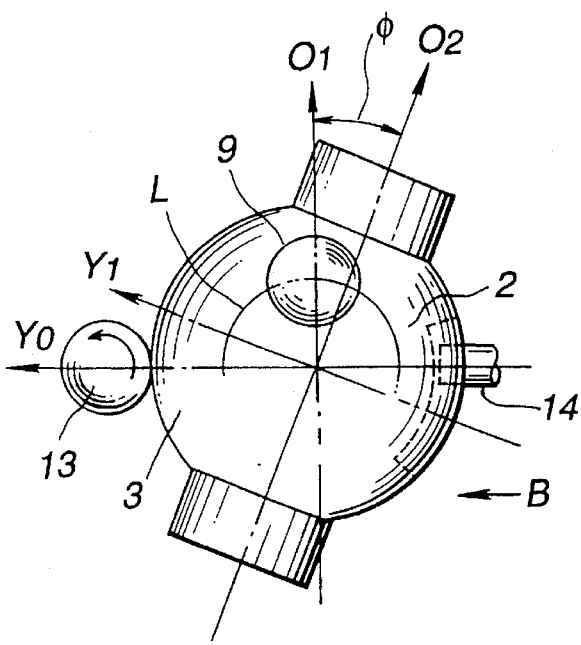
FIG. 35B shows a state of operation of the lens frame supporting mechanism of the first embodiment in FIG. 1; that is, a state in which the lens frame has been driven by the first supporting driving member and changed from the state shown in FIG. 35A.
Figure 36:
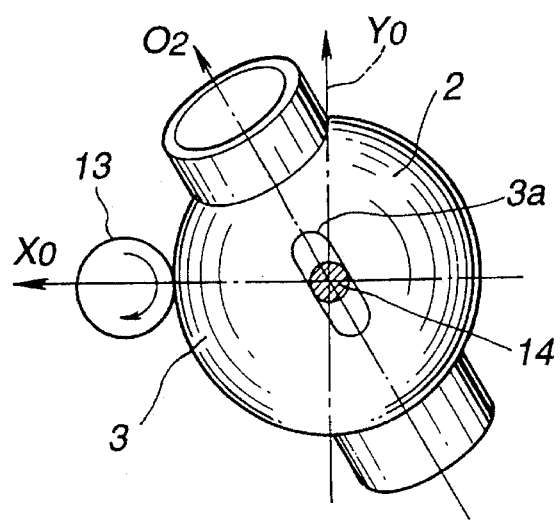
FIG. 36 is a view of FIG. 35B looking in the direction of arrow 36 in FIG. 35B.

The frictional slide resistance will be discussed below. FIGS. 33A and 33B show the states of operation of the lens frame supporting mechanism of the first embodiment shown in FIG. 1. FIG. 33A is a plan view showing a major portion of the mechanism, wherein the lens frame 2 is oriented so that the reference optical OO will intersect the axes XO and YO perpendicularly; that is, the lens frame 2 is placed in the neutral state. FIG. 33B is a plan view, wherein the second supporting driving member 9 alone is driven to rotate the lens frame 2 by an angle 8. In this state, the optical axis of the lens frame is oriented in the direction of the optical O1. An axis X1 intersects the optical O1 perpendicularly. FIGS. 34A and 34B are back views of FIGS. 33A and 33B, viewing the lens frame supporting mechanism from the side of the movement restraining pin 14. FIG. 35A is a view of FIG. 33B looking in the direction of arrow 35. FIG. 36 is a view of FIG. 35B looking in the direction of arrow 36.

When the foregoing lens frame supporting mechanism is driven to change from the state in FIG. 33A to that shown in FIG. 33B, the second supporting driving member 9 does not slip relative to the spherical surface 3. There is no problem concerning drive.

However, when the first supporting driving member 13 is actuated in the state shown in FIG. 33B or FIG. 35A, the first supporting driving member 13 is actuated to rotate the lens frame 2 by an angle φ about the axis X1 in FIG. 33B. The optical axis O of the lens frame then shifts from the axis O1 to O2 as shown in FIG. 35B. Due to the rotation about the axis X1, the second supporting driving member 9 slips along an arc L in the contact area thereof 10 relative to the spherical surface 3. This means that when the first supporting driving member 13 is actuated, the slip may induce frictional slide resistance.

To overcome the foregoing drawback, the lens frame supporting mechanism shown in FIG. 37 is proposed as the third embodiment of the present invention.

The lens frame supporting mechanism of the third embodiment will now be described in detail. The lens frame supporting mechanism of this embodiment drives horizontally and vertically, as shown in the perspective oblique view of FIG. 37, a lens frame 116 of a lens barrel unit 104 being encased in a support frame 102. The lens barrel unit 104 comprises the lens frame 116 for holding either a lens array 101 or an optical system, an independent rotary member 110 that is supported by the lens barrel unit 104 so as to rotate freely, and two actuators; that is, X- and Y-axis actuators for rotating the lens barrel unit 104 relative to axes XO and YO that are mutually perpendicular.

Figure 38:
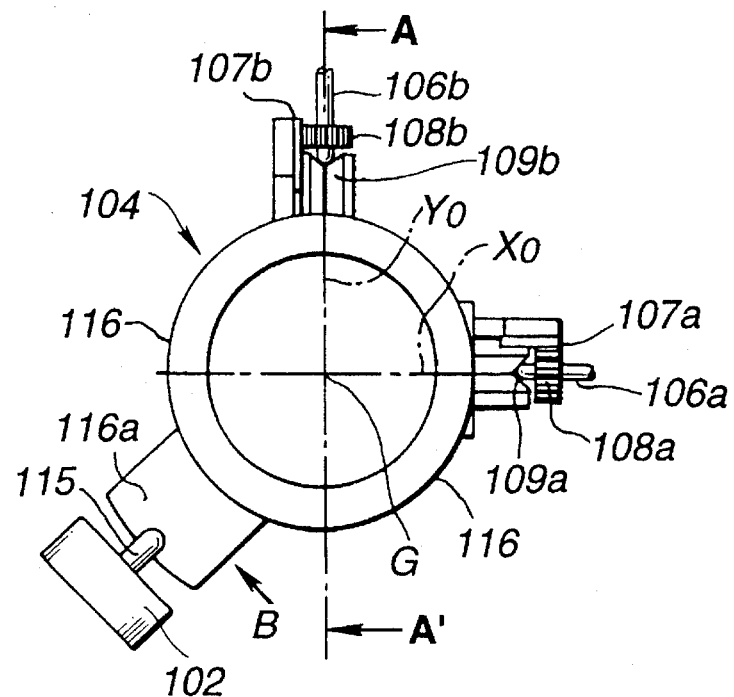
FIG. 38 is a front view showing a major portion of the lens frame supporting mechanism in FIG. 37.
Figure 39:
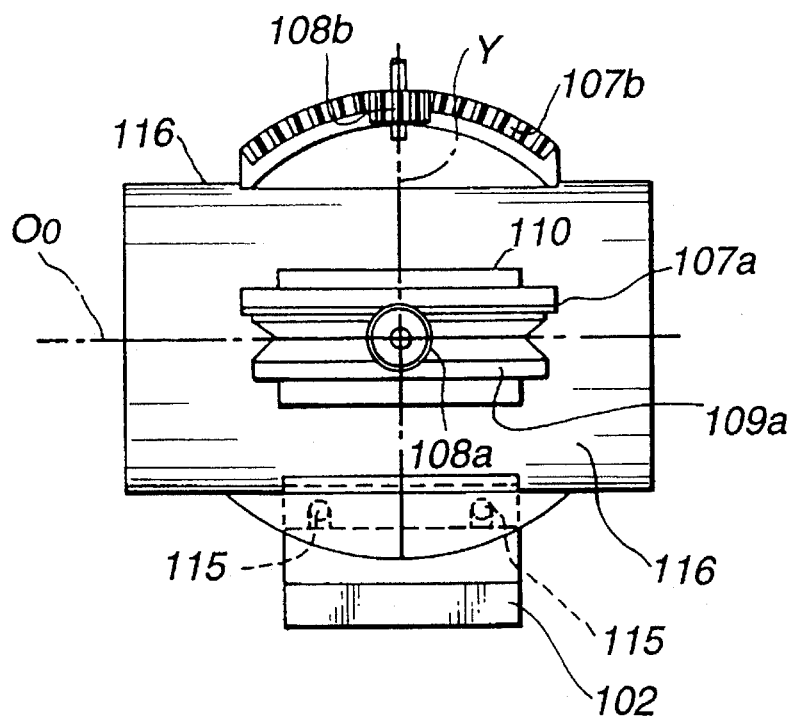
FIG. 39 is a side view showing the major portion of the lens frame supporting mechanism in FIG. 37.
Figure 40:
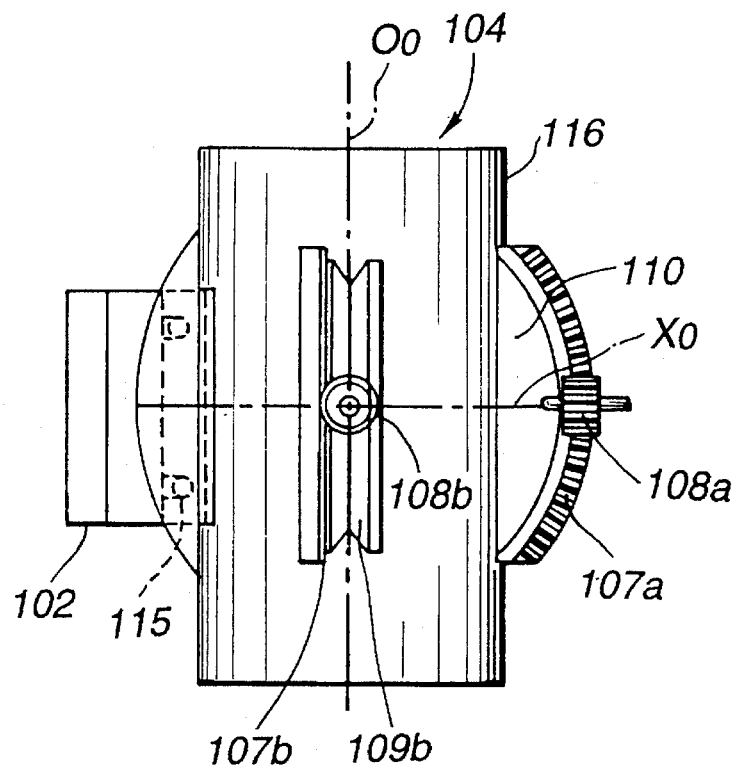
FIG. 40 is a plan view showing the lens frame supporting mechanism in FIG. 37.
Figure 41:
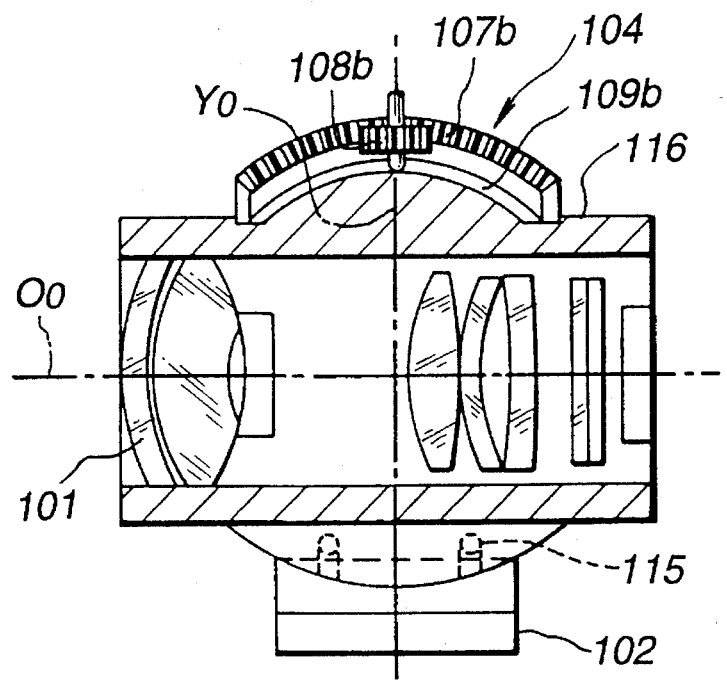
FIG. 41 shows a section of FIG. 38 looking in the direction of arrows 41—41'.

FIG. 38 is a front view of the lens barrel unit 104. FIG. 39 is a side view. FIG. 40 is a plan view. FIG. 41 is a sectional view of FIG. 38 looking in the direction of arrows 41—41'. XO and YO respectively denote horizontal and vertical axes, which are reference axes for the support frame 102. OO denotes a reference optical axis that, when the lens frame stays in the neutral state, acts as a reference. X, Y, and 0 respectively denote the horizontal, vertical and optical axes of the lens frame 116 driven to rotate. The axes XO and YO, or X and Y are mutually perpendicular. When the lens frame 116 is located at the neutral position, the 10 axes XO, YO, and OO are consistent with the axes X, Y, and 0. The intersection among the axes XO, YO, and OO or the axes X, Y, and 0 is consistent with a rotation center G. The center G is located in the vicinity of a center of gravity of the lens frame.

The X-axis actuator is composed of a drive motor 105a fixed to the support frame 102, a gear array 112a that is encased in a gear box 103a and driven by an output pinion 111a of the drive motor 105a, a drive shaft 106a that is driven by the gear array 112a and is freely rotatable about the axis XO, and a driving gear 108a fixed to the drive shaft 106a. The driving gear 108a is a spur gear.

The Y-axis actuator is composed of a drive motor 105b fixed to the support frame 102, a gear array 112b that is encased in a gear box 103b and driven by an output pinion 111b of the drive motor 105b, a drive shaft 106b that is driven by the gear array 112b and freely rotatable about the axis YO, and a driving gear 108b fixed to the drive shaft 106b. The driving gear 108b is a spur gear.

On the top of the lens frame 116, a V-shaped ditch 109b is formed to draw a circular arc which passes through the axes Y and O and whose center coincides with the rotation center G. The V-shaped ditch 109b is provided as a movement restrainer for restraining the lens frame 115 from rotating about the optical axis. As shown in the oblique view of FIG. 42 and the sectional view of FIG. 43, the V-shaped ditch 109b is supported by the drive shaft 106b whose spherical tip 106bO is in contact with the V-shaped ditch 109b, thus restraining the rolling or rotation of the lens frame 116 about the optical axis. The V-shaped ditch 109b works as a supported member and in turn supports the lens frame 116 so that the lens frame 116 can rotate freely. The ditch may alternatively be shaped like a letter U or a rectangle.

Figure 42:
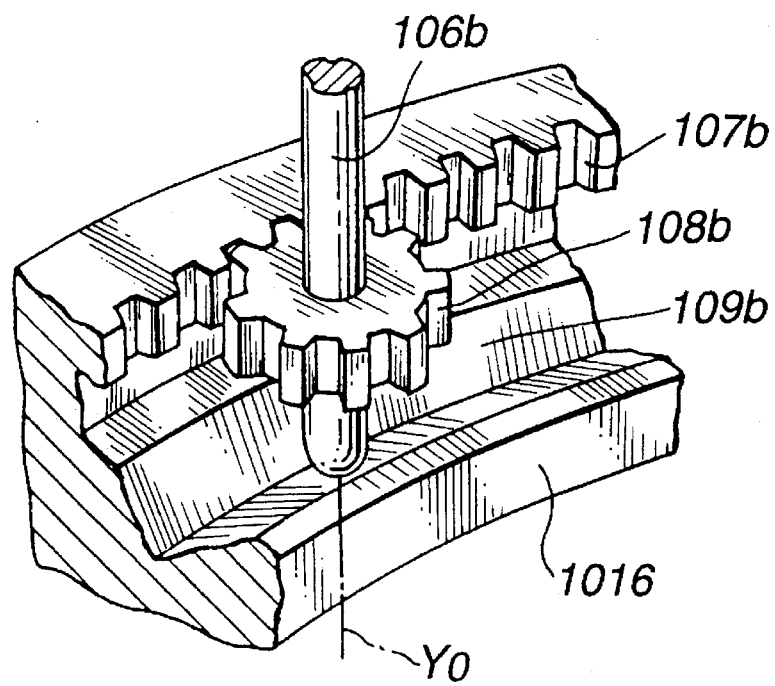
FIG. 42 is an oblique view showing a gear and a V-shaped ditch in the lens frame supporting mechanism of FIG. 37.
Figure 43:
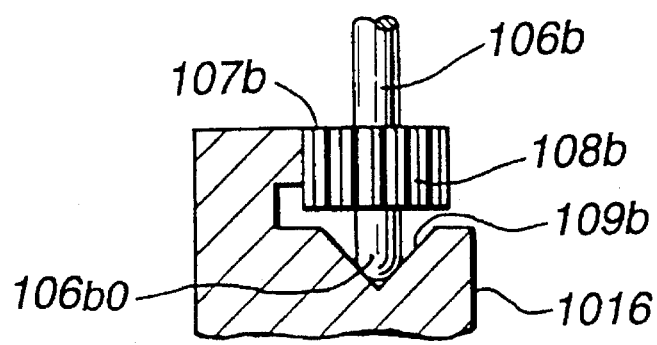
FIG. 43 is a sectional view showing a gear and a V-shaped ditch in the lens frame supporting mechanism of FIG. 37.

The lens frame 116 has, as shown in FIGS. 42 and 43, a face gear 107b serving as a driven gear. The face gear 107b is formed along the V-shaped ditch 109b with the X axis as a rotation center. The face gear 107b engages the driving gear 108b. When the driving gear 108b rotates, the lens frame 116 therefore rotates about the XO axis perpendicular to the YO axis.

The independent rotary member 110 is supported by a support pin 110a so as to freely rotate along the X axis on the lens frame 116. The independent rotary member 110 has a V-shaped ditch 109a formed to define an arc crossing the X axis. As shown in the oblique view of FIG. 44 and the sectional view of FIG. 45, the V-shaped ditch 109a is supported by the driving axis of shaft 106b whose spherical tip 106aO is in contact with the V-shaped ditch 109a.

Figure 44:
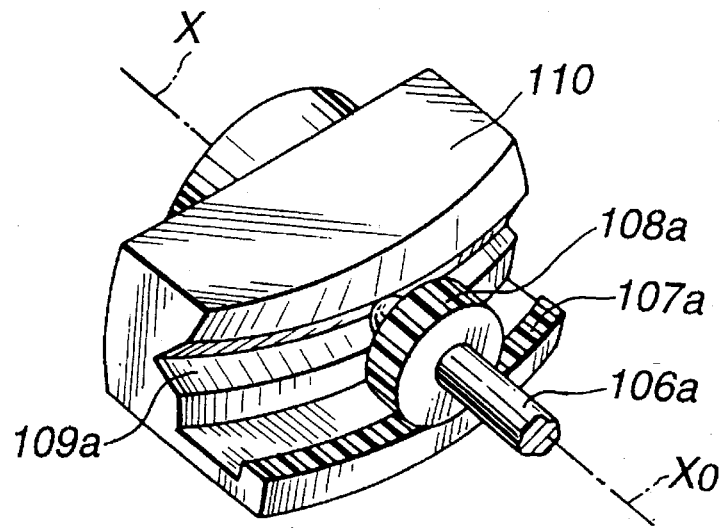
FIG. 44 is an oblique view showing an independent rotary member in the lens frame supporting mechanism of FIG. 37.
Figure 45:
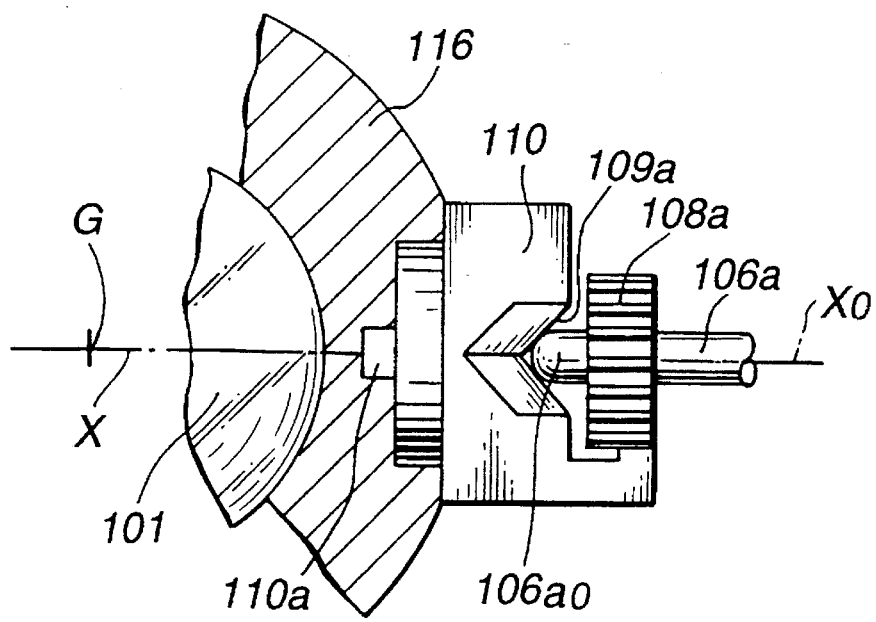
FIG. 45 is a sectional view showing the independent rotary member in the lens frame supporting mechanism of FIG. 37.

The independent rotary member 110 has, as shown in FIGS. 44 and 45, a face gear 107a serving as a driven gear. The face gear 107a is formed along the V-shaped ditch 109a with the rotation center G of the lens frame 116 as a rotation center. The face gear 107a engages the driving gear 108a. When the driving gear 108a rotates, the lens frame 116 rotates about the YO axis perpendicular to the XO axis owing to the independent rotary member 110.

Figure 46:
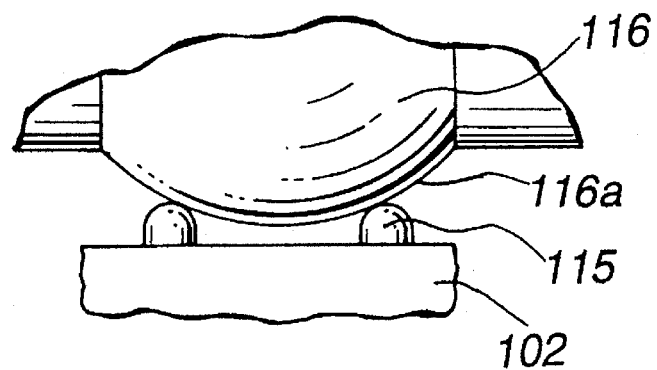
FIG. 46 is a view of FIG. 38 showing a supporting structure in the lens frame supporting mechanism of FIG. 37 looking in the direction of arrow 46.

FIG. 46 is a view of FIG. 38 looking in the direction of arrow 46, showing a supporting structure of the lens frame 116. As illustrated, a spherical surface 116a is formed on the lens frame 116 and opposed to the areas of the lens frame 116 10 in contact with the drive shafts 106a and 106b. The spherical surface 116a is substantially in point contact with spherical or semi-spherical supporting members 115 fixed to the support frame 102 so that the spherical surface 116a can slide freely. The spherical surface 116a is thus supported by the supporting members 115. The supporting members may be located in a recess (not shown) provided in the spherical surface 116a.

The states of operation of the lens frame supporting mechanism of this embodiment having the aforesaid structure will now be described in conjunction with FIGS. 47 to 52.

Figure 47:
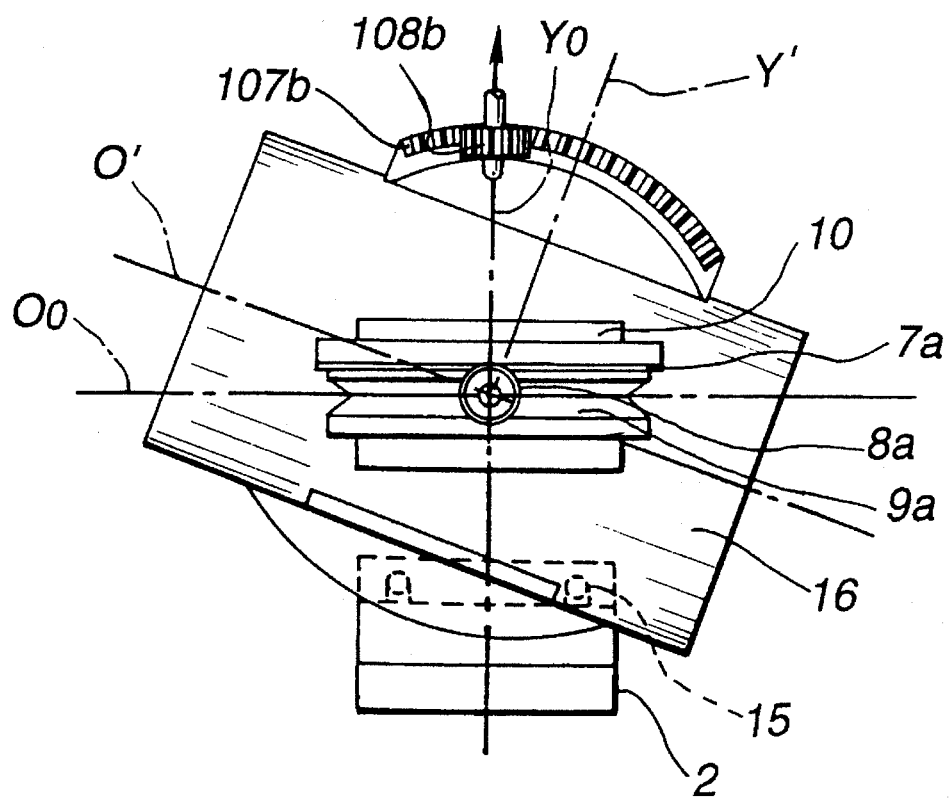
FIG. 47 is a side view of the lens frame supporting mechanism shown in FIG. 37, wherein the lens frame has been rotated about the X axis and changed from the neutral state.
Figure 48:
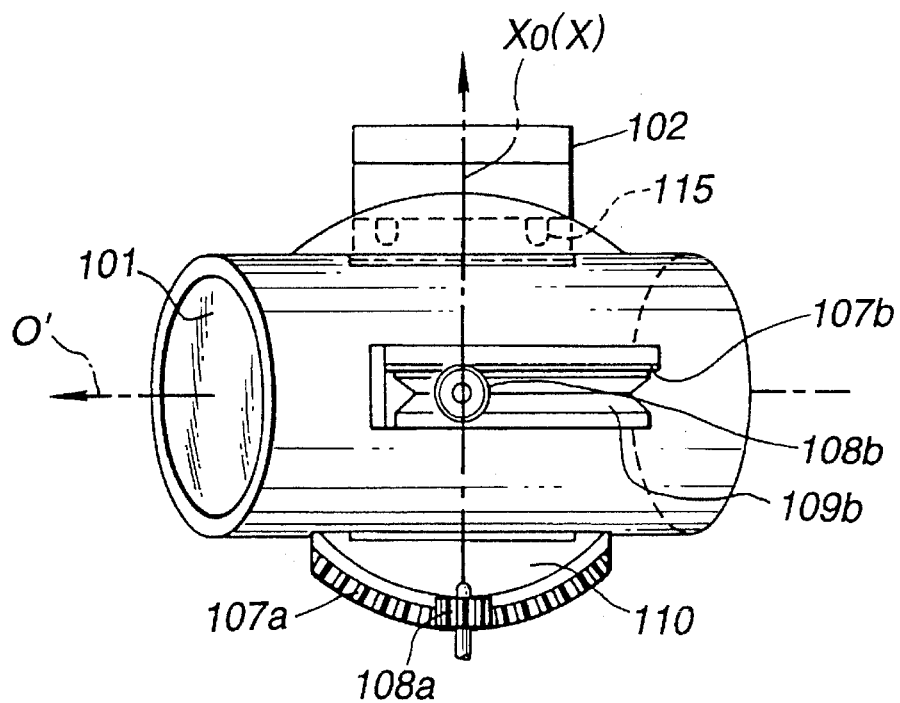
FIG. 48 is a plan view of the lens frame supporting mechanism shown in FIG. 37 in the state of rotation shown in FIG. 47.

FIG. 47 is a side view showing the lens frame 116 that has been changed from the neutral state shown in the side view of FIG. 39, wherein the driving gear 108b is actuated by the Y-axis actuator so that the Y axis of the lens frame 116 will be oriented in the Y' direction and the optical axis thereof will be oriented in the O' direction. In this state, even when the lens frame 116 is rotated, the independent rotary member 110 is held intact as shown in FIG. 47. FIG. 48 is a plan view showing the lens frame 116 in the state shown in FIG. 47.

Figure 49:
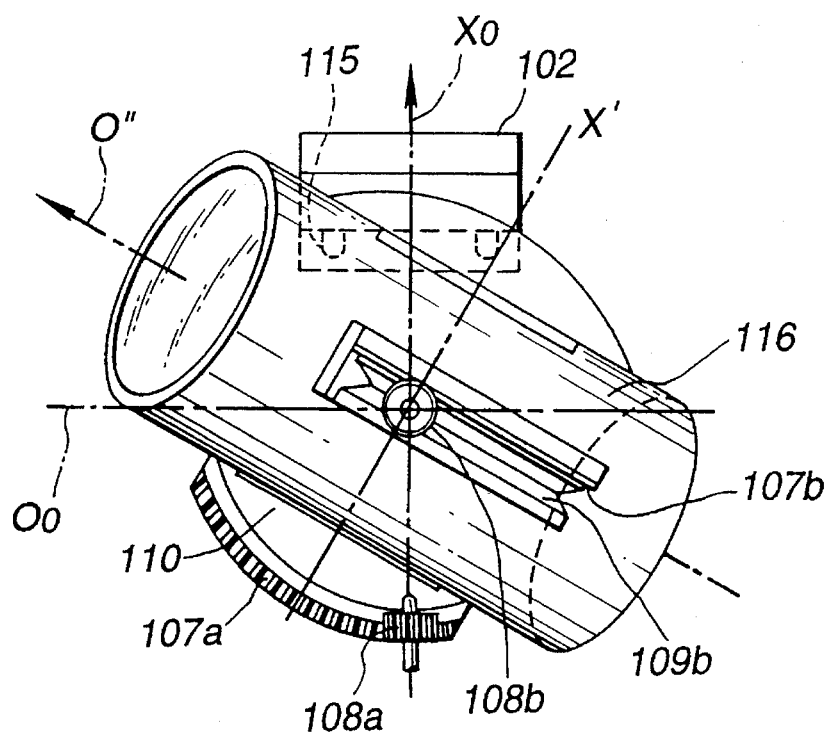
FIG. 49 is a plan view of the lens frame supporting mechanism shown in FIG. 37, wherein the lens frame has been rotated about the Y axis and changed from the state of rotation shown in FIG. 47 or 48.
Figure 50:
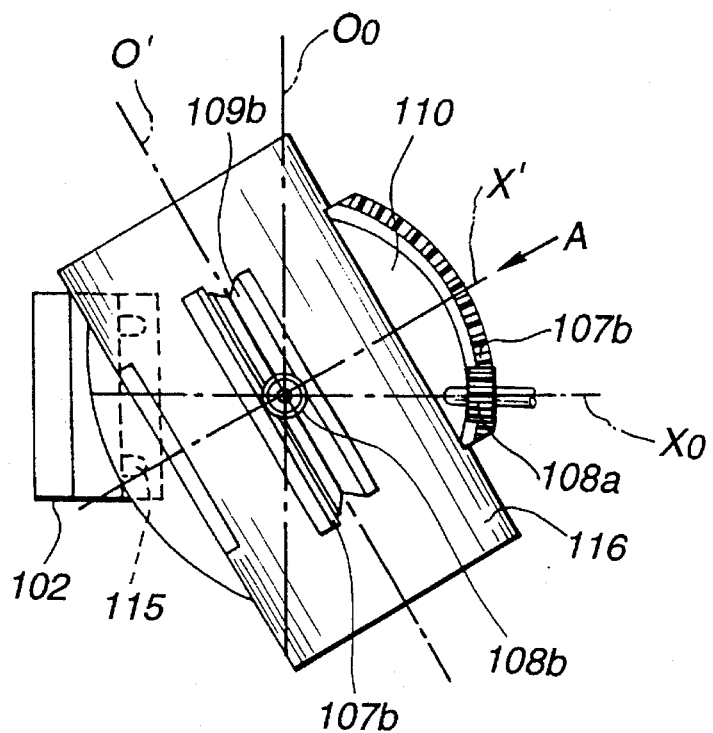
FIG. 50 is a plan view of the lens frame supporting mechanism shown in FIG. 37, wherein the lens frame has been rotated about the y axis and changed from the neutral state.
Figure 51:
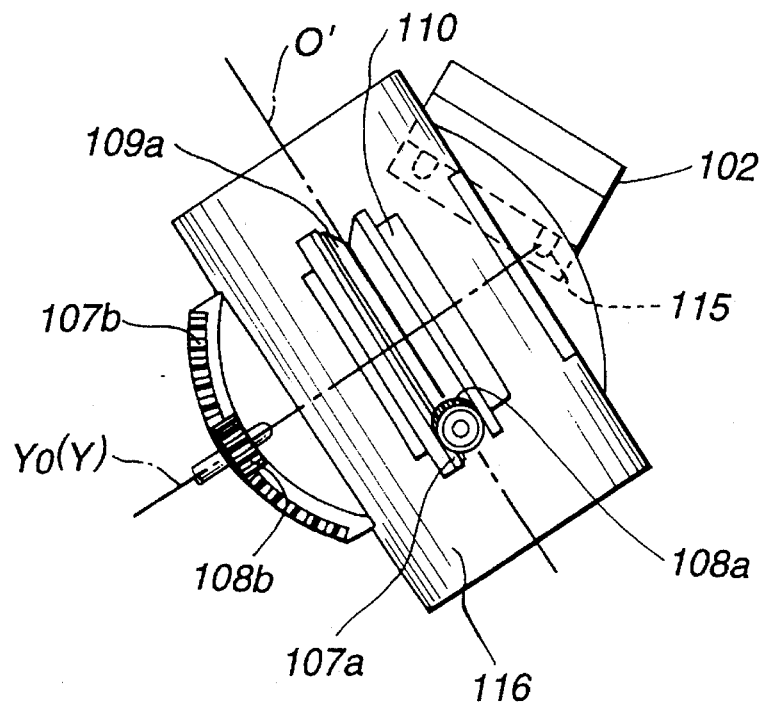
FIG. 51 is a view of the lens frame supporting mechanism of FIG. 50 looking in the direction of arrow 51.

FIG. 49 is a plan view showing the lens frame 116 that has been changed from the state of rotation shown in FIGS. 47 and 48, wherein the driving gear 108a is actuated by the X-axis actuator so that the X axis of the lens frame 116 will be oriented in the X' direction and the optical axis thereof will be oriented in the 0' direction. FIG. 51 is a view of FIG. 50 looking in the direction of arrow 51.

Figure 52:
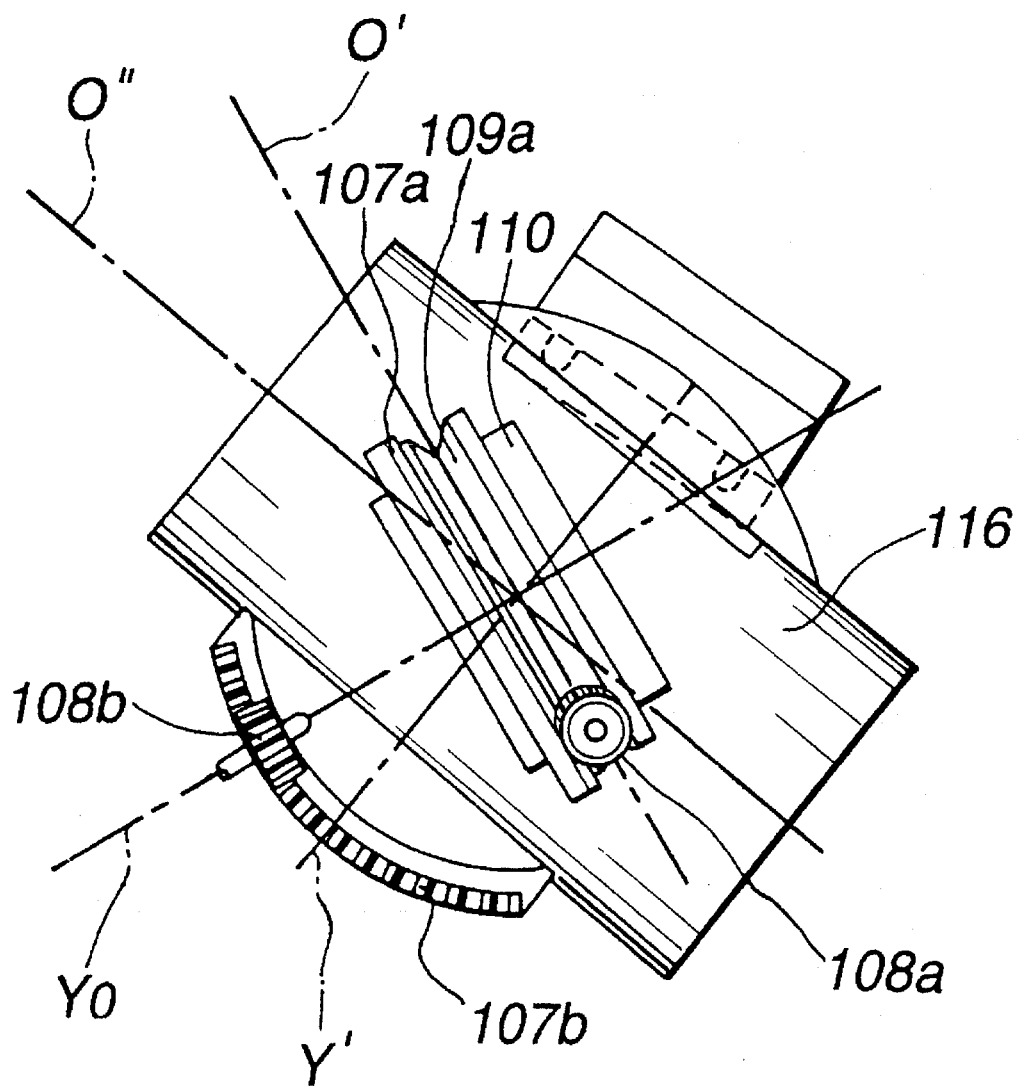
FIG. 52 shows the lens frame supporting mechanism of FIG. 37, wherein the lens frame has been rotated about the X axis and changed from the state of rotation shown in FIG. 50 or 51.

In. FIG. 52, the lens frame 116 has been changed from the neutral state shown in FIG. 51. The driving gear 108b is actuated by the Y-axis actuator so that the Y axis of the lens frame 116 will be oriented in the Y' direction and the optical axis thereof will be oriented in the O" direction. In this state, the surface of the face gear 107a of the independent rotary member 110 is held horizontal.

As mentioned above, in the lens frame supporting mechanism of this embodiment, the two face gears 107a and 107b are employed as driven gears. One of the face gears; that is, the face gear 107a, is included in the independent rotary member 110 that serves as an X-axis driven member and rotates about the X axis. The lens frame 116 therefore smoothly rotates about the X and Y axes. Since no frictional driving member is used, an increase in a driving load caused by frictional resistance is limited to enable rotation drive with a smaller driving torque. The lens barrel unit 104 can thus be designed more compactly.

The locations of the support frame 102, X-axis actuator, and Y-axis actuator relative to the lens frame 116 in the lens frame supporting mechanism of the third embodiment shown in FIG. 37 will now be described.

Figure 53:
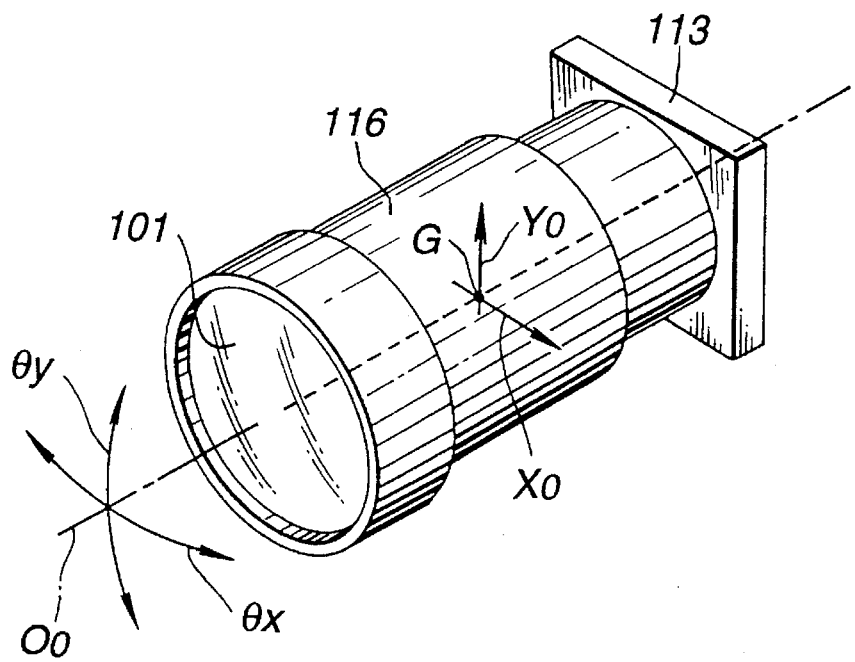
FIG. 53 is a schematic oblique view showing the lens frame in the lens frame supporting mechanism in FIG. 37.
Figure 54:
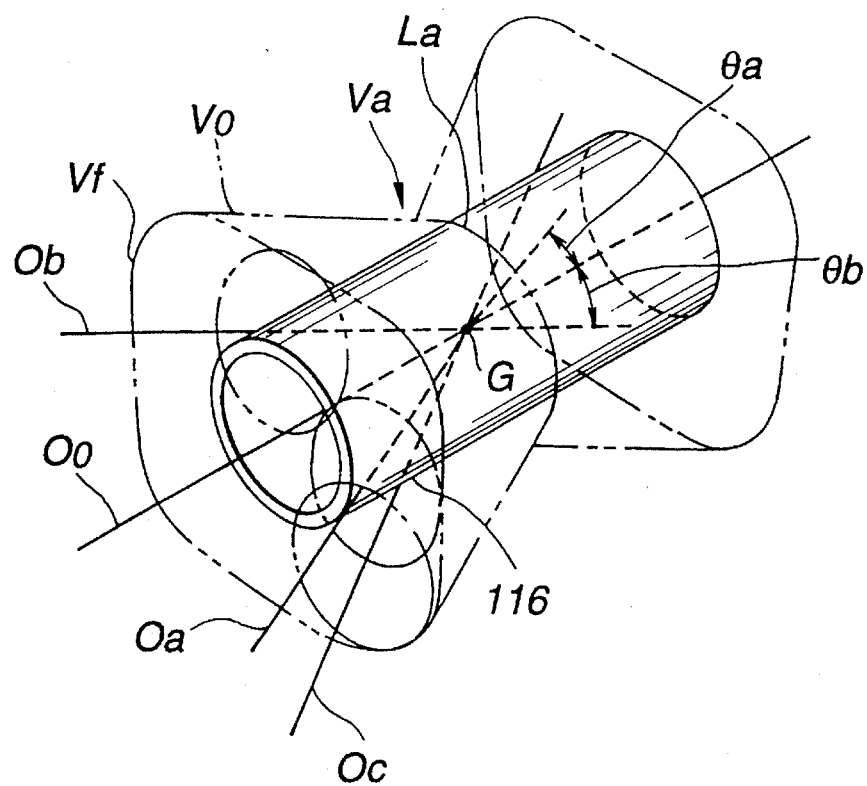
FIG. 54 is an oblique view showing a rotation trajectory of the outline of the lens frame in the lens frame supporting mechanism of FIG. 37.

As described previously, when the driving gear 108b rotates, as shown in the schematic oblique view of FIG. 53, the lens frame 116 rotates in the θy direction or about the XO axis perpendicular to the YO axis. When the driving gear 108a rotates, the lens frame 116 rotates in the θx direction or about the YO axis perpendicular to the XO axis. 10 The lens frame 116 rotates with the point G as a center. As shown in the oblique view of FIG. 54, the outline of the lens frame 116 draws a trajectory VO having a trough Va. The trough Va lies in a plane perpendicular to the reference optical OO so that when the lens frame 116 is in the neutral state, OO is defined as a reference axis. An optical axis Ob in FIG. 54 is defined as an optical axis, when the lens frame has rotated by a maximum angle of rotation θb in the θy direction. An optical axis Oa is defined as an optical axis, when the lens frame has rotated by a maximum angle of rotation θa in the θx direction. An optical axis Oc is defined as an optical axis, when the lens frame has rotated by the angle of rotation θa in the θ direction at the same time. In FIG. 54, as well as FIGS. 55 to 62 which will be described later, La denotes the trough line of the trough Va and Vf denotes a trajectory of the outline of the front part of the lens frame 116.

Figure 55:
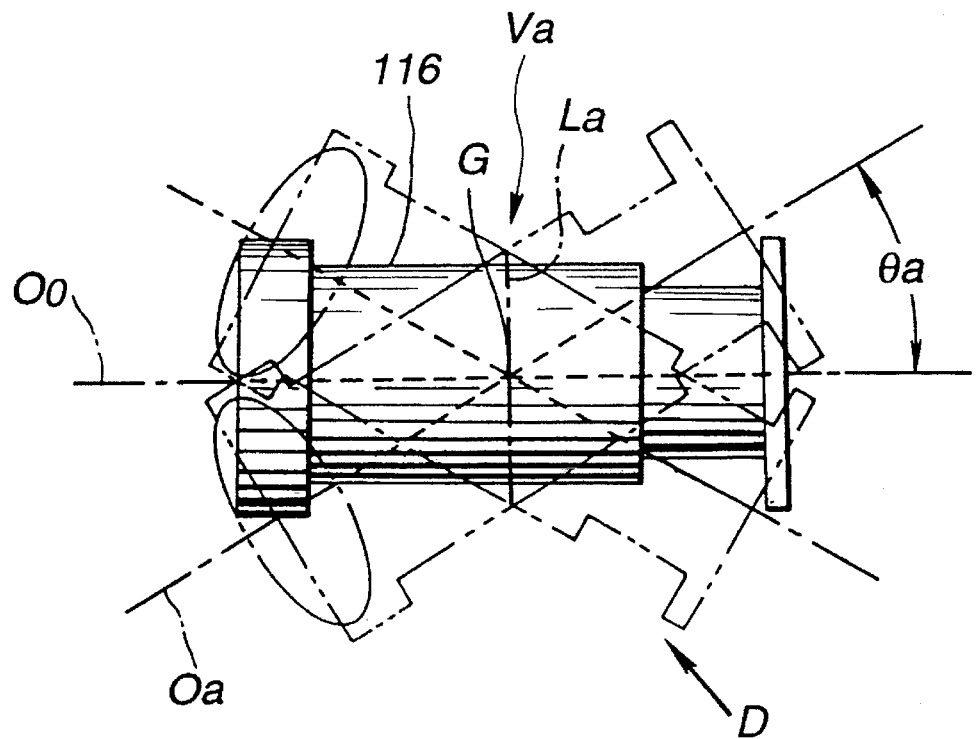
FIG. 55 is a plan view showing the rotation trajectory of the outline of the lens frame in the lens frame supporting mechanism of FIG. 54.
Figure 56:
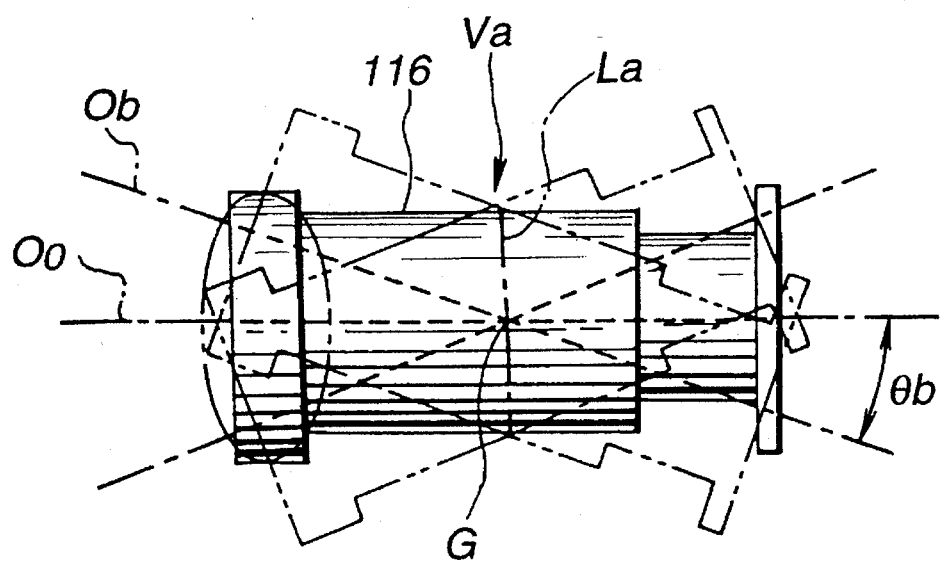
FIG. 56 is a side view showing the rotation trajectory of the outline of the lens frame in the lens frame supporting mechanism of FIG. 54.
Figure 57:
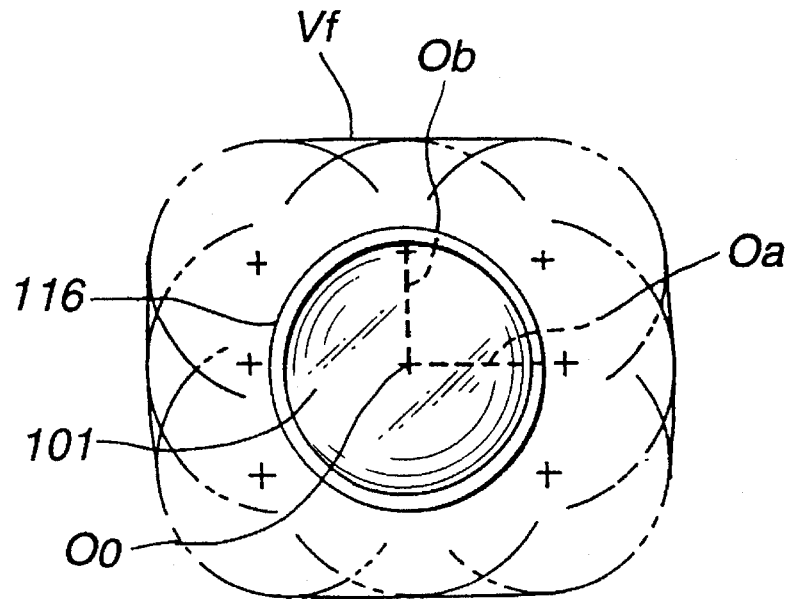
FIG. 57 is a front view showing the rotation trajectory of the outline of the lens frame in the lens frame supporting mechanism of FIG. 54.
Figure 58:
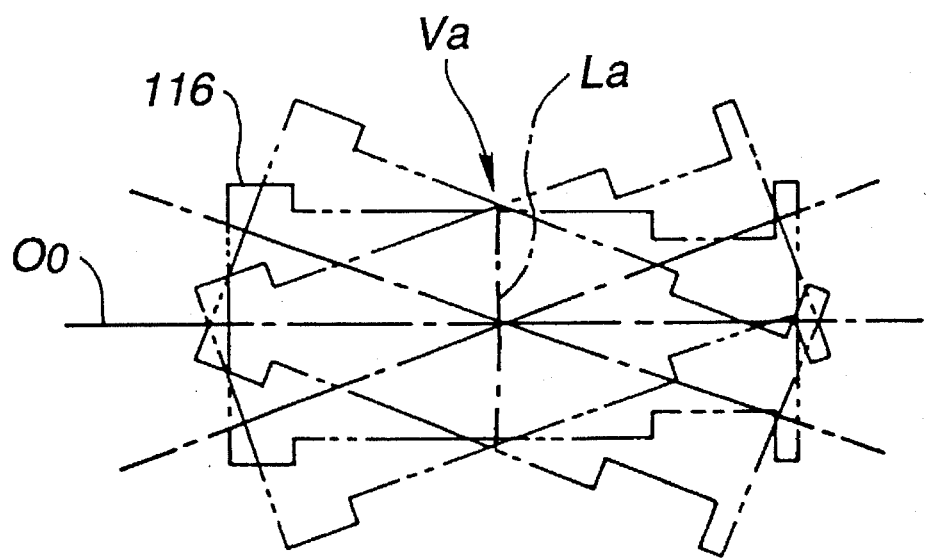
FIG. 58 is a view of the lens frame of FIG. 55 looking in the direction of arrow 58.

FIG. 55 is a plan view of the rotation trajectory of the outline of the lens frame 116 shown in FIG. 54. FIG. 56 is a side view thereof. FIG. 57 is a front view thereof. FIG. 58 is a view of FIG. 55 looking in the direction of arrow 58.

Figure 59:
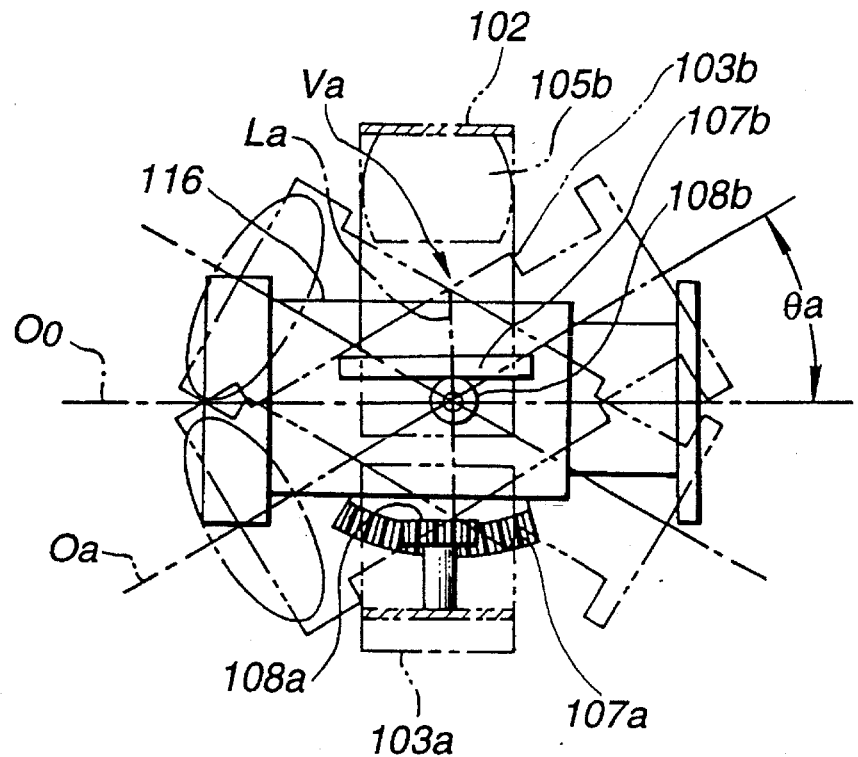
FIG. 59 is a plan view showing the lens frame supporting mechanism of FIG. 37 with a support frame and actuators arranged around the lens frame.
Figure 60:
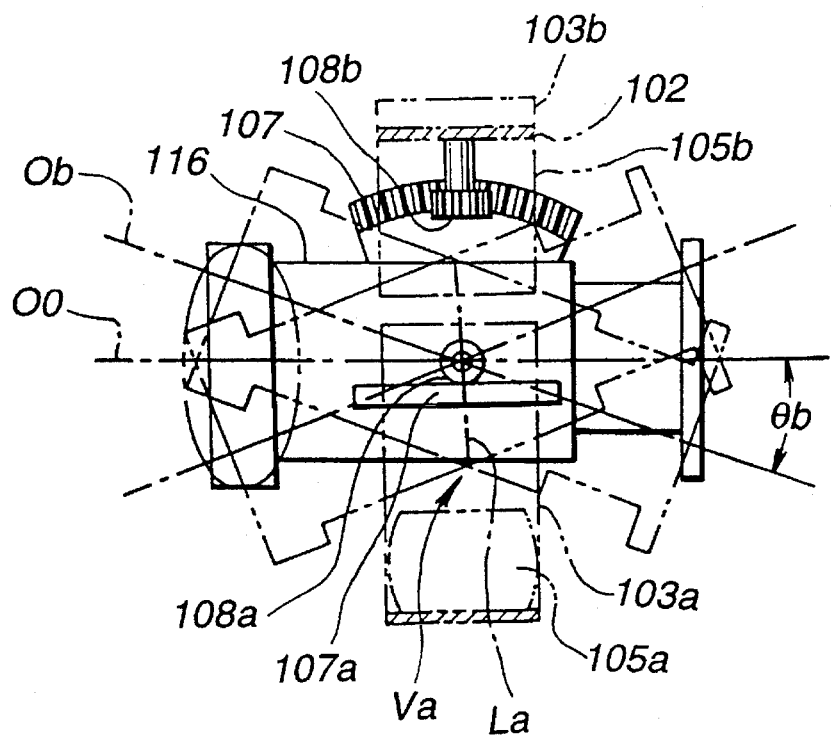
FIG. 60 is a side view showing the lens frame supporting mechanism of FIG. 37 with the support frame and actuators arranged around the lens frame.
Figure 61:
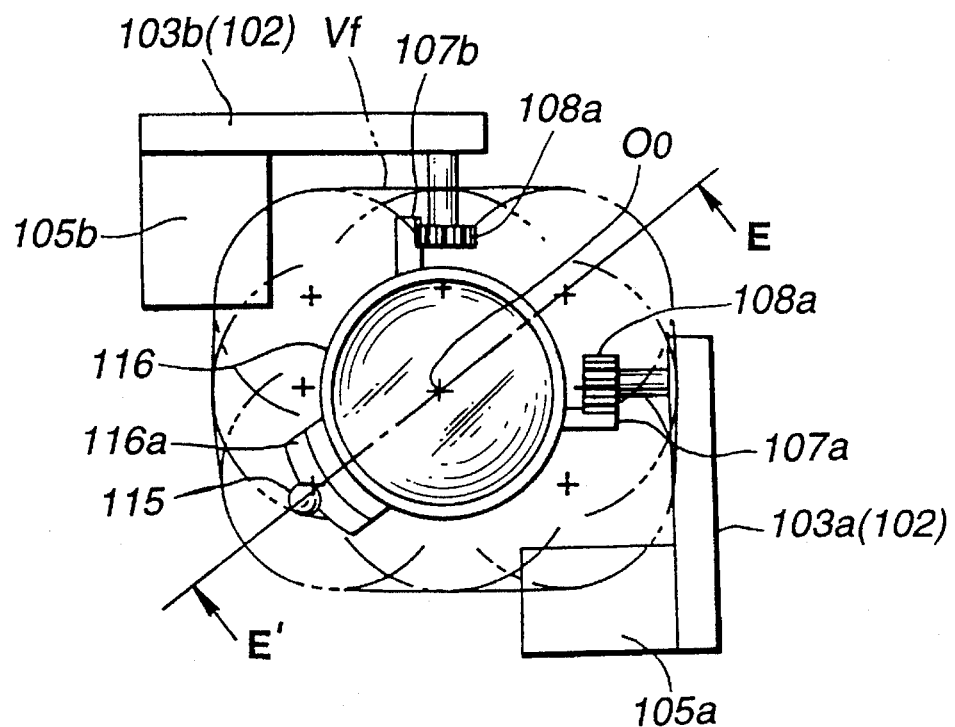
FIG. 61 is a front view showing the lens frame supporting mechanism of FIG. 37 with the actuators arranged around the lens frame.
Figure 62:
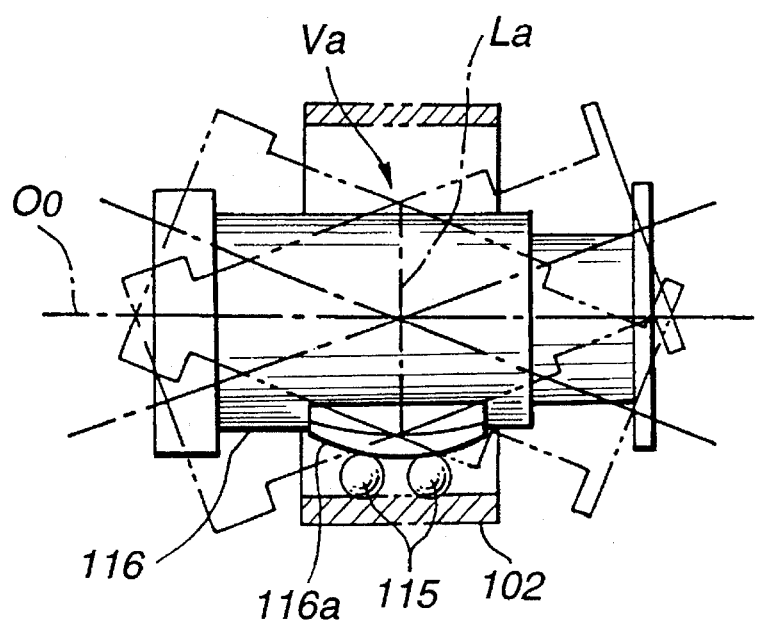
FIG. 62 shows a section of FIG. 61 looking in the direction of arrows 62—62'.

FIGS. 59 to 61 show the rotation trajectory of the outline of the lens frame 116 and the layout of members in this lens frame supporting mechanism. FIG. 59 is a plan view thereof. FIG. 60 is a side view thereof. FIG. 61 is a front view thereof. FIG. 62 is a sectional view of FIG. 61 looking in the direction of arrows 62—62'.

As shown in FIGS. 59 to 61, the support frame 102 is coupled with the major component 10 members in a camera so that it will lie near the trough Va along the trough line La. The drive motors 105a and 105b, and the gear boxes 103a and 103b accommodating the gear arrays 112a and 112b are placed on the circumference of the support frame 102 in the vicinity of the trough Va.

FIG. 61 is a front view showing the state of rotation of the lens frame. FIG. 62 is a sectional view of FIG. 61 looking in the direction of arrows 62—62'. As shown in these figures, the support frame 102 supports the spherical supporting members 115 in the vicinity of the trough Va.

The spherical supporting members 115 are in contact with the spherical bearing 116a of the lens frame 116, thus supporting the lens frame 116. One of the spherical supporting members 115 is constrained to press the spherical bearing 116a by means of a compression spring (not shown). The constraining force of the compression spring helps reduce a backlash occurring when the spherical supporting member 115 supports the lens frame.

As described above, in the lens frame supporting mechanism of this embodiment, the support frame 102, gear boxes 103a and 103b, drive motors 105a and 105b, and spherical supporting members 115 are arranged in the vicinity of the trough Va of the trajectory VO of the outline of the lens frame 116. This structure minimizes dead space and realizes a compact supporting mechanism.

Figure 63:
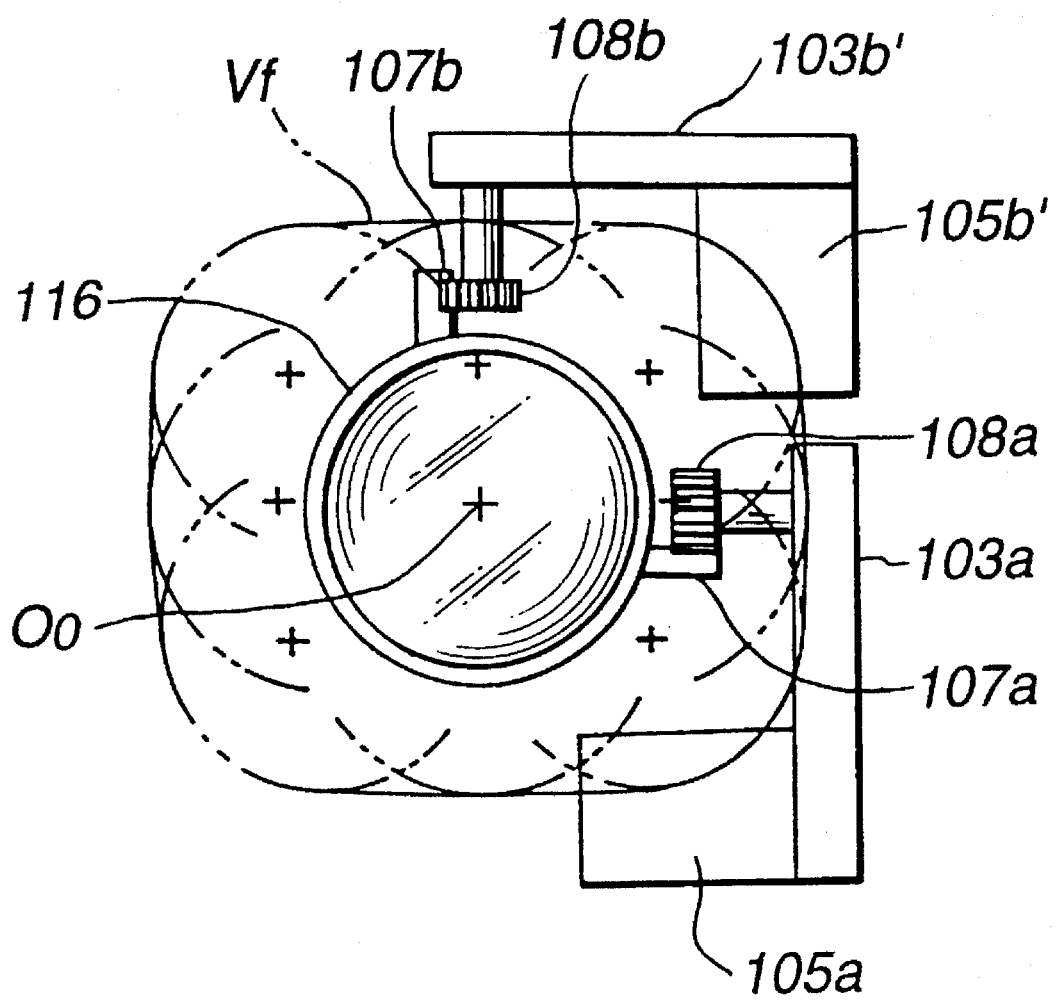
FIG. 63 is a front view showing a variant of the lens frame supporting mechanism of FIG. 37 in which the location of an actuator is modified.

FIG. 63 is a front view showing a variant of the lens frame supporting mechanism of the third embodiment in which the location of the Y-axis actuator is varied. In the supporting mechanism of this variant, the Y-axis actuator; that is, the drive motor 105b' and gear box 103b' are located laterally symmetrically with those in FIG. 61 showing the supporting mechanism of the third embodiment. The layout of this variant can apply when it is more advantageous in terms of the structure of a camera.

Figure 64:
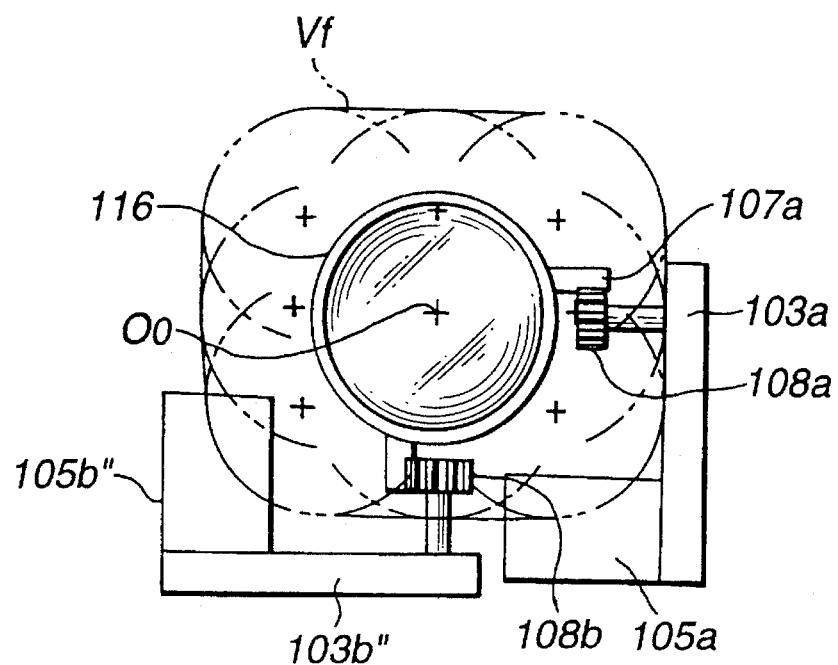
FIG. 64 is a front view showing another variant of the lens frame supporting mechanism of FIG. 37 in which the location of an actuator is modified.

FIG. 64 is a front view showing another variant of the lens frame supporting mechanism of the third embodiment in which the location of the Y-axis actuator is varied. In the supporting mechanism of this variant, the Y-axis actuator; that is, the drive motor 105b' and gear box 103b' are located vertically symmetrically with those in FIG. 61 showing the supporting mechanism of the third embodiment.

Figure 65:
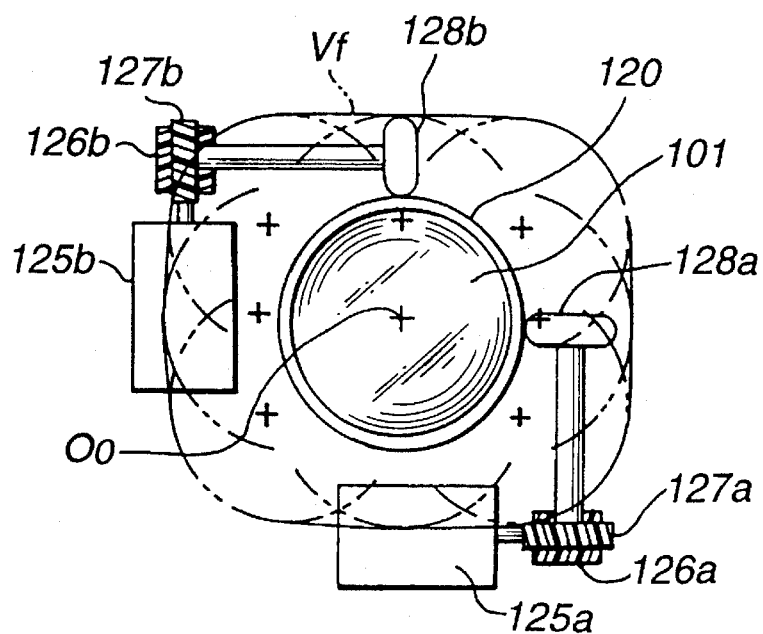
FIG. 65 is a front view showing another variant of the lens frame supporting mechanism of FIG. 37 in which the location of the actuators are modified.

FIG. 65 is a front view showing a variant of the lens frame supporting mechanism of the third embodiment in which the actuators are modified. In this variant, unlike the supporting mechanism of the first embodiment, gears are not employed to rotate a lens frame 120. The lens frame 120 is rotated by means of X- and Y- axis supporting drive wheels 128a and 128b whose outer circumferences are frictional drive surfaces. Specifically, the supporting drive wheels 128a and 128b are rotated while being pressed onto the driven spherical surface on or the friction surface on the outer circumference of the lens frame 120. The lens frame 120 then rotates about the Y and X axes.

The supporting drive wheels 128a and 128b are actuated by drive motors 125a and 125b via reduction gear units composed of worm gears 126a and 127a or screw gears 126b and 127b. The lens frame 120 is driven to rotate with the center of the driven spherical surface as a rotation center. Similar to the supporting mechanism of the first 10 embodiment, even in this embodiment, the drive motors 125a and 125b, screw gears 126a, 127a, 126b, and 127b, and supporting drive wheels 128a and 128b are arranged in the vicinity of the trough of the trajectory of the rotation of the outline of the lens frame. The area occupied by the lens frame supporting mechanism is therefore quite small.

Figure 66:
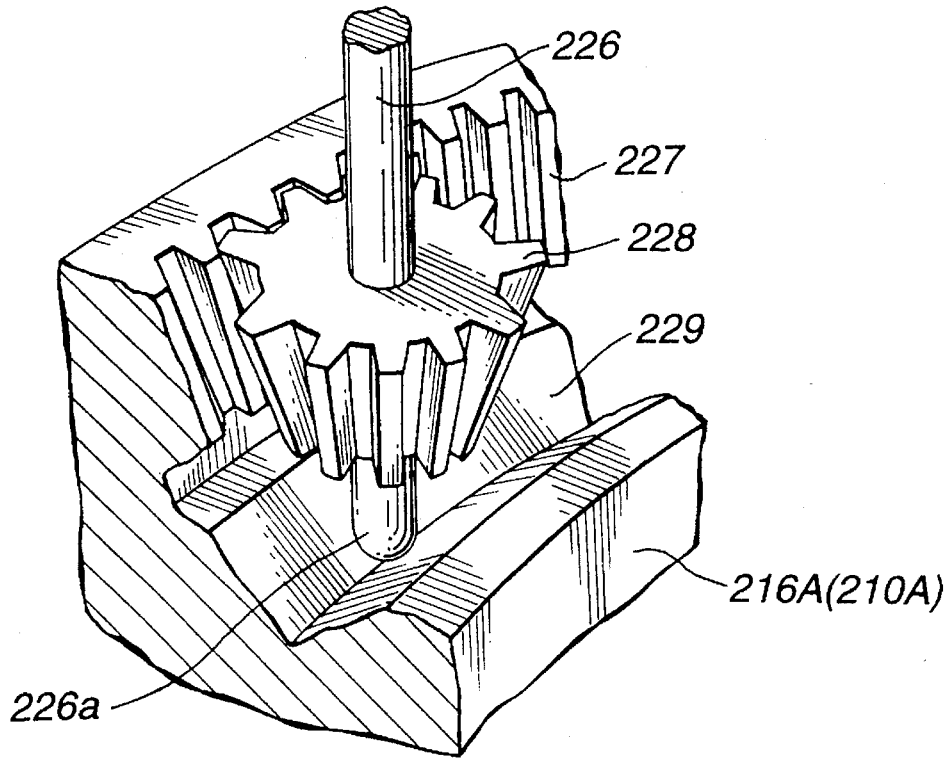
FIG. 66 is an oblique view showing a bevel gear mechanism composed of driving and driven members in a variant of the lens frame supporting mechanism of the third embodiment shown in FIG. 37.
Figure 67:
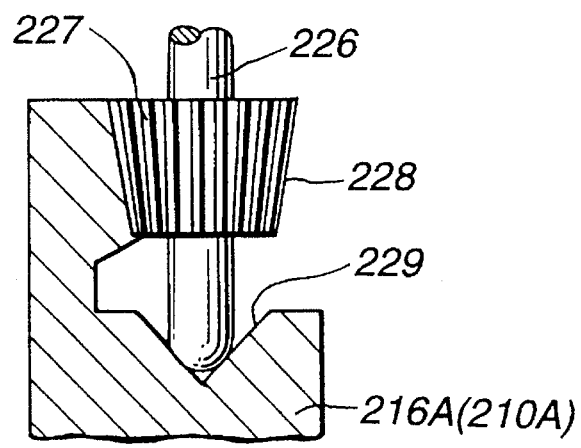
FIG. 67 is a sectional view of the bevel gear mechanism in the variant shown in FIG. 66.

Driving and driven members in a variant of the lens frame supporting mechanism of the third embodiment will now be described. FIGS. 66 and 67 are oblique and longitudinal sectional views, showing a gear mechanism made up of a driving gear and a driven gear in the variant.

In this variant, bevel gears are employed as driving and driven members used to drive and rotate a lens frame 216A. The other components are identical to those of the supporting mechanism of the third embodiment.

In the lens frame in this embodiment, similar to that in the third embodiment, a V-ditch 229 is formed to draw an arc passing through the axis Y and optical O. As shown in the oblique view of FIG. 66 and the partial sectional view of FIG. 67, the spherical tip 226a of the Y-axis drive shaft 226 serving as a driving member is in contact with the V-shaped ditch 229, thus restraining the lens frame 216A from rolling or rotating about the optical axis.

The lens frame 216A, as shown in FIGS. 66 and 67, has a large bevel gear 227, which serves as a driven member and has a circular-shaped arc, whose center coincides with the rotation center G (see FIG. 37), formed along the V-shaped ditch 229. The large bevel gear 227 is engaged with a small bevel gear 228 fixed to the drive shaft 226. When the 10 drive shaft 226 is actuated to rotate, the lens frame 216A rotates about the X axis perpendicular to the Y axis via bevel gears 228, 229.

Referring to FIGS. 66 and 67, the Y-axis rotation drive mechanism has been described. The same structure applies to the X-axis rotation drive mechanism. In the X-axis rotation drive mechanism, the small bevel gear is fixed to the X-axis drive shaft and the large bevel gear is formed in an independent rotary member 210A.

As described above, in the lens frame supporting mechanism of this embodiment, bevel gears are employed as driving and driven members. Driving force can therefore be transmitted efficiently. The gears hardly cause a backlash. The lens frame can therefore be driven to rotate with high precision.

Figure 68:
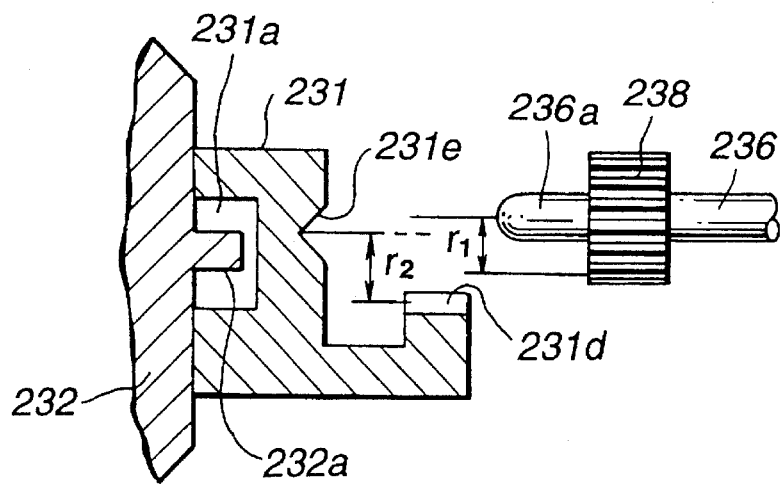
FIG. 68 is a sectional view showing a variant of the independent rotary member in the lens frame supporting mechanism of the third embodiment in FIG. 37.

Next, a variant of the independent rotary member in the lens frame supporting mechanism of the third embodiment will be described. In this variant, as shown in the exploded oblique view of FIG. 68 and the sectional view of FIG. 69, even when the center of a drive shaft 236 of an X-axis actuator, which comes into contact with an independent rotary member 231, is inconsistent with the center of a pin 232a on a lens frame 232, the independent rotary member 231 absorbs the inconsistency and thus enables centering drive.

Figure 69:
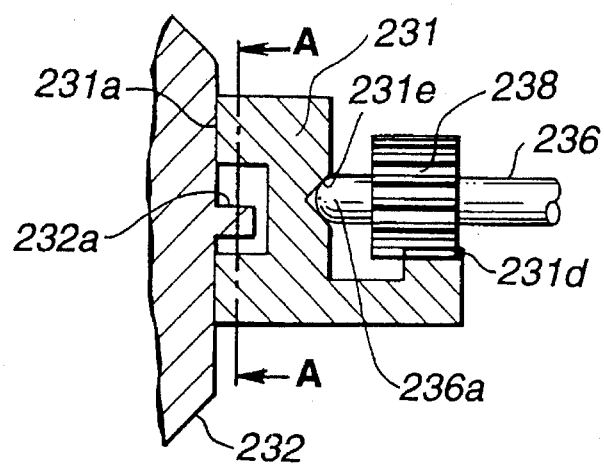
FIG. 69 is a sectional view showing the variant of the independent rotary member shown in FIG. 68.
Figure 70:
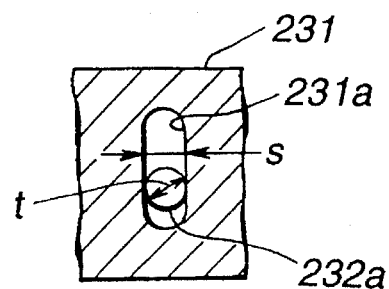
FIG. 70 shows a section of FIG. 69 looking in the direction of arrows 70—70'.
Figure 71:
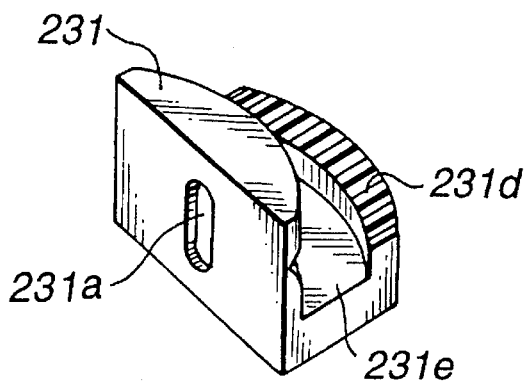
FIG. 71 is an oblique view showing the variant of the independent rotary member shown in FIG. 68.
Figure 72:
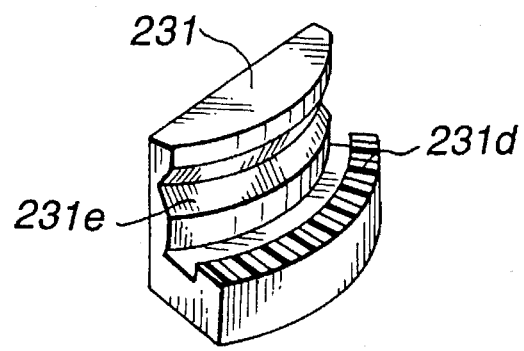
FIG. 72 is another oblique view showing the variant of the independent rotary member shown in FIG. 68.
Figure 73:
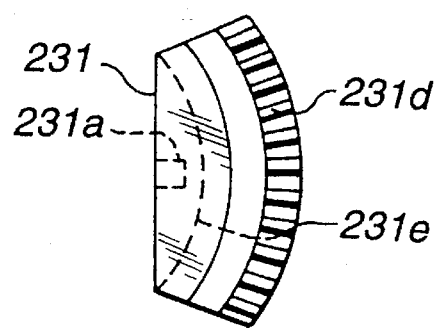
FIG. 73 is a plan view showing the variant of the independent rotary member shown in FIG. 68.

FIG. 70 is a sectional view of FIG. 69 looking in the direction of arrows 70—70'. FIGS. 71 and 72 are different oblique views of the independent rotary member 231. FIG. 73 is a plan view thereof. The independent rotary member 231 has a V-shaped ditch 231e and a face gear 231d similar to that shown in the third embodiment. A driving 10 gear 238, which is a spur gear arranged to engage the face gear 231d, is fixed to a drive shaft 236 whose spherical tip 236a comes into contact with the V-shaped ditch 231e. The other components are identical to those in the first embodiment.

The centering drive structure of the independent rotary member 231 will now be described. As shown in FIGS. 68 to 71, an elongated hole 231a having a width S and serving as a centering drive guide is formed in the part of the independent rotary member 231 in contact with a lens frame 232. The longitudinal direction of the elongated hole 231a is perpendicular to the direction in which the V-shaped ditch 231e is extending.

A pin 232a is formed on the lens frame 232. The pin 232a has a diameter t and is fitted in the elongated hole 231a. The pin 232a is located on the X axis of the lens frame.

As shown in FIG. 69, the pin 232a on the lens frame 232 is fitted into the elongated hole 231a in the independent rotary member 231. The independent rotary member 231 is thus mounted on the lens frame 232. In this state, the independent rotary member 231 is rotatable relative to the lens frame 232 and movable in a direction traversing the V-shaped ditch 231a. The spherical tip 236a of the drive shaft 236 abuts the V-shaped ditch 231e.

In the course of the above assembling, the independent, rotary member 231 is restrained from moving along the X axis. When the drive shaft 236 abuts V-shaped ditch 231e, the position of the independent rotary member 231 in the direction traversing the V-shaped ditch 231a is aligned. Owing to the alignment of the independent rotary 10 member 231 in the direction traversing the V-shaped ditch 231a, even if the drive shaft 236 and the pin 232a of the lens frame 232 mismatch, the X-axis actuator need not be re-aligned but can be mounted on the lens frame 232 with the independent rotary member 231 between them. The driving gear 238 is then engaged with the face gear 231d. The lens frame 232 is thus rotatable. In the process of assembling the actuator and lens frame, if the elongated hole 231 does not have an elongated shape but has a circular shape, the rotation center of the lens frame 232 must be aligned with the center of the drive shaft 236. Moreover, the radius r1 of the pitch circle of the driving gear 238 (see FIG. 68) must agree with the space r2 from the center of the V-shaped ditch 231e to the pitch circle of the face gear 231d (see FIG. 68). In short, the X-axis actuator must be aligned.

In this embodiment, as described above, the elongated hole 231a is formed in the independent rotary member 231. Therefore, even if the aforesaid inconsistency is present, alignment need not be done. On the contrary, the inconsistency can be absorbed during assembling. The driving gear 238 and face gear 231 are perfectly engaged with each other. Smooth drive is thus enabled.

Next, another variant of the independent rotary member in the lens frame supporting mechanism of the third embodiment will be described. In this variant, as shown in the oblique view of FIG. 74, ribs 241b and 241c are formed on the surface of an independent rotary member 241 in contact with a lens frame, so that the independent rotary member will always be in stable contact with the lens frame with little frictional resistance in the contact surface 10 of the lens frame.

Figure 75A:
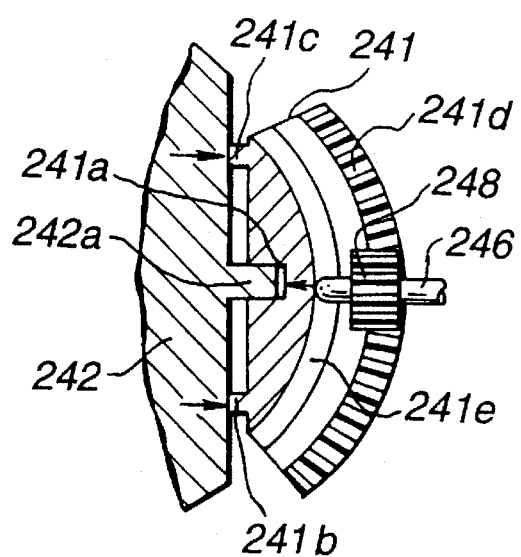
FIGS. 75A and 75B are sectional views showing the variant of the independent rotary member shown in FIG. 74, wherein the drive shaft is located at the center of the drive zone and at an edge of a drive zone.
Figure 75B:
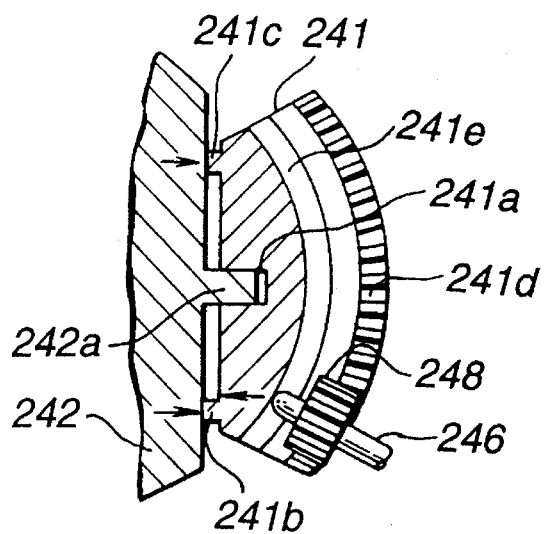

As shown in FIGS. 75A and 75B or the sectional views of the states of working of the independent rotary member, when the independent rotary member 241 is mounted on a lens frame 242, a guide pin 242a on the lens frame 242 is fitted into a support hole 241a formed in the rotation center of the independent rotary member 241. The tip of a drive shaft 246 abuts on a V-shaped ditch 241e of the rotary member 241. The ribs 241b and 241c thus come into contact with the lens frame 242. The frictional resistance caused by the rotary member 241 is therefore limited, thus enabling stable rotation.

FIGS. 75A and 75B are sectional views showing the states of rotation of a driving gear 248 and a face gear 241d that are located at different relative positions. In FIG. 75A, the driving gear 248 is located at neutral position on the face gear 241d. In FIG. 75B, the driving gear 248 has rotated to the lower end of a movable zone on the face gear 241d.

In the state in FIG. 75A, substantially uniform constraining force works on both of the ribs 241b and 241c. The independent rotary member 241 is therefore supported by the lens frame 242 in a stable manner. In FIG. 75B, the drive shaft 246 is located at one end of the rotary member 241. Even in this state, since the drive shaft 246 lies within a zone defined by the ribs 241b and 241c, repulsion applied to the ribs 241b and 241c will never die out. The independent rotary member 241 is therefore supported by the lens frame 242 in a stable manner. This is because the ribs 241b and 241c are located at both ends of the independent rotary member 241.

Figure 76A:
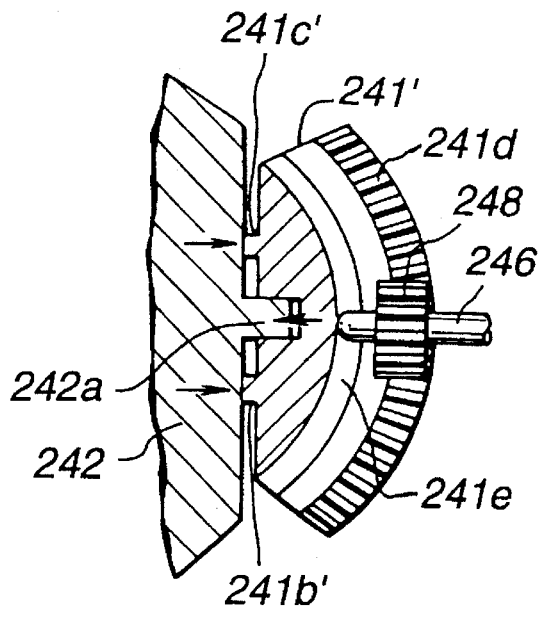
FIG. 76A is a sectional view showing the variant of the independent rotary member shown in FIG. 74, wherein projections are located inappropriately, and wherein the drive shaft is located at a neutral position.
Figure 76B:
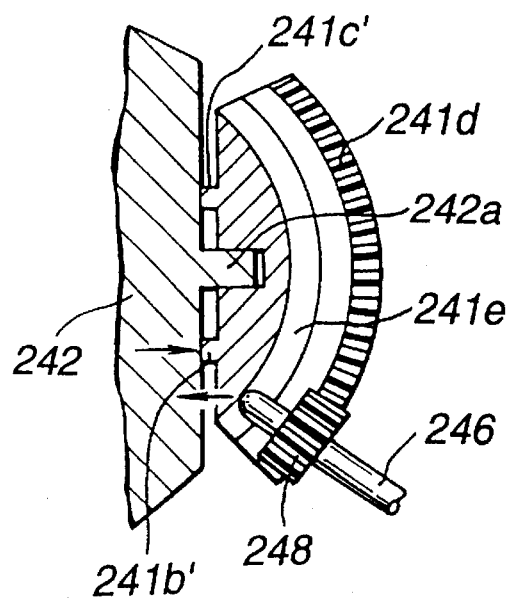
FIG. 76B is a sectional view showing the variant of the independent rotary member shown in FIG. 74 wherein projections are located inappropriately and wherein the drive shaft is located at an edge of a drive zone.

As shown in FIGS. 76A and 76B or the sectional views of different workings states, when ribs 241b' and 241c', serving as supporting members, are located near the center of a rotary member 241', as long as the drive shaft is located at the neutral position, as shown in FIG. 76A, no problem occurs. However, when the drive shaft 246 is located at an end of a working zone, the abutting force of the drive shaft 246 works on the outside of the rib 241b'. In this state, a moment clockwise rotation works on the independent rotary member 241' to jerk the other end of the independent rotary member 241'. That is to say, the independent rotary member 241' is not supported by the lens frame 242 in a stable manner.

A permissible location of the rib 241b on the independent rotary member 241 will be described below.

Figure 77:
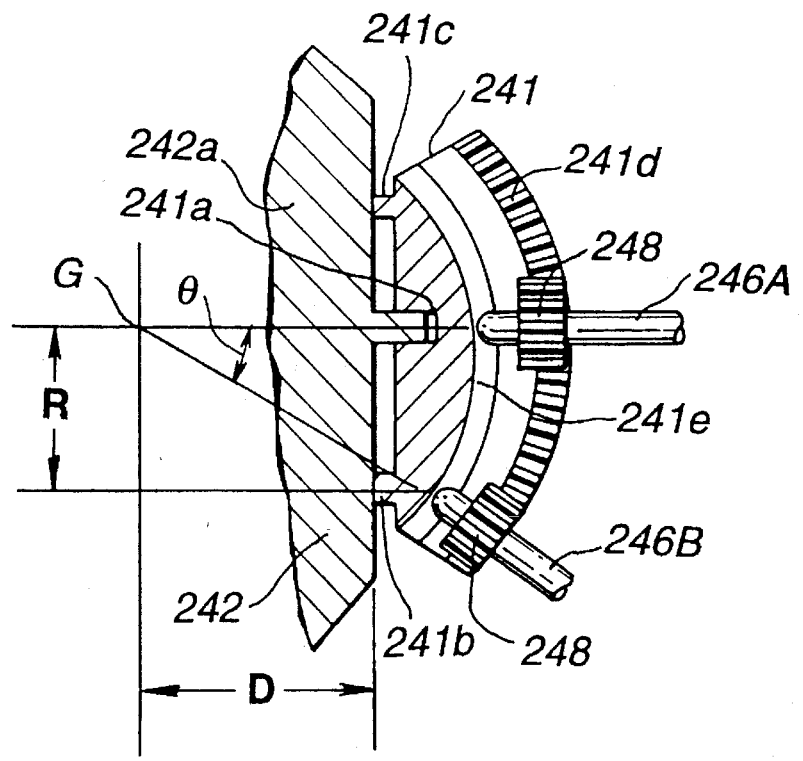
FIG. 77 is a sectional view showing the variant of the independent rotary member shown in FIG. 74, which is used to calculate permissible locations of the projections.

In FIG. 77 or the sectional view of the independent rotary member 241, the drive shaft 246 is located at a neural position 246A and a limit position 246B of a rotation range. A distance between the centers of the rib 241b and the support hole 241a must satisfy the formula below.

$$R > D - \tan\theta \quad (1)$$

Herein, D is a distance between the rotation center G of the lens frame and the contact surface thereof. 8 denotes an angle formed by the pin 241a and the drive shaft 246, which is located that the limit position 246B, with respect to the rotation center G.

As described above, when the independent rotary member 241 of this variant is employed, since the independent rotary member 241 is supported by the lens frame 242 with precision, high-precision rotation drive is enabled.

Figure 74:
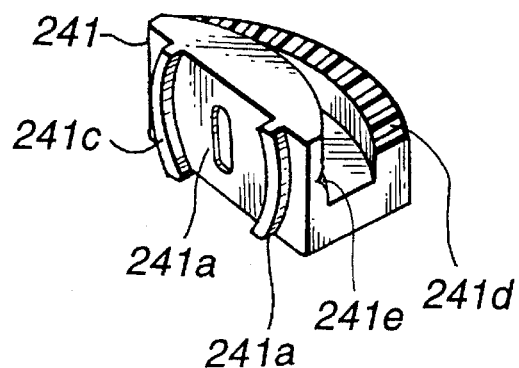
FIG. 74 is an oblique view showing another variant of the independent rotary member in the lens frame supporting member of the third embodiment shown in FIG. 37.
Figure 78:
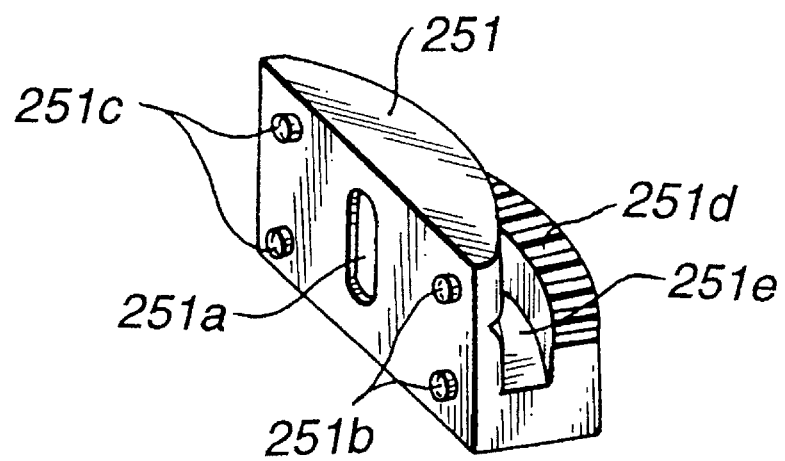
FIG. 78 is an oblique view showing another variant of the independent rotary member in the lens frame supporting mechanism of the third embodiment shown in FIG. 37.
Figure 79:
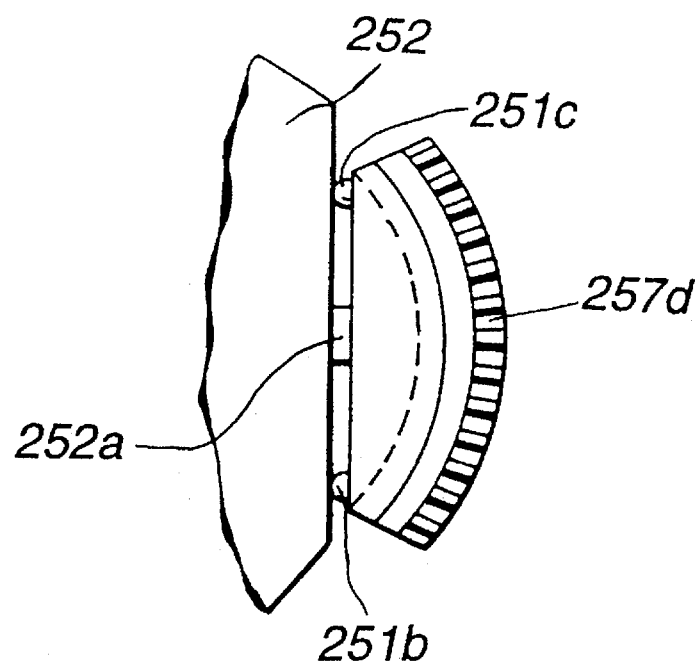
FIG. 79 is a plan view showing the variant of the independent rotary member shown in FIG. 78.
Figure 80:
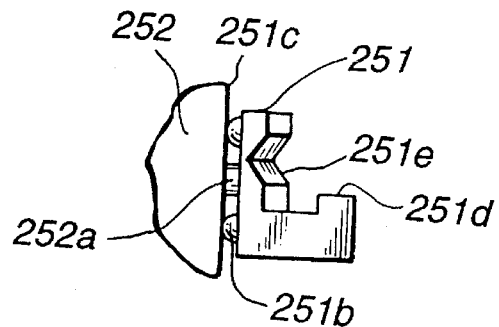
FIG. 80 is a side view showing the variant of the independent rotary member shown in FIG. 78.

Next, another variant of the independent rotary member in the lens frame supporting mechanism of the third embodiment will be described. In this variant, instead of the ribs 241b and 241c, which are shown in FIG. 74, serving as supporting members for allowing the independent rotary member to stay in stable contact with the lens frame, four pins made up of pin pairs 251b and 251c, are formed on an independent rotary member 251 as shown in the oblique view of FIG. 78. FIG. 79 is a plan view of the independent rotary member 251 that is mounted on the lens frame. FIG. 80 is a side view thereof.

The independent rotary member 251 of this variant has a face gear 251d and a V-shaped ditch 251e similar to the third embodiment. Moreover, as shown in FIG. 78, an elongated hole 251a, which serves as a centering drive guide described in conjunction with FIG. 74, is formed in a direction perpendicular to the V-shaped ditch 251e. A support pin 252a, which is to be fitted into the elongated hole 251a so as to slide freely therein, is located on the X axis of a lens frame 252 on which the independent rotary member 251 is mounted.

In this variant, the pins 251b and 251c serving as supporting members are installed at four corners. This structure further improves the state of the independent rotary member 251 mounted on the lens frame 252. Rotation with least frictional resistance is thus enabled. Furthermore, the rotation centers of the independent rotary member 251 and lens frame 252 are aligned with each other while being driven. This results in easy 10 assembling.

Figure 81:
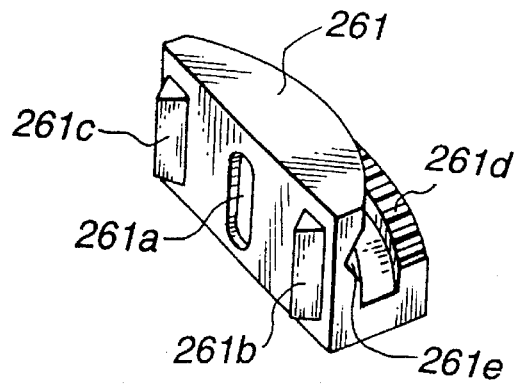
FIG. 81 is an oblique view showing yet another variant of the independent rotary member in the lens frame supporting mechanism of the third embodiment shown in FIG. 37.
Figure 82:
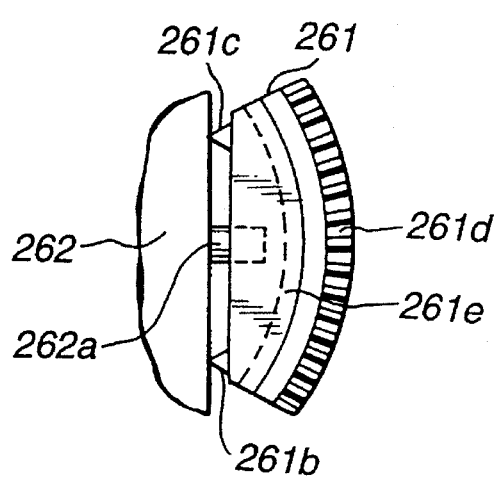
FIG. 82 is a plan view showing the independent rotary member shown in FIG. 81.

Next, another variant of the independent rotary member in the lens frame supporting mechanism of the third embodiment will be described. In this variant, instead of the ribs 251b and 251c, which are shown in FIG. 74, serving as supporting members for allowing the independent rotary member to stay in stable contact with the lens frame all the time, ribs 261b and 261c each having a triangular cross section are formed on an independent rotary member 261 as shown in the oblique view of FIG. 81. FIG. 82 is a plan view of the independent rotary member 261 mounted on the lens frame.

The independent rotary member 261 of this variant has a face gear 261d and a V-shaped ditch 261e similar to that shown in the third embodiment. An elongated hole 261a serving as a centering drive guide is formed in a direction perpendicular to the V-shaped ditch 261e. A support pin 262a, which is fitted into the elongated hole 261a, is formed on a lens frame 262 on which the independent rotary member 261 is mounted.

In this variant, since the triangular ribs 261b and 261c are formed as supporting members in two places, rotation with least frictional resistance is enabled. Moreover, since the rotation centers of the independent rotary member 261 and lens frame 262 are aligned with each other while being driven, assembling can easily be done.

Figure 83:
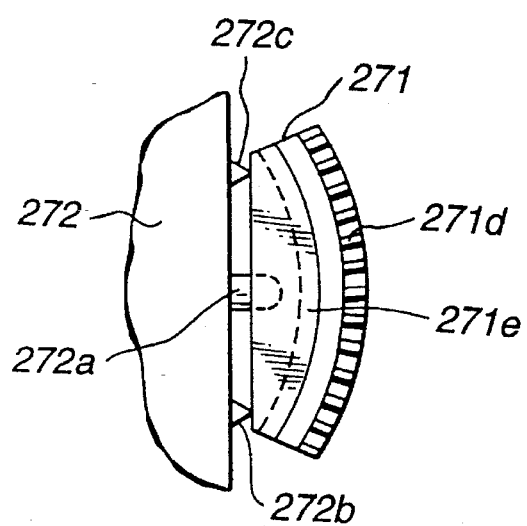
FIG. 83 is a plan view showing still another variant of the independent rotary member in the lens frame supporting mechanism of the third embodiment shown in FIG. 37.

Next, another variant of the independent rotary member in the lens frame supporting mechanism of the third embodiment will be described. In this variant, as shown in the plan view of FIG. 83 or in which an independent rotary member is mounted on a lens frame, instead of the ribs 241b and 241c in 10 FIG. 81 that serve as supporting members to allow an independent rotary member to stay in stable contact with a lens frame all the time and that rest on the independent rotary member 261, ribs 272b and 272c, each having a triangular cross section, are formed on a lens frame 272.

A support pin 272a, which is fitted into an independent rotary member 271, is formed on the lens frame 272. The independent rotary member 271 has a face gear 271d and a V-shaped ditch 271e.

In this variant, the independent rotary member 271 has a simple shape. Rotation with least frictional resistance is enabled.

Next, a lens frame supporting mechanism of the fourth embodiment of the present invention will now be described.

In general, a decelerator must be included in a power transmission mechanism for driving a lens frame. If reduction gears are employed as the decelerator, a backlash caused by the reduction gears is inevitable. The backlash triggers a mechanical delay in response. A backlash occurring when a motor is stopped brings about a "sway" in imaging.

Accordingly, this embodiment provides a lens frame supporting mechanism that is unaffected by backlash occurring when a lens frame is rotated or stopped, that can rotate the lens frame without backlash despite the employment of a decelerator, and that causes neither mechanical delay in response nor a sway in imaging.

Figure 84:
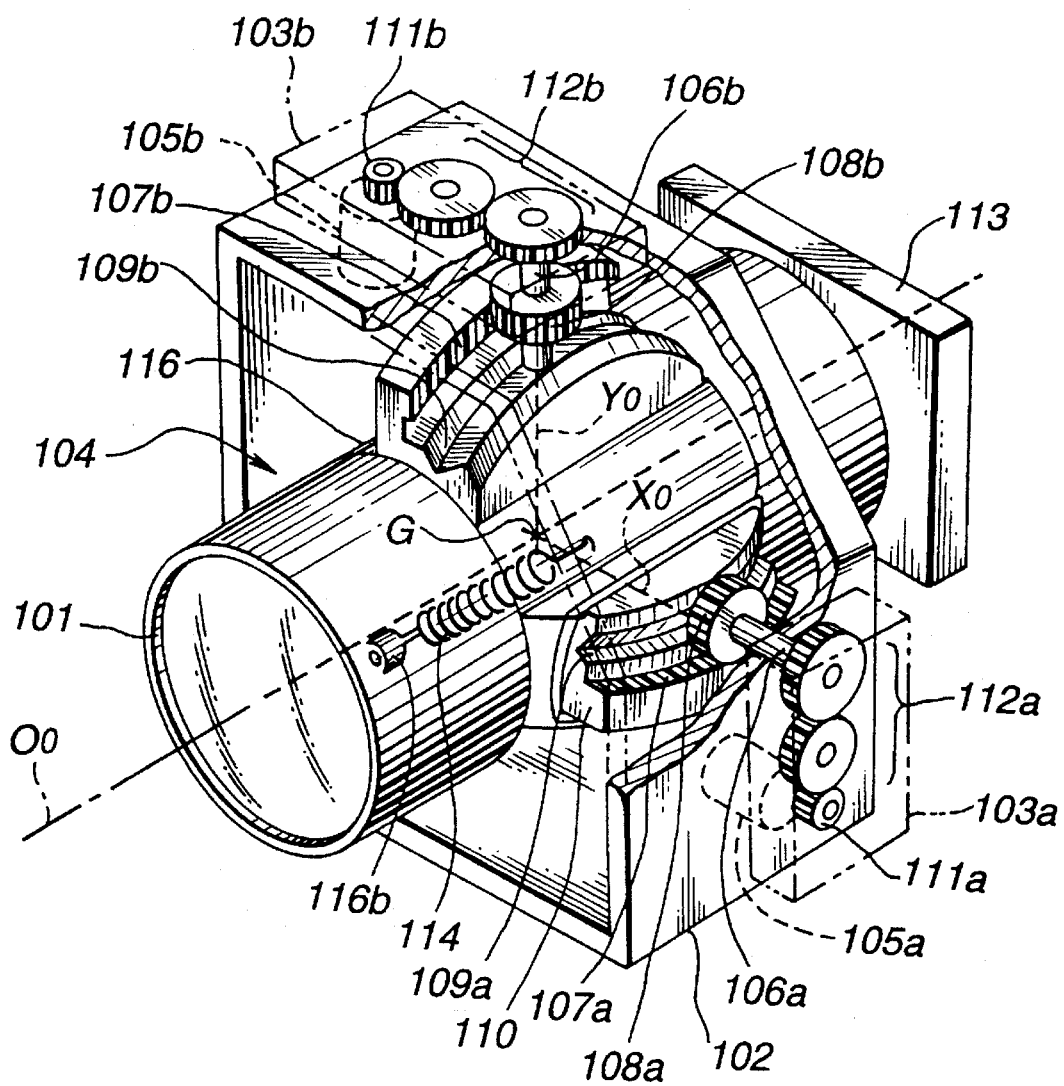
FIG. 84 is an oblique view showing a major portion of a lens frame supporting mechanism representing a fourth embodiment of the present invention.

The lens frame supporting mechanism of the fourth embodiment, as shown in the oblique view of FIG. 84, drives and rotates a lens frame 116 of a lens barrel unit 104 encased in a support frame 102 horizontally and vertically. A lens frame offset spring 114 serving as a constraining means is strung over the lens frame 116. The other components are identical to those of the lens frame supporting mechanism of the third embodiment, of which description will be omitted for simplicity.

Figure 85:
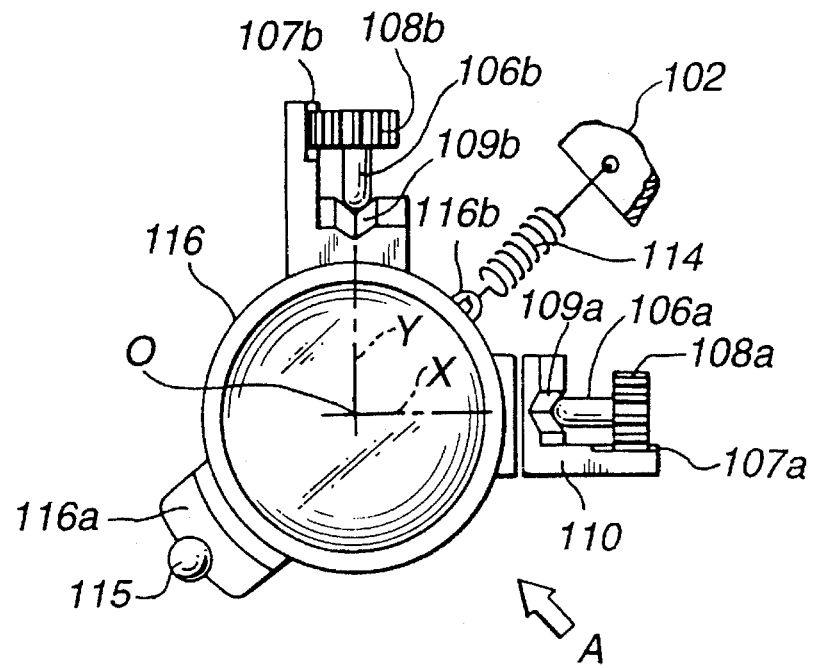
FIG. 85 is a front view showing a major portion of a lens barrel unit in the lens frame supporting mechanism shown in FIG. 84.
Figure 86:
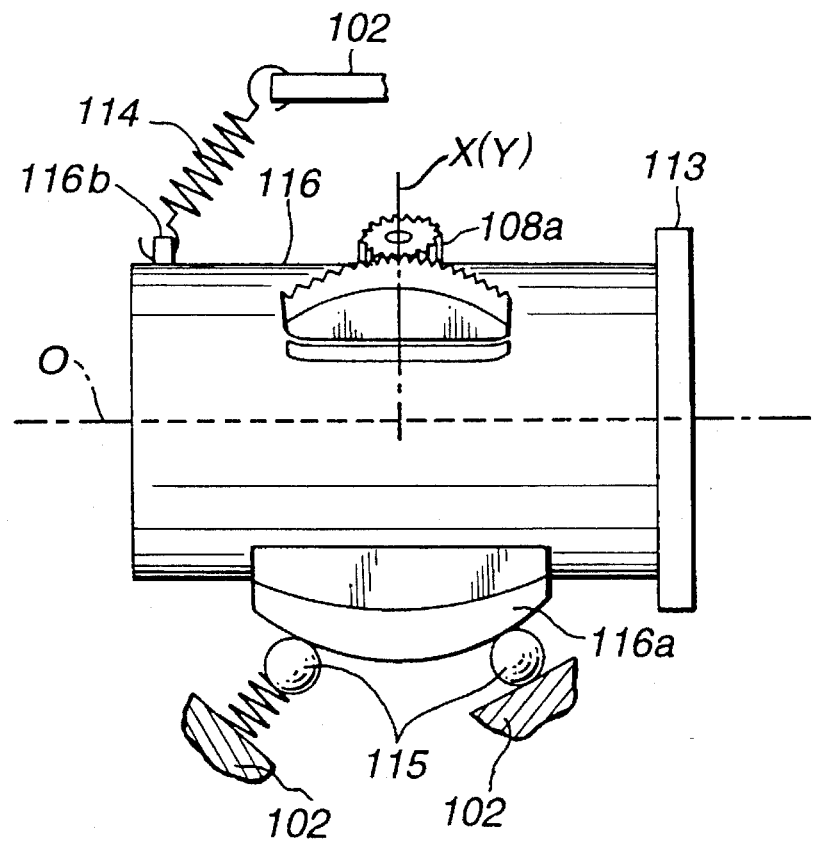
FIG. 86 is a view of FIG. 85 looking in the direction of arrow 86.

FIG. 85 is a front view of the lens frame supporting mechanism, and FIG. 86 is a view of FIG. 85 looking in the direction of arrow 86. As shown in these drawings, a spherical member 116a is formed in the center of the part of the lens frame 116 opposed to the part thereof staying in contact with the drive shafts 106a and 106b. The spherical member 116a is supported by the spherical supporting members 115 that are supported by the support frame 102 and remain substantially in point contact with the support frame 102. One of the spherical supporting members 115 is constrained to press the spherical member 116a by means of a compression spring. The supporting member 115 thus hardly causes a backlash because of the constraining force of the compression spring.

The lens frame 116 has a spring hook receiving opening 116b oriented toward halving the first quadrant that, when the lens frame 116 lies at the neutral position, is defined with the X and Y axes. A spring hook receiving opening 102a is formed on the support frame 102 and is opposed to one spring hook receiving opening 116b. A lens frame offset spring 114, which serves as a constraining means and is formed as an extension spring, is strung between the spring hook receiving openings which respectively receive spring hooks 114a and 114b. The lens frame 116 is therefore applied the constraining force oriented toward substantially halving the first quadrant formed by the X and Y axes.

The offset spring 114 may alternatively be a compression spring. The position of stringing the spring 114 is not limited to the part of the lens frame having the spherical member 116a or facing an object but may be located in the part thereof facing an imaging device.

Figure 87:
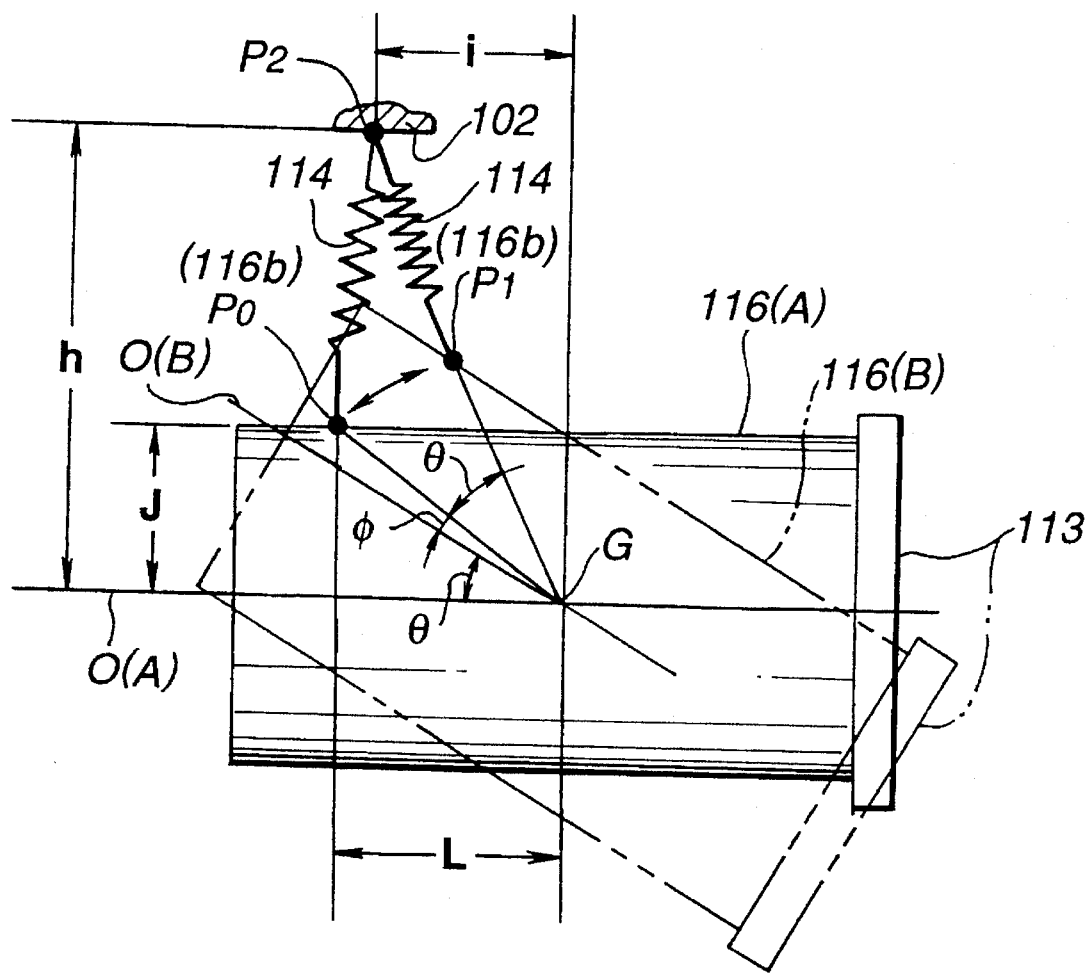
FIG. 87 shows a transition of a working position of an offset spring resulting from the rotation of the lens frame in the lens frame supporting mechanism in FIG. 84.

Next, the rotating operation of the lens frame supporting mechanism of this embodiment having the aforesaid structure will now be described in conjunction with FIGS. 84 to 86. Referring to FIG. 87 for explaining operation, the effect of the offset spring 114 will be described in detail as follows.

When the drive motor 105a and/or 105b is actuated, the lens frame 116 staying in the neutral state shown in FIG. 84 is driven to rotate about the X and/or Y axis by means of the X- and/or Y-axis actuator. The optical O thereof shifts. During the rotation, since the independent rotary member 110 is rotatable relative to the lens frame 116 as described previously, the engagements between the driving gear 108a and face gear 107a and between the driving gear 108b and face gear 107b remain normal.

In the lens frame supporting mechanism of this embodiment, the offset spring 114 exerts a constraining force on the lens frame 116 in a direction of substantially halving the first quadrant defined by the XO and YO axes. The constraining force induces a moment of rotation. The lens frame 116 is therefore rotated with a backlash occurring between the drive motor 105a and face gear 107a minimized and with a backlash occurring between the drive motor 105b and face gear 107b minimized. The lens frame 116 therefore rotates to a predetermined after-rotation position with higher precision. At the same time, a delay by which the lens frame 116 delays in starting rotation is minimized to ensure smooth response of the lens frame 116.

The relationships between the position of stringing the lens frame offset spring 114 and the rotation range of the lens frame 116 will now be described.

FIG. 87 is a view, similar to FIG. 86, which is a view of FIG. 85 looking in the direction of arrow 86, showing the transition of a working position of the offset spring 114 during rotation of the lens frame 116. One end of the offset spring 114 is hooked at a spring hook receiving position P2 in the support frame 102, while the other end thereof is hooked by the spring hook receiving portion 116b at position P1 in the lens frame 116.

When the lens frame 116 is at a neutral position 116(A), the spring hook 116b is located at a position P0. When the lens frame 116 rotates by an angle and moves to an after-rotation position 116(B) that is a limit of rotation, the spring hook 116b shifts to a position P1. The optical O of the lens frame shifts from a direction O(A) to a direction O(B). Even in this state, the condition set forth below must be satisfied so that a moment of clockwise rotation in FIG. 87 will be applied to the lens frame 116. That is to say, $$i/h > \tan((\chi/2) - 2\theta - \phi) \quad (2)$$

where, $\phi$ is equal to (arc tan (j/L))–$\phi$. The other variants are defined as follows:

i: a distance from a plane perpendicular to the neutral reference optical OO passing through the rotation center G to the spring hook position P2 on the support frame 102.

h: a distance from the neutral reference optical OO to the spring hook position P2 on the support frame 102 j: a distance from the neutral reference optical OO to the spring hook 116b on the lens frame 116

L: a distance from the plane perpendicular to the neutral reference optical OO passing through the rotation center G to the spring hook 116b on the lens frame 116.

When the offset spring 114 is strung between the lens frame 116 and support frame 102 in such a manner that the formula (2) will be satisfied, the moment of clockwise rotation in FIG. 87 always works on the lens frame 116. The lens frame 116 can therefore be driven to rotate without causing a backlash between gears or in a driving force transmission mechanism.

As described above, since the lens frame offset spring 114 is hooked on an appropriate position on the lens frame 116, the lens frame supporting mechanism of this embodiment can apply constraining force, which is oriented in a specified direction, to the lens frame all the time. When the lens frame rotates or stops, a backlash hardly occurs. Even if a decelerator is included in an
is actuator, rotation drive without backlash
in enabled. Occurrence of a mechanical delay response or a sway in imaging can be minimized. If the offset spring 14 is hooked on the position specified in this embodiment, backlash can be effectively absorbed, and an increase in a load to a drive motor can be suppressed as much as possible.

Next, a lens frame supporting mechanism of the fifth embodiment of the present invention will now be described.

The lens frame supporting mechanism of this embodiment, similar to those of the aforesaid embodiments, can apply to an image pickup dedicated to hand tremor compensation or dynamic lock-on for a camera-inclusive VTR or the like.

Figure 88:
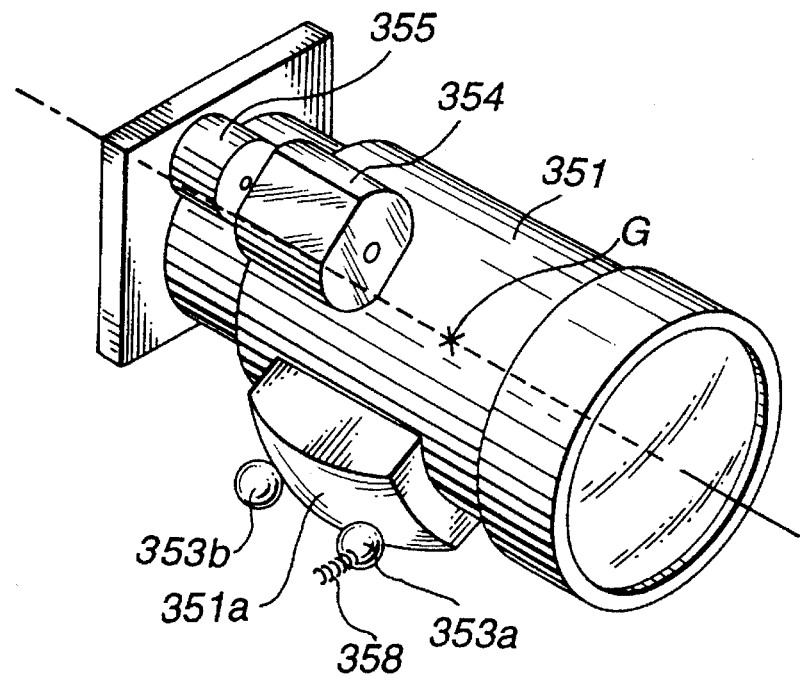
FIG. 88 is an oblique view showing a major portion of a lens barrel unit in a lens frame supporting mechanism representing a fifth embodiment of the present invention.
Figure 89:
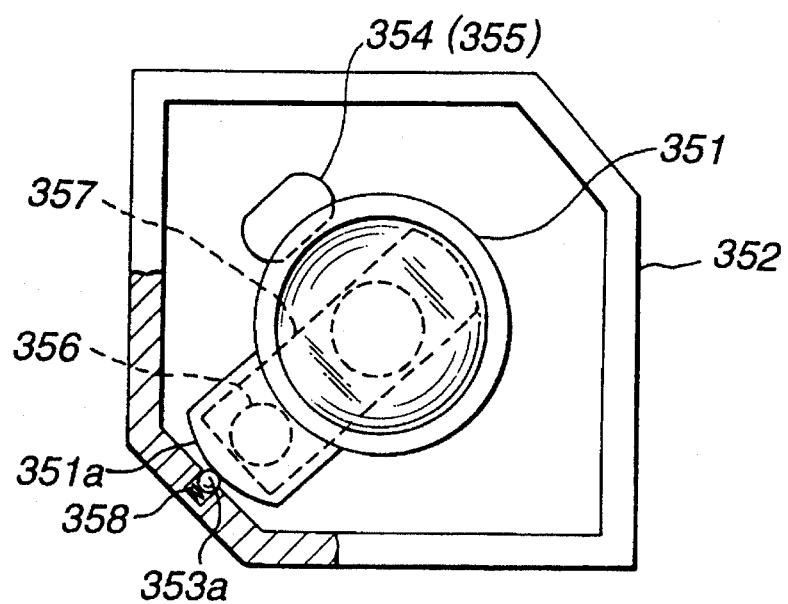
FIG. 89 is a front view showing the lens frame supporting mechanism shown in FIG. 88.

FIG. 88 is an oblique view of the lens frame supporting mechanism of this embodiment. FIG. 89 is a front view thereof. As shown in these figures, similar to the supporting mechanism of the third embodiment, a lens frame 351 of a lens barrel unit, which is encased in a support frame 352 that is a lens frame supporting structure member or a frame member, is rotated horizontally or vertically with the rotation center G as a center using the X- or Y-axis actuator.

FIG. 88 is an oblique view showing the lens barrel unit and FIG. 89 in a front view thereof. As shown in these figures, in the supporting mechanism of this embodiment, a zoom motor 354 and a focus motor 355, which are used to drive a lens, are secured on the lens frame 351 inside the support frame 352. Either one of a single or a plurality of spherical supporting structures 351a, each of which is a bump for supporting a rotating lens frame and has the spherical center aligned with the rotation center G, are formed on the side surface of the lens frame 351 opposed to the side surface thereon on which the actuators are located.

An iris unit 357 including an iris actuator 356 for driving optical elements is incorporated in the spherical supporting structure 351a. Spherical supporting members 353a and 353b are in point contact with the spherical supporting structure 351a. The lens frame 351 rotates with the rotation center G as a center while being supported by the spherical supporting members 353a and 353b staying in point contact with the lens frame 351. A compression spring 358 exerts a constraining force on the spherical supporting member 353a.

As described above, according to the supporting mechanism of this embodiment, the zoom motor 354 and focus motor 355 are encased in the support frame 352. The actuator 356 for the iris unit 357 is incorporated in the bump-like spherical supporting structure 351a. No component member is therefore projecting from the outline of the support frame 352. Thus, a small rotatable lens frame mechanism can be realized. Moreover, a compact camera with hand tremor compensation and dynamic lock-on facilities or a tilt facility can be constructed.

Next, a lens frame supporting mechanism of the sixth embodiment of the present invention will now be described.

Figure 90:
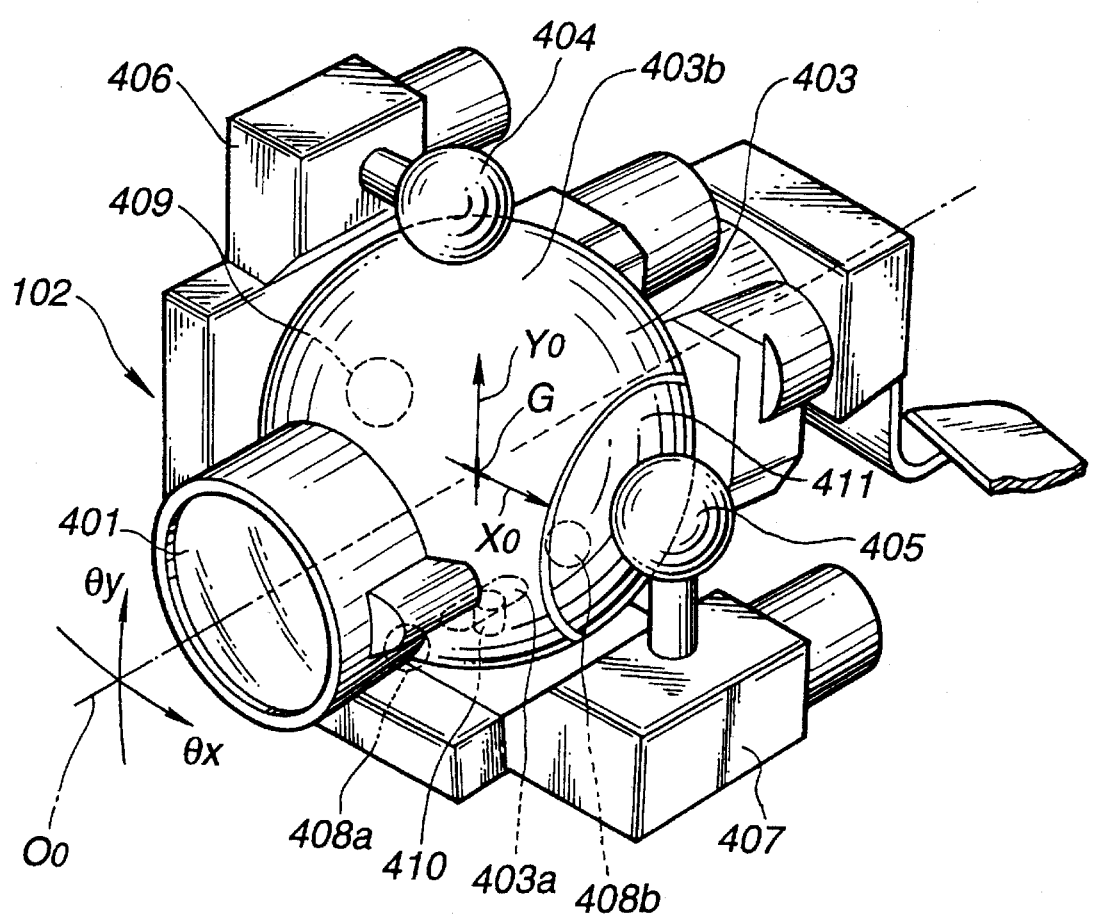
FIG. 90 is an oblique view showing a major portion of a lens frame supporting mechanism representing a sixth embodiment of the present invention
Figure 91:
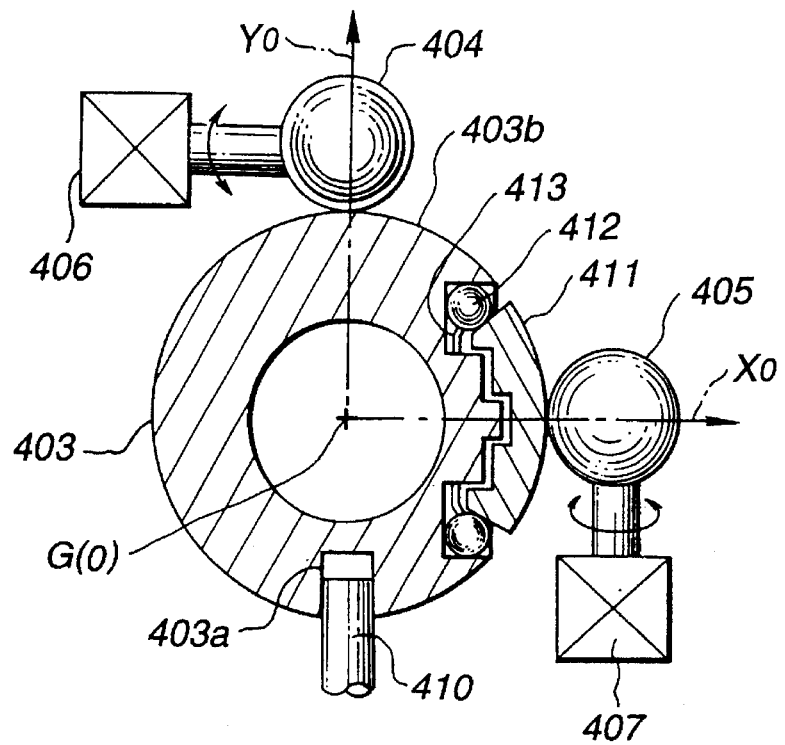
FIG. 91 is a longitudinal sectional view of the lens frame supporting mechanism shown in FIG. 90.

FIG. 90 is an oblique view of the lens frame supporting mechanism of this embodiment. FIG. 91 is a longitudinal sectional view of a major portion of a lens barrel unit 402 for the lens frame supporting mechanism. The lens frame supporting mechanism of the lens barrel unit 402 differs from the lens frame supporting mechanism of the first embodiment described in conjunction with FIG. 1 in that a lens frame 403 has an independent rotary member 411 that, when the lens frame 403 is in the neutral state, is rotatable about an axis which passes through the rotation center G on the optical axis O and is perpendicular to the optical O; that is, a horizontal axis XO.

The independent rotary member 411 has a spherical surface, which acts as a driven and supported member movable within a movable zone centered on the rotation center G, as the outer surface thereof. The other components are identical to those of the lens supporting mechanism of the first embodiment shown in FIG. 1.

The lens frame supporting mechanism of this embodiment will be described in more detail. As shown in FIGS. 90 and 91, the lens frame 403 has a spherical surface 403b that is a supported member and acts as a driven member. A first supporting driving member 404, which is made of a frictional material, is substantially in point contact with the spherical surface 403b at a point joined with the rotation center G by the vertical axis YO. A second supporting driving member 405, which is made of a frictional material, is substantially in point contact with the spherical surface of the independent rotary member 411 at a point joined with the rotation center G by the XO axis. These supporting driving members 404 and 405 are actuated to rotate by means of actuators 406 and 407.

A rotation restraining pin 410 included in a movement restrainer that controls rolling restraint is located at the bottom of the lens frame 403 to which the vertical axis YO extends. The rotation restraining pin 410 is fitted in a guide ditch 403a which is parallel with the optical axis OO in the bottom of the lens frame 403. Similar to the lens frame supporting mechanism of the first embodiment shown in FIG. 1, ball bearings 408a, 408b, and 409 are arranged on the part of the spherical surface 403b of the lens frame 403 opposed to the independent rotary member 411.

Figure 92:
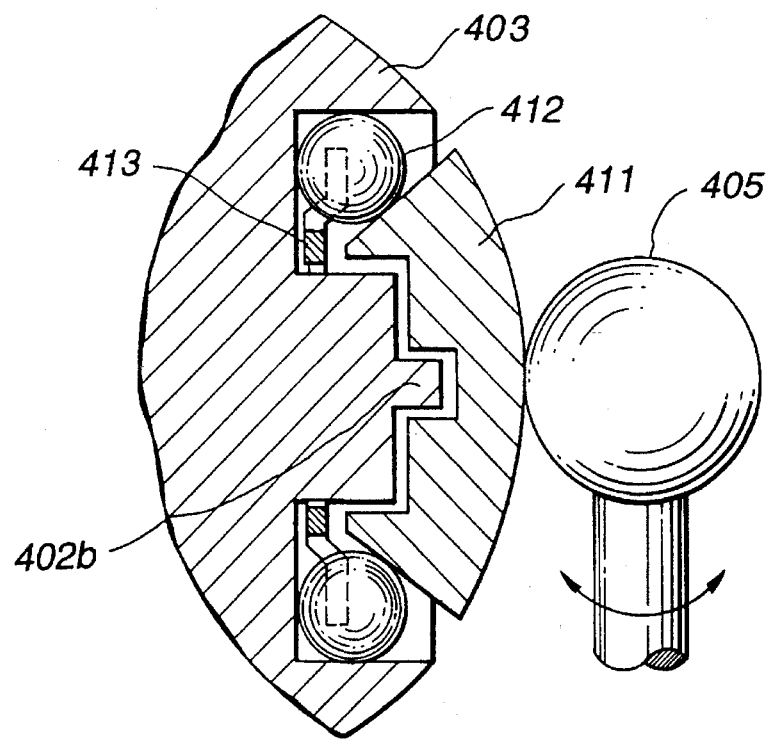
FIG. 92 is an enlarged sectional view showing an independent rotary member in the lens frame supporting mechanism shown in FIG. 90.

When the independent rotary member 411 is mounted on the lens frame 403 as will be described, as shown in the sectional view of FIG. 91 and the enlarged sectional view of the independent rotary member of FIG. 92, the tapered surface of the independent rotary member 411 is supported by a plurality of precision axis ball bearings 412 so that the independent rotary member 411 can rotate. The plurality of precision axis ball bearings 412 are held by ball holders 413 so that they will not abut one another, and are held in a recess of the lens frame 403 so that they can roll freely. A mechanism installed in a center 402b exerts the effect of preventing the independent rotary member 411 from coming off in the axial direction.

Figure 93A:
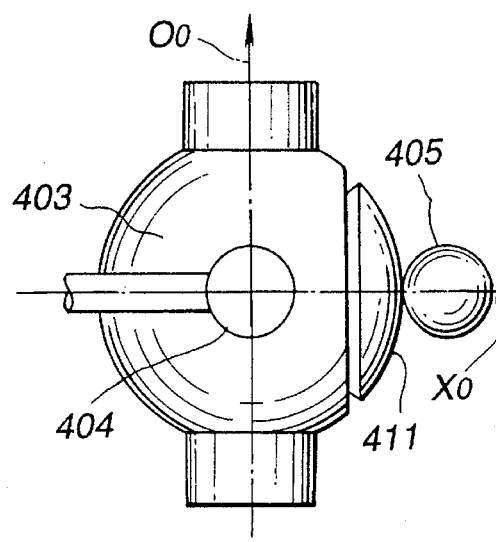
FIGS. 93A and 93B are plan views showing a major portion of the lens frame supporting mechanism shown in FIG. 90 in a state of operation in which the lens frame is respectively in a neutral state and in a state in which the optical axis shifts to a Θ direction.

FIGS. 93A through 96 show the states of rotation of the lens frame supporting mechanism of this embodiment having the foregoing structure. FIGS. 93A and 94A are plan and bottom views, wherein the lens frame 403 is in the neutral state. When the second supporting driving member 405 is rotated in the state shown in FIG. 93A, the lens frame 403 rotates by an angle θ. As shown in the plan view of FIG. 93B or the bottom view of FIG. 94B, the optical axis of the lens frame shifts to an O1 direction. An axis perpendicular to the optical O1 is oriented in an X1 direction. FIG. 95A is a view of FIG. 93B looking in the direction of arrow 95A.

Figure 93B:
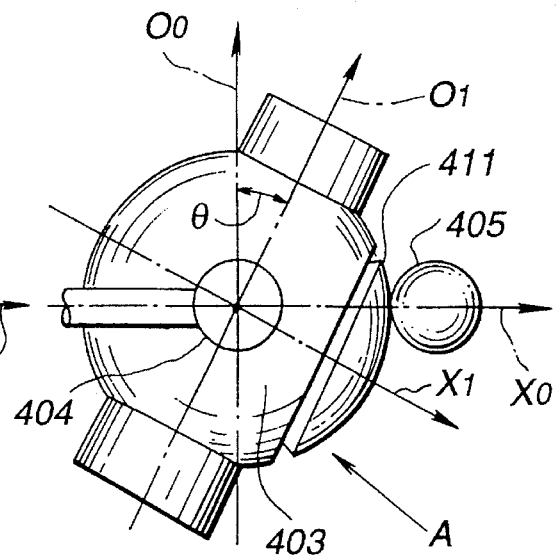
Figure 94A:
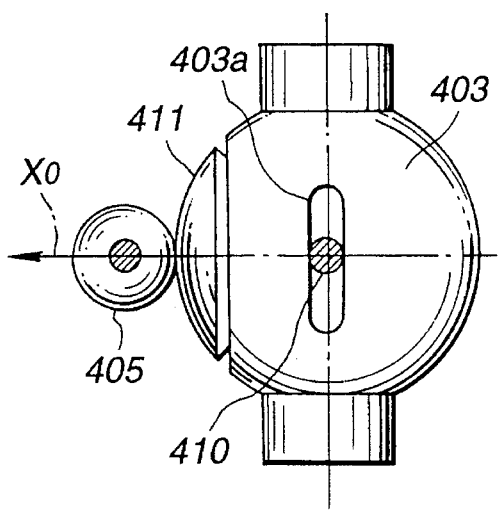
FIG. 94A is a bottom view showing the major portion of the lens frame supporting mechanism shown in FIG. 90 in the same state of operation as the one shown in FIG. 93A.
Figure 94B:
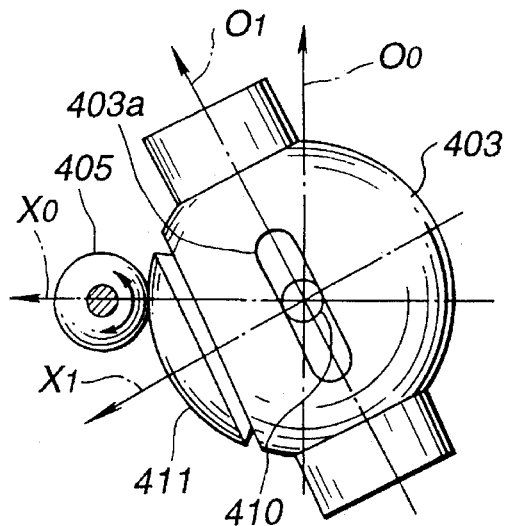
FIG. 94B is a bottom view showing the major portion of the lens frame supporting mechanism shown in FIG. 90 in the same state of operation as the one shown in FIG. 93B.
Figure 95A:
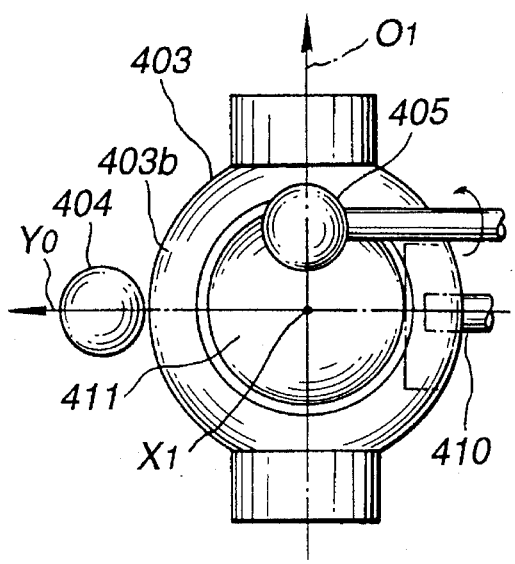
FIG. 95A is a view of FIG. 93B looking in the direction of arrow 95A and showing a state of operation of the lens frame supporting mechanism shown in FIG. 90.
Figure 95B:
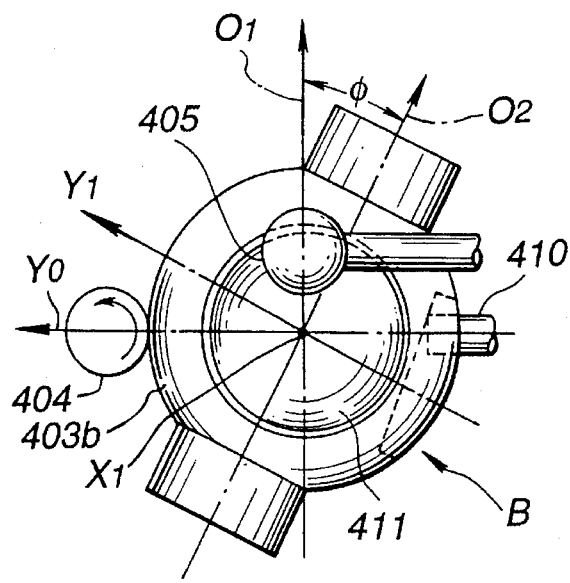
Figure 96:
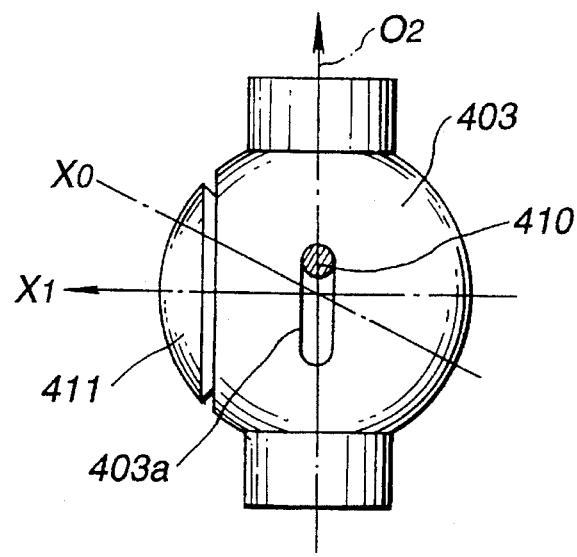

When the first supporting driving member 404 is rotated in the state in FIG. 95A or FIG. 93B, the lens frame 403 rotates by an angle φ, changes from the state shown in FIG. 95A to the one shown in FIG. 95B, and shifts the optical axis thereof in an O2 direction. An axis perpendicular to the optical axis O2 is oriented in an Y1 direction. FIG. 96 is a view of FIG. 95B looking in the direction of arrow 96.

When the lens frame 403 is driven to rotate, since the independent rotary member 411 is rotatable about the X1 axis, the second supporting driving member 405 does not slip at the contact point relative to the independent rotary member 411. A state of friction slide will not be established.

Unlike the conventional supporting mechanism, there is no possibility of causing an increase in a driving load to the first supporting driving member 404, which results from the friction slide due to the slip occurring at the contact point. This resolves the problem that the supporting mechanism malfunctions due to an insufficient torque when driven by the actuator 406 or that a current consumption increases. At the same time, deterioration in durability resulting from friction diminishes.

In the aforesaid sixth embodiment, the independent rotary member 411 is opposed to the second supporting driving member 405. A lens supporting mechanism in which an independent rotary member is opposed in the first supporting driving member 404 located in the vertical direction may be proposed as a variant of the sixth embodiment.

Figure 97:
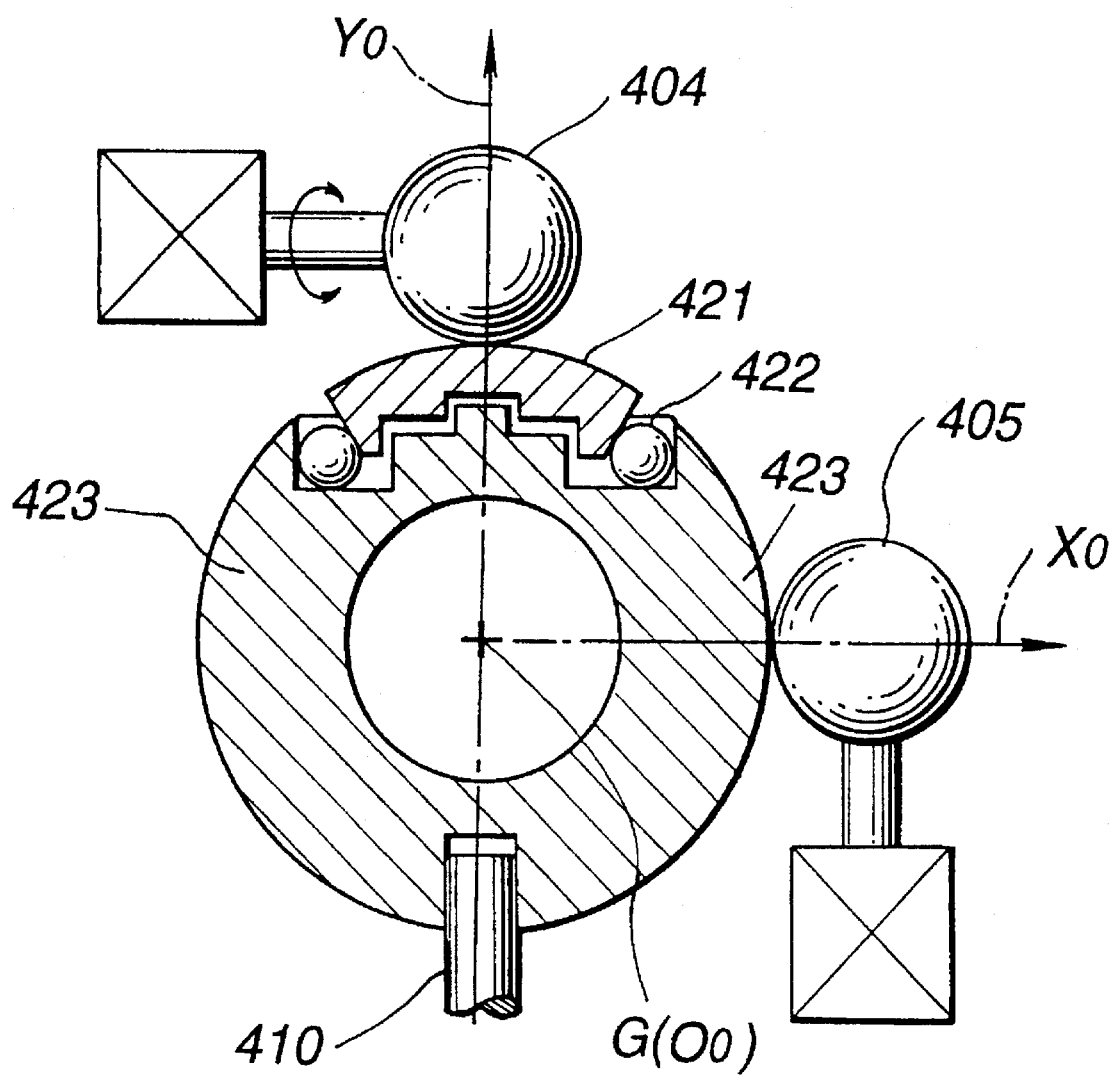

FIG. 97 is a longitudinal sectional view of the lens frame supporting mechanism of the above variant. In FIG. 97, the supporting mechanism stays in the neutral state. An independent rotary member 421, which is rotatable about the vertical axis YO, is supported by precision axis ball bearings and is mounted on a lens frame 423. The first supporting driving member 404 lies in contact with the spherical surface of the independent rotary member 421 that is a supported member and acts as a driven member. The second supporting driving member 405 lies in contact with the part of a spherical surface 423b that is a supported member and acts as a driven member and to which the horizontal axis XO extends.

In the lens frame supporting mechanism of this variant, the first supporting driving member 404 hardly causes friction slide, and an increase in a driving load to the second supporting driving member 405 is minimized.

Similar to the sixth embodiment, the independent rotary member 411 may also be formed in the part of the lens frame in contact with the second supporting driving member 405 in the supporting mechanism of this variant. According to the variant having this structure, both the first and second supporting driving members 404 and 405 hardly slip. The driving load can further be diminished.

Next, a lens frame supporting mechanism of the seventh embodiment of the present invention will now be described.

In the sixth embodiment, the movement restrainer is composed of the guide ditch 403a and the rotation restraining pin 510 which are formed in the lens frame 403. In contrast, as shown in the sectional view of FIG. 98, a movement restrainer employed for the lens frame supporting mechanism of this embodiment has a member, in which a guide ditch 436a is formed, independently of a lens frame 433. The member is mounted in the lens frame 433 so as to rotate freely about the vertical axis YO passing through the rotation center G.

To be more specific, a support axis 434, which is supported by a sleeve 435 fixed to the lens frame 433 so as to be freely rotatable, is aligned with the vertical axis YO and located at the bottom of the lens frame 433 that is the opposite side of the part thereof lying in contact with the first supporting driving member 404. A position regulation guide member 436 is fixed to the distal part of the support axis 434. The guide ditch 436a is formed in the guide member 436. A rotation restraining pin 437, which is fixed to a lens frame supporting member and serves as a movement restraining member, is fitted in the guide ditch 436a so that the rotation restraining pin 437 can slide freely.

Figure 98:
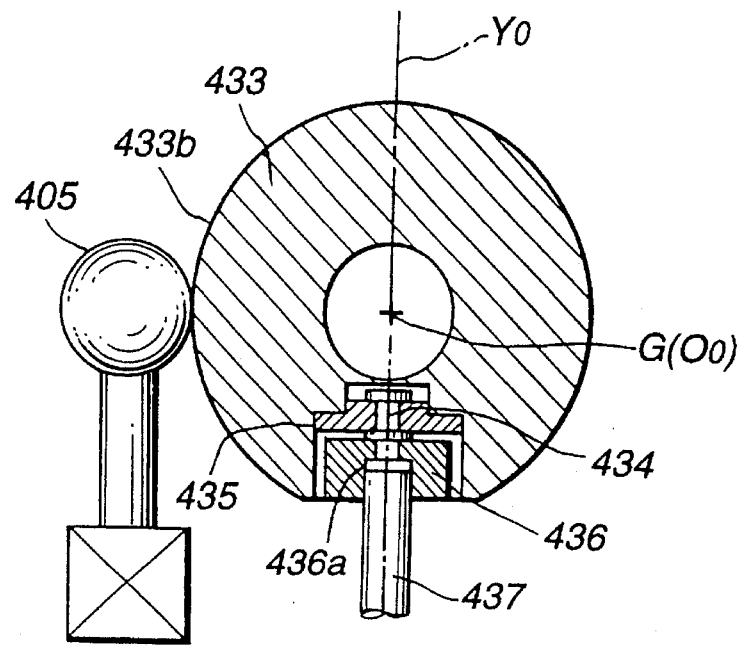
Figure 99:
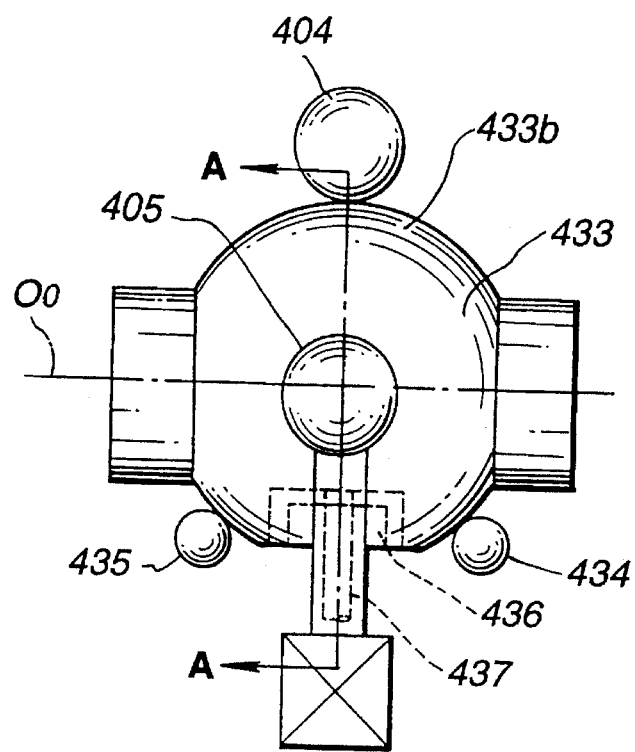

Even in the supporting mechanism of this embodiment, as shown in FIG. 98 and the side view of FIG. 99, the first and second supporting driving members 404 and 405 lie in contact with a spherical surface 433b of the lens frame 433. The part of the lens frame 433 opposed to the part thereof in contact with the first and second supporting driving members 404 and 405 is supported by ball bearing members 438 and 439, and a ball bearing member that is not shown.

Next, the rotating operation of the lens frame supporting mechanism of this embodiment having the foregoing structure will now be described.

Figure 100A:
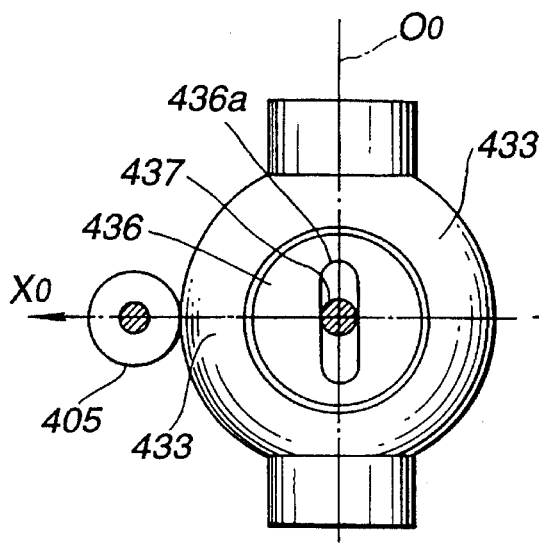
Figure 100B:
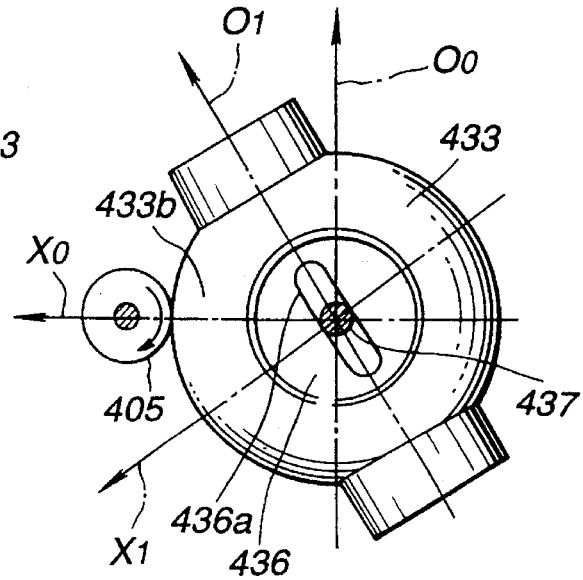
Figure 100C:
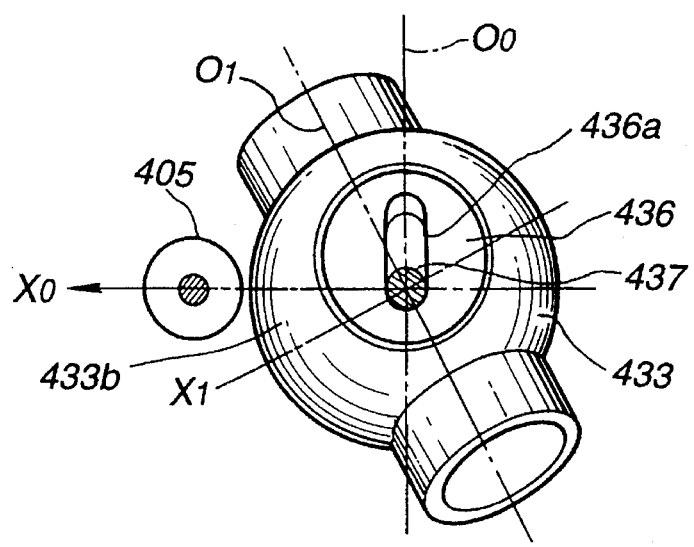

FIGS. 100A, 100B and 100C show the bottom of the lens frame supporting mechanism; that is, states of movement viewed from the side of the rotation restraining pin 437. In FIG. 100A, the lens frame 433 is in a neutral state. In FIG. 100B, the second supporting driving member 405 is actuated so that the optical axis of the lens frame 433 will be oriented in an O1 direction. In the state in FIG. 100B, since the first supporting driving member 404 has not rotated, the guide member 436 rotates together with the lens frame 433.

When the first supporting driving member 404 is rotated, the lens frame 433 changes from the state in FIG. 100B to the one in FIG. 100C. At this time, the rotation restraining pin 437 causes the guide member 436 to rotate. The guide ditch 436a in the guide member 436 is oriented to be in parallel with the OO axis whose direction is consistent with that of the tangent at the contact point of the first supporting driving member 404.

As mentioned above, when the guide ditch 436a is in parallel with the OO axis, the lens frame 433 can rotate about the XO axis perpendicular to the OO axis. The drive hardly allows the first supporting driving member 404 to slip at the contact point relative to the spherical surface 433b of the lens frame 433 or the second supporting driving member 405 to slip at the contact point relative to the spherical surface 433b of the lens frame 433. In this state of drive, frictional slide resistance resulting from a slip does not work. A phenomenon that the torque of a load to an actuator increases does not occur.

Next, a lens frame supporting mechanism of the eighth embodiment of the present invention will now be described below.

Figure 102:
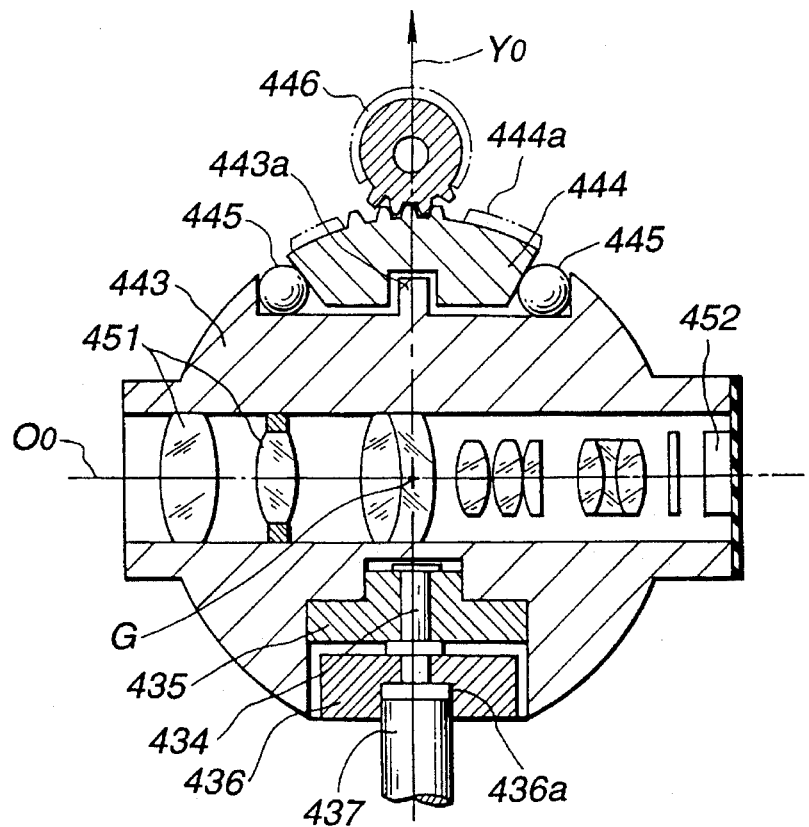

In the lens frame supporting mechanism of this embodiment, as shown in the front view of FIG. 101 or the longitudinal sectional view of FIG. 102, an independent rotary member 444, which rotates with the rotation center G as a center and has a gear 444a movable in a rotation zone, is mounted on the top of a lens frame 443 so that the independent rotary member 444 can rotate freely. A pinion 446, which is engaged with the gear 444a and serves as a first supporting driving member, is placed on the top of the lens frame 443.

The other components will be described. The independent rotary member 411 employed in the sixth embodiment is mounted on the part of the lens frame 443 joined with the rotation center G by a horizontal axis XO so that, when the lens frame 443 is in the neutral state, member 411 is horizontal. The second supporting driving member 405 abuts on the spherical surface of the independent rotary member 411 that is a supported member and acts as a driven member. The position regulation guide member 436 and rotation restraining pin 437, which constitute the movement restrainer and are employed in the seventh embodiment, are located at the bottom of the lens frame 443.

The independent rotary member 444 is mounted on the lens frame 443 via a plurality of precision axis ball bearings 445, which can roll on the lens frame 443, so that the independent rotary member 444 can rotate freely. The independent rotary member 444 rotates about the vertical axis YO so that, when the lens frame 443 is in the neutral state, axis YO passes through the rotation center G and is vertical. A mechanism for preventing the independent rotary member 444 from coming off from the lens frame 443 is installed in a recess 443a. The pinion 446 engages the gear 444a. When the independent rotary member 444 having the gear 444a rotates, the pinion 446 may disengage from the gear 444a. Annular guides 446a are therefore attached to the opposing side surfaces of the pinion 446.

A lens array 451 and imaging device such as a CCD 452 are arranged along the optical OO in the lens frame 443.

The rotating operation of the lens frame supporting mechanism of this embodiment having the foregoing structure will now be described.

FIGS. 103A to 103C are plan views showing states of operation of the lens frame supporting mechanism. In FIG. 103A, the lens frame 443 is in the neutral state. In FIG. 103B, the second supporting driving member 405 is rotated so that the optical axis of the lens frame 443 will be oriented in the O1 direction. In the state in FIG. 103B, the independent rotary member 444 is rotatable. The direction in which the gear 444a is actuated is consistent with that of the OO axis so that, when the lens frame 443 stays in the neutral state, axis OO acts as a reference optical axis. When the pinion 446 is rotated, the lens frame 443 changes from the state shown in FIG. 103B to the one shown in FIG. 103C; that is, rotates to orient the optical axis thereof in the O2 direction.

In the above state of drive, the lens frame 443 can rotate about the XO axis perpendicular to the OO axis owing to the movement restrainer. Moreover, the second supporting driving member 405 does not slip at a contact point owing to the independent rotary member 411. There is therefore no possibility that the load to an actuator for driving the pinion 446 increases due to friction slide. In this embodiment, the first supporting driving member is the pinion 446. Deterioration in durability resulting from friction will therefore not occur.

Next, a lens frame supporting mechanism of the ninth embodiment of the present invention will now be described.

FIG. 104 is an oblique view of the lens frame supporting mechanism of this embodiment. A lens barrel unit for the lens frame supporting mechanism is designed to hold a lens array 481, comprising: a lens frame 483 having a spherical surface 483a that is a supported member and acts as a driven member; an independent rotary member 485 that is supported by the lens frame 483 so as to be rotatable about the X axis of the lens frame 483, and that has a spherical surface and is a supported member and acts as a driven member; projections 484 that are supporting members for supporting the lens frame 483 so that the lens frame 483 can rotate with the rotation center G as a center; an ultrasonic transducer 486 that has an output member 486a which lies in contact with the spherical surface of the independent rotary member 485 and thus supports the independent rotary member 485, and that serves as an X-axis actuator; an ultrasonic transducer 487 that has an output member 487a which lies in contact with the spherical surface 483a of the lens frame 483 and thus supports the lens frame 483, and that serves as a Y-axis actuator; and a movement restraining member, which is not shown, for restraining the lens frame 483 from rolling.

The output member 486a of the ultrasonic transducer 486 is actuated to move the spherical surface of the independent rotary member 485 in the direction of the O axis. The output member 487a of the ultrasonic transducer 487 is actuated to move the spherical surface 483a of the lens frame 483 in the direction of the O axis.

In the lens frame supporting mechanism of this embodiment having the foregoing structure, the lens frame 483 and the ultrasonic transducers 486 and 487 constitute a structure of an ultrasonic motor. The lens frame 483 can rotate about the X and Y axes. Specifically, when the ultrasonic transducer 487 is actuated, the lens frame 483 is directly driven to rotate about the X axis perpendicular to the Y axis. When the ultrasonic transducer 486 is actuated, the lens frame 483 is driven via the independent rotary member 485 to rotate about the Y axis perpendicular to the X axis.

In the lens frame supporting mechanism of this embodiment, similar to the lens frame supporting mechanism described as the sixth embodiment, the independent rotary member 485 that is rotatable about the X axis is adopted as one of the driven members. An increase in a driving load resulting from friction resistance is therefore limited, enabling rotational drive with a smaller driving torque. Furthermore, since ultrasonic transducers are adopted as actuators, the speed of response to rotation drive is high. The lens barrel unit can be designed more compactly.

The lens frame supporting mechanism of the present invention can be employed not only as a hand tremor compensation mechanism but also as a rotation mechanism for a lens barrel including a tilting mechanism for a camera. The CCD used as a imaging device need not be united with the lens frame. The present invention can apply to a camera in which the CCD is incorporated in a camera body. The lens frame supporting mechanism may be used as a rotation drive mechanism for a lens frame. Furthermore, the lens frame supporting mechanism according to the present invention can apply not only to a camera-inclusive VTR but also to an electronic still camera. Alternatively, the lens frame supporting mechanism can be employed as a lens frame rotation mechanism for a silver film camera (i.e. a still camera).

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein described.

What is claimed is:

1. A lens frame supporting mechanism, comprising:
   a spherical surface that is a specified region of an outer surface of a lens frame, and includes spherical areas covering at least movable zones of said lens frame, and is a driven and supported member;
   supporting driving members being substantially in point contact with said spherical areas of said spherical surface, and supporting said associated spherical areas, and at least one of which drives its associated spherical area by rotating in contact with said associated spherical area in order to rotate and displace said associated spherical area in a given direction; and
   a movement restrainer that restrains said lens frame from rotating about an optical axis, and permits movement in all other directions except the given rotation direction, and stays between said lens frame and a support member.

2. A lens frame supporting mechanism according to claim 1, wherein said spherical surface of said lens frame has a center which is a rotation center and lies in a vicinity of a center of gravity of said lens frame.

3. A lens frame supporting mechanism according to claim 1, wherein said movement restrainer includes means enabling said lens frame to rotate about an axis, which is perpendicular to a scanning line on an imaging device and passes through a center of said spherical surface, in whichever direction said lens frame is oriented.

4. A lens frame supporting mechanism according to claim 3, wherein said movement restrainer is composed of a guide ditch formed along an optical axis in an outer surface of said lens frame, and a guide pin that is placed between members for supporting said lens frame and is fitted in said guide ditch so as to slide freely.

5. A lens frame supporting mechanism according to claim 3, wherein said movement restrainer is composed of a projecting fin formed along an optical axis in an outer surface of said lens frame, and a fin guide that is formed as part of a member for supporting said lens frame and having a slot for slidably receiving said fin.

6. A lens frame supporting mechanism according to claim 1, wherein a plane joining a contact point between said driven and supported spherical surface of said lens frame and one of said supporting driving members with said center of said spherical surface is perpendicular to a reference optical axis or an optical axis so that when said lens frame is in a neutral state, said optical axis is defined as a reference.

7. A lens frame supporting mechanism according to claim 6, wherein an axis passing through a contact point between said driven and supported spherical surface of said lens frame and one of said supporting driving members and a center of said spherical surface is perpendicular to an axis passing through a contact point between said driven and supported spherical surface and said supporting driving members and said center of said spherical surface.

8. A lens frame supporting mechanism according to claim 7, wherein one of said contact points between said driven and supported spherical surface of said lens frame and said supporting driving members is located on an axis that is perpendicular to a scanning line on an imaging device and rotatable about an axis passing through said center of said spherical surface.

9. A lens frame supporting mechanism according to claim 1, wherein contact surfaces between said driven and supported spherical surface of said lens frame and said supporting driving members are frictional contact surfaces.

10. A lens frame supporting mechanism according to claim 1, further including a locking mechanism means that secures part of said outer surface of said lens frame with an external lock member, and thus holds said lens frame in such a manner that the optical axis of said lens frame will be oriented in a direction of a reference optical axis.

11. A lens frame supporting mechanism, comprising:

a spherical surface that is a specified region of an outer surface of a lens frame, and includes spherical areas covering at least movable zones of said lens frame, and is a driven and supported member;

a supporting driving member that is substantially in point contact with an associated one of said spherical areas of said spherical surface, and supports said associated spherical area, and drives said associated spherical area by rotating in contact with said associated spherical area in order to rotate and displace said associated spherical area;

a ditch that is located in a specified region of the outer surface of said lens frame, formed to lie on a plane lying in parallel with an optical axis of said lens frame so as to draw a circular arc, and acts as a driven and supported member; and a second supporting driving member that is fitted in said ditch so as to slide freely, supports said ditch, rotates and displaces said ditch, and works as a movement restrainer for restraining said lens frame from rotating about the optical axis.

12. A lens frame supporting mechanism, comprising:

a lens frame;

supporting members for supporting said lens frame so that said lens frame can rotate in any direction with substantially one point in said lens frame being a center of rotation;

at least two actuators for rotating said lens frame supported by said supporting members;

driven members formed on said lens frame; and an independent rotary member that is mounted on said lens frame, is located at a specified position on an outer surface of said lens frame, is rotatable about an axis which lies substantially in parallel with a plane perpendicular to the optical axis of said lens frame, and is engaged by at least one of said actuators.

13. A lens frame supporting mechanism according to claim 12, wherein each of said actuators and driven members are composed of gears, a center axis of one group of driving gears is consistent with a center axis of another group of driving gears, the center axis of the other group of said driving gears is consistent with a center axis of said independent rotary member that is rotatable, the center axes of said driving gears are perpendicular to center axes of driven gears, and intersections between a rotation center of said lens frame and the center axes of said driven gears are consistent with one another.

14. A lens frame supporting mechanism according to claim 12, wherein said actuators and driven members are friction transmission members.

15. A lens frame supporting mechanism according to claim 12, 13, or 14, wherein said lens frame includes a movement restrainer for restraining said lens frame from rotating about the optical axis.

16. A lens frame supporting mechanism according to claim 12, 13, or 14, wherein said supported member is a spherical surface.

17. A lens frame supporting mechanism according to claim 13, wherein a centering drive guide is formed in an outer surface of said independent rotary member.

18. A lens frame supporting mechanism according to claim 13, wherein projections are formed as supporting members on an outer surface of said independent rotary member.

19. A lens frame supporting mechanism, comprising:

a lens frame that is rotatable with substantially one point as a center of rotation;

lens frame rotation actuators located adjacent to a trough of a rotation trajectory of an outline of said lens frame, which trough lies on a plane passing through a center of rotation of said lens frame and perpendicularly intersecting an optical axis that when said lens frame is in a neutral state, is defined as an optical axis of said lens frame;

reduction gear units located adjacent to said trough;

lens frame supporting members located adjacent to said trough; and lens frame rotation supporting structure members, located adjacent to said trough, for holding said lens frame supporting members, said actuators, and said gear units all together, being coupled with a main structural member of a camera.

20. A lens frame supporting mechanism, comprising:

a lens frame rotatable with substantially one point as a center of rotation;

supporting members for rotatably supporting said lens frame;

actuators for rotating said lens frame;

lens frame rotating members driven by said actuators for rotating said lens frame; and a constraining means for exerting a moment of rotation on said lens frame so that said lens frame can rotate about a rotation axis of said lens frame within a given rotation range thereof.

21. A lens frame supporting mechanism according to claim 20, wherein said constraining means is a single mechanism and exerts a moment of rotation for rotation about any rotation axis.

22. A lens frame supporting mechanism according to claim 20, wherein said constraining means is located at a position at which said constraining means has substantially no effect upon a constraining force exerted by said supporting members on said lens frame.

23. A lens frame supporting mechanism, comprising:

a lens frame that is rotatable with substantially one point as a center of rotation;

lens frame supporting members for rotatably supporting said lens frame;

lens frame rotation actuators for driving said lens frame via gear units;

lens frame rotation supporting structure members for holding said lens frame supporting members, said gear units, and said actuators all together, and being coupled with a major structural member of a camera; and a spherical bearing member located on a side surface of said lens frame, and having a built-in optical element driving actuator.

24. In combination a lens frame and a lens frame support assembly, said lens frame including a lens having an optical axis;

a portion of the lens frame having spherical surface portions with a common center which lies on said optical axis;

said common center being a center of rotation of said lens frame;

said lens frame support assembly including first and second driving supporting members each making substantially point contact with an associated one of said spherical surface portions to thereby support said lens frame;

said first and second driving supporting members each being selectively rotatable to respectively rotate said spherical surface portions and hence said lens frame about first and second axes of rotation transverse to said optical axis and passing through said center of rotation; and restraining means slidably engaging said lens frame to restrain said lens frame from rotation about said optical axis while permitting rotation in other directions under control of said driving supporting members.

25. In combination a lens frame and a lens frame support assembly, said lens frame including a lens having an optical axis;

a portion of the lens frame having arcuate-shaped portions with a common center which lies on said optical axis;

said common center being a center of rotation of said lens frame;

said lens frame support assembly including first and second driving supporting members each making substantially point contact with an associated one of said arcuate-shaped portions to thereby support said lens frame;

said first and second driving supporting members each being selectively rotatable to respectively rotate said arcuate-shaped portions and hence said lens frame about first and second axes of rotation transverse to said optical axis and passing through said center of rotation; and restraining means slidably engaging said lens frame to restrain said lens frame from rotation about said optical axis while permitting rotation in other directions under control of said driving supporting members.

26. The combination of claim 25 wherein said restraining means is part of at least one of said driving supporting members;

said lens frame having an arcuate-shaped guide ditch slidably receiving said restraining means.

27. The combination of claim 25 wherein said driving supporting members each include a rotatable drive gear each of said arcuate-shaped surfaces having a drive face gear engaging one of said driving gears;

at least one of said drive gears being mounted upon a shaft, said part engaging said arcuate-shaped guide ditch being an end of said shaft.

* * * * *